(12) United States Patent
Goodrum et al.

(10) Patent No.: US 11,617,788 B2
(45) Date of Patent: Apr. 4, 2023

(54) VIRAL PROMOTERS AND COMPOSITIONS AND METHODS OF USE THEREOF

(71) Applicants: Arizona Board of Regents on Behalf of The University of Arizona, Tucson, AZ (US); The University of North Carolina at Chapel Hill, Chapel Hill, NC (US); The Board of Supervisors of Louisiana State University and Agricultural and Mechanical College, Baton Rouge, LA (US)

(72) Inventors: Felicia Goodrum, Tucson, AZ (US); Nathaniel Moorman, Chapel Hill, NC (US); Jeremy Kamil, Shreveport, LA (US)

(73) Assignees: Arizona Board of Regents on Behalf of The University of Arizona, Tucson, AZ (US); The University of North Carolina at Chapel Hill, Chapel Hill, NC (US); The Board of Supervisors of Louisiana State University and Agricultura and Mechanical Colleae, Baton Rouge, LA (US)

( * ) Notice: Subject to any disclaimer, the term of this patent is extended or adjusted under 35 U.S.C. 154(b) by 103 days.

(21) Appl. No.: 17/259,352

(22) PCT Filed: Jul. 9, 2019

(86) PCT No.: PCT/US2019/041000
§ 371 (c)(1),
(2) Date: Jan. 11, 2021

(87) PCT Pub. No.: WO2020/014222
PCT Pub. Date: Jan. 16, 2020

(65) Prior Publication Data
US 2021/0236621 A1 Aug. 5, 2021

Related U.S. Application Data

(60) Provisional application No. 62/695,664, filed on Jul. 9, 2018.

(51) Int. Cl.
*A61K 39/00* (2006.01)
*A61K 48/00* (2006.01)
*A61K 39/12* (2006.01)
*C07H 21/04* (2006.01)
*C07K 14/47* (2006.01)
*C12N 15/86* (2006.01)

(52) U.S. Cl.
CPC .............. *A61K 39/12* (2013.01); *C12N 15/86* (2013.01); *C12N 2710/16121* (2013.01); *C12N 2830/008* (2013.01)

(58) Field of Classification Search
CPC ........ C07K 14/47; A61K 39/00; A61K 48/00; A61P 35/00; A61P 37/04
See application file for complete search history.

(56) References Cited

U.S. PATENT DOCUMENTS

| | | |
|---|---|---|
| 2005/0191727 A1 | 9/2005 | Thudium |
| 2008/0153770 A1 | 6/2008 | Kim |
| 2012/0100573 A1 | 4/2012 | Thudium |
| 2014/0178968 A1 | 6/2014 | Nauclér |
| 2015/0306210 A1 | 10/2015 | Thirion |
| 2017/0035860 A1 | 2/2017 | Flynn |
| 2017/0101647 A1* | 4/2017 | Minshull ................ C12N 15/63 |
| 2017/0101658 A1 | 4/2017 | Goel |

FOREIGN PATENT DOCUMENTS

WO 2016011293 1/2016

OTHER PUBLICATIONS

Arend et al. "Multiple Transcripts Encode Full-Length Human Cytomegalovirus IE1 and IE2 Proteins during Lytic Infection" ,J Virol, 2016, 90:8855-8865.*

Albright, et al., "Myeloblastic Cell Lines Mimic Some but Not All Aspects of Human Cytomegalovirus Experimental Latency Defined in Primary CD34+ Cell Populations", J. of Virol., 87(17):982-9812 (2013).

(Continued)

*Primary Examiner* — Barry A Chestnut
(74) *Attorney, Agent, or Firm* — Pabst Patent Group LLP

(57) ABSTRACT

Viral promoters and compositions and methods of use thereof are provided. Compositions include viruses with impaired ability to reactivate from latency, and pharmaceutical compositions and method of use thereof. The genome of the viruses include one or more mutations that reduce expression from one or more promoters that regulate expression of viral genes during reactivation from latency. The mutation(s) are typically in a region of the viral genome that includes (i) promoter elements of the iP1 promoter of human cytomegalovirus, or the sequence of another virus corresponding thereto (e.g., an iP1 promoter homolog); (ii) promoter elements of the iP2 promoter of human cytomegalovirus, or sequence of another virus corresponding thereto (e.g., an iP2 promoter homolog); or (iii) a combination thereof. In some embodiments the virus encodes one or more heterologous antigens. The viruses can be used as vaccines to induce prophylactic and therapeutic immune responses in subjects in need thereof.

19 Claims, 23 Drawing Sheets
Specification includes a Sequence Listing.

(56) References Cited

OTHER PUBLICATIONS

Arend, et al., "Kinome Profiling Identifies Druggable Targets for Novel Human Cytomegalovirus (HCMV) Antivirals", Molecular & Cellular Proteomics : MCP 16, S263-S276 (2017).
Arend, et al., "The 5' Untranslated Region of the Major Immediate Early mRNA is Necessary for Efficient Human Cytomegalovirus Replication", Journal of Virology, 92: e02128-17 (2018).
Ariza-Heredia, et al., "Cytomegalovirus diseases after hematopoietic stem cell transplantation: A mini-review", Cancer Lett, 34(1)2:1-8 (2014).
Arvn, et al., "Vaccine Development to Prevent Cytomegalovirus Disease: Report from the National Vaccine Advisory Committee", Clin. Inf. Dis., 39(2):233-9 (2004).
Baum, et al., "Novel Retroviral Vectors for Efficient Expression of the Multidrug Resistance (mdr-1) Gene in Early Hematopoietic Cells", J. of. Virol., 69(12): 7541-7547 (1995).
Bhatt, et al., "AKTivation of PI3K/AKT/mTOR signaling pathway by KSHV", Front. In Immunol., 3(401): 1-16 (2013).
Boeckh, et al., "Cytomegalovirus in Hematopoietic Stem Cell Transplant Recipients: Current Status, Known Challenges, and Future Strategies", Biol. of Blood and Marrow Trans., 9(9):543-558 (2003).
Boeckh, et al., "Cytomegalovirus: pathogen, paradigm, and puzzle", The Journal of Clin. Invest., 121(5): 1673-1680 (2011).
Bradley, et al., "High-throughput sequence analysis of variants of human cytomegalovirus strains Towne and AD169", J. of Gener. Virol., 90(pt. 10):2375-2380 (2009).
Brooks, "Transcriptional silencing is associated with extensive methylation of the CMV promoter following adenoviral gene delivery to muscle", J Gene Med, 6(4): 395-404 (2004).
Brunet, et al., "Stress-dependent regulation of FOXO transcription factors by the SIRT1 deacetylase", Science, 303:2011-2015 (2004).
Buehler, et al., "Opposing Regulation of the EGF Receptor: A Molecular Switch Controlling Cytomegalovirus Latency and Replication", PLOS Pathogens, 12(5):e1005655, 28 pages (2016).
Bughio, et al., "An endothelial cell-specific requirement for the UL133-UL138 locus of human cytomegalovirus for efficient virus maturation", Journal of Virology, 87: 3062-3075 (2013).
Bughio, et al., "Human cytomegalovirus UL135 and UL136 genes are required for post-entry tropism in endothelial cells", Journal of Virology, 89: 6536-6550 (2015).
Camarena, et al., "Nature and duration of growth factor signaling through receptor tyrosine kinases regulates HSV-1 latency in neurons", Cell Host Microbe., 8(4):320-330 (2010).
Cannon, et al., Journal of clinical virology : the official publication of the Pan American Society for Clinical Virology, 46 (Suppl 4):S6-10 (2009).
Caposio, et al., "The Elk-1 and Serum Response Factor Binding Sites in the Major Immediate-Early Promoter of Human Cytomegalovirus are Required for Efficient Viral Replication in Quiescent Cells and Compensate for Inactivation of the NF-kB Sites in Proliferating Cells", J. of Virol., 84(9):4481-4493 (2010).
Caviness, et al., "Complex Interplay of the UL136 Isoforms Balances Cytomegalovirus Replication and Latency", mBio, 7:e01986-15 (2016).
Challita, et al., "Lack of expression from a retroviral vector after transduction of murine hematopoietic stem cells is associated with methylation in vivo", Proc. Natl. Sci. USA, 91(7):2567-2571 (1994).
Cheng, et al., "Transcriptome-wide characterization of human cytomegalovirus in natural infection and experimental latency", PNAS, 114(49):E10586-E10595 (2017).
Chung, et al., "Distinct role of FoxO1 in M-CSF- and GM-CSF-differentiated macrophages contributes LPS-mediated IL-10: implication in hyperglycemia", J. Leukoc. Biol., 97:327-339 (2015).
Cicin-Sain, et al., "Cytomegalovirus Infection Impairs Immune Responses and Accentuates T-cell Pool Changes Observed in Mice with Aging", PLOS Pathogens, 8(8): e1002849, 15 pages (2012).
Collins-McMillen, et al., "Alternative Promoters Drive Human Cytomegalovirus Reactivation from Latency", PNAS, 116(35):17492-17497 (2019).
Cristea, et al., "Human cytomegalovirus pUL83 stimulates activity of the viral immediate-early promoter through its interaction with the cellular IFI16 protein", Journal of Virology, 84:7803-7814 (2010).
Dargan, et al., "Sequential mutations associated with adaptation of human cytomegalovirus to growth in cell culture", The Journal of General Virology, 91:1535-1546 (2010).
Dimitrov, et al., "Therapeutic Proteins", Metho. Mol. Biol., 899:1-26 (2012).
Dolan, et al., "Genetic content of wild-type human Cytomegalovirus", J. of Gen, Virol., 85(Pt. 5):1301-1312 (2004).
Gilley, et al., "FOXO transcription factors directly activate bim gene expression and promote apoptosis in sympathetic neurons", The J. of Cell Biol., 162(4):613-622 (2003).
Goodrum, et al., "Human cytomegalovirus gene expression during infection of primary hematopoietic progenitor cells: a model for latency", PNAS, 99:16255-16260 (2002).
Greer, et al., "The energy sensor AMP-activated protein kinase directly regulates the mammalian FOXO3 transcription factor", The Journal of Biological Chemistry, 282: 30107-30119 (2007).
Guo, "Evaluation of promoter strength for hepatic gene expression in vivo following adenovirus-mediated gene transfer", Gene Ther., 3(9):802-810 (1996).
Gustems, et al., "Regulation of the Transcription and Replication Cycle of Human Cytomegalovirus is Insensitive to Genetic Elimination of the Cognate NF-kB Binding Sites in the Enhancer", J. of Virol., 80(19): 9899-9904 (2006).
Hansen, et al., "Effector memory T cell responses are associated with protection of rhesus monkeys from mucosal simian immunodeficiency virus challenge", Nature Medicine, 15(3):293-2199 (2009).
High, et al., "Chronic Infection and Frailty: Surrogate Markers, Associations, and Causality", JAGS, 53(5):906-908 (2005).
Ibanez, et al., "Human cytomegalovirus productively infects primary differentiated macrophages", J. Virol., 65:6581-6588 (1991).
International Search Report for PCT/US2019/041000 dated Oct. 10, 2019.
Ioudinkova, et al., "Control of human cytomegalovirus gene expression by differential histone modifications during lytic and latent infection of a monocytic cell line", Gene, 384:120-128 (2006).
Khan, et al., "Bcl-3-Regulated Transcription from Major Immediate-Early Promoter of Human Cytomegalovirus in Monocyte-Derived Macrophages", The J. of Immunol., 182(12):7784-7794 (2009).
Kondo, et al., "Human cytomegalovirus latent gene expression in granulocyte-macrophage progenitors in culture and in seropositive individuals", PNAS, 93(20):11137-11142 (1996).
Kops, et al., "Forkhead transcription factor FOXO3a protects quiescent cells from oxidative stress", Nature, 419(6904): 316-321 (2002).
Koskinen, et al., "Cytomegalovirus infection and accelerated cardiac allograft vasculopathy in human cardiac allografts", The Journal of Heart and Lung Transplantation, 12(5):724-729 (1993).
Lazzarotto, et al., "Human cytomegalovirus replication correlates with differentiation in a hematopoietic progenitor cell line and can be modulated by HIV-1", Arch. Virol., 135:13-28 (1994).
Lenarcic, et al., "An unbiased proteomics approach to identify human cytomegalovirus RNA-associated proteins", Virology, 481:13-23 (2015).
Li, et al., "An Epistatic Relationship Between the Viral Protein Kinase UL97 and the UL133-UL138 Latency Locus During the Human Cytomegalovirus Lytic Cycle", Journal of Virology, 88(11):6047-6060 (2014).
Malik, et al., "Retroviral-Mediated Gene Expression in Human Myelomonocytic Cells: A Comparison of Hematopoietic Cell Promoters to Viral Promoters", Blood, 86(8):2993-3005 (1995).
Martinez, et al., "CTCF Binding to the First Intron of the Major Immediate Early (MIE) Gene of Human Cytomegalovirus (HCMV) Negatively Regulates MIE Gene Expression and HCMV Replication", J. of Virol., 88(13):7389-7401 (2014).
Melnick, et al., "Cytomegalovirus and atherosclerosis", Archivum immunologiae et therapiae experimentalis, 44(5-6):297-302 (1996).

(56) References Cited

OTHER PUBLICATIONS

Møller, et al., "miRNA-mediated targeting of human cytomegalovirus reveals biological host and viral targets of IE2", PNAS, 115:1069-1074 (2018).
Moorman, et al., "A targeted spatial-temporal proteomics approach implicates multiple cellular trafficking pathways in human cytomegalovirus virion maturation", Molecular & Cellular Proteomics : MCP, 9(5):851-860 (2010).
Moorman, et al., "Human cytomegalovirus protein UL38 inhibits host cell stress responses by antagonizing the tuberous sclerosis protein complex", Cell Host & Microbe, 3: 253-262 (2008).
Murphy, et al., "Suppression of immediate-early viral gene expression by herpesvirus-coded microRNAs: Implications for latency", PNAS, 105(14): 5453-5458 (2008).
Murrell, et al., "Genetic Stability of Bacterial Artificial Chromosome-Derived Human Cytomegalovirus during Culture In Vitro", Journal of Virology, 90:3929-3943 (2016).
Nakajima, et al., "Transcriptional Regulation of ILT Family Receptors" J. Immunol., 171 (12) 6611-6620 (2003).
O'Connor, et al., "A myeloid progenitor cell line capable of supporting human cytomegalovirus latency and reactivation, resulting in infectious progeny", Journal of Virology, 86:9854-9865 (2012).
Oswald, et al., "Fine-tuning of FOX03A in cHL as a survival mechanism and a hallmark of abortive plasma cell differentiation", Blood, 131(14):1556-1567 (2018).
Paredis, et al., "Human Cytomegalovirus: Bacterial Artificial Chromosome (BAC) Cloning and Genetic Manipulation", Curr. Protoc. Microbiol., Chapter 14(Unit 14E) 37 pages (2012).
Petrucelli, et al., "Characterization of a Novel Golgi Apparatus-Localized Latency Determinant Encoded by Human Cytomegalovirus", J. of Virol., 83(11):5615-5629 (2009).
Qin, et al., "Heterologous Viral Promoters Incorporated into the Human Cytomegalovirus Genome are Silenced during Experimental Latency", J. of Virol., 87(17): 9887-9894 (2013).
Raja, et al., "A Herpesviral Lytic Protein Regulates the Structure of Latent Viral Chromatin", mBio, 7:e00633-16 (2016).
Razonable, et al., "Cytomegalovirus in solid organ transplantation", American Journal of Transplantation, 13 Suppl. 4:93-106 (2013).
Reeves, et al., "Aspects of human cytomegalovirus latency and reactivation", Current Topics in Microbiology and Immunology, 325:297-313 (2008).
Reeves, et al., "Chromatin-mediated regulation of Cytomegalovirus gene expression", Virus Res., 157(2): 134-143 (2011).
Reeves, et al., "Latency, chromatin remodeling, and reactivation of human cytomegalovirus in the dendritic cells of healthy carriers", PNAS, 102(11): 4140-4145 (2005).
Remezani, et al., "Lentiviral Vectors for Enhanced Gene Expression in Human Hematopoietic Cells", Mol. Ther., 2(5):458-469 (2000).
Saffert, et al., "Cellular and Viral Control over the Initial Events of Human Cytomegalovirus Experimental Latency in CD34+ Cells", J., of Virol., 84(11): 5594-5604 (2010).
Saffert, et al., "Human cytomegalovirus gene expression is silenced by the Daxx-mediated intrinsic immune defense when model latent infections are established in vitro", Journal of Virology, 81(17):9109-9120 (2007).
Schmaltz, et al., "Chronic cytomegalovirus infection and inflammation are associated with prevalent frailty in community-dwelling older women", Journal of the American Geriatrics Society, 53(5):747-754 (2005).
Sinclair, et al., "Chromatin structure regulates human cytomegalovirus gene expression during latency, reactivation and lytic infection", Biochimica et Biophysica Acta, 1799(3-4):286-295 (2010).
Smith, et al., "Human Cytomegalovirus Induces Monocyte Differentiation and Migration as a Strategy for Dissemination and Persistence", J. of Virol., 78(9):4444-4453 (2004).
Soderberg-Naucler, et al., "Reactivation of Latent Human Cytomegalovirus by Allogeneic Stimulation of Blood Cells from Healthy Donors", Cell, 91(1):119-126 (1997).
Soderberg-Naucler, et al., "Reactivation of latent human cytomegalovirus in CD14(+) monocytes is differentiation dependent", Journal of Virology, 75(16):7543-54 (2001).
Stahl, et al., "The Forkhead Transcription Factor FoxO in Response Regulates Transcription of p27 Kip1 and Bim to IL-2", The J. of Immunol., 168:5024-5031 (2002).
Steinberg, et al., "Multiple Spliced and Unspliced Transcripts from Human Cytomegalovirus Immediate-Early Region 2 and Evidence for a Common Initiation Site within Immediate-Early Region 1", J. of Virol., 56(3): 665-675 (1985).
Stenberg, et al., "Promoter-specific trans activation and repression by human cytomegalovirus immediate-early proteins involves common and unique protein domains", Journal of Virology, 64:1556-1565 (1990).
Streblow, et al., "Mechanisms of cytomegalovirus-accelerated vascular disease: induction of paracrine factors that promote angiogenesis and wound healing", Current Topics in Microbiology and Immunology, 325: 397-415 (2008).
Su, et al., "Human cytomegalovirus UL37 immediate early target minigene RNAs are accurately spliced and polyadenylated", Journal of General Virology, 84(1):29-39 (2003).
Sylwester, et al., "Broadly targeted human cytomegalovirusspecific CD4+ and CD8+T cells dominate the memory compartments of exposed subjects", JEM, 202(5):673-685 (2005).
Taylor-Weidman, et al., "Induction of Endogenous Human Cytomegalovirus Gene Expression after Differentiation of Monocytes from Healthy Carriers", J. of Virol., 68(3): 1597-1604 (1994).
Tothova, et al., "FoxOs are Critical Mediators of Hematopoietic Stem Cell Resistance to Physiologic Oxidative Stress", Cell, 128(2):325-339 (2007).
Umashankar, et al., "A Novel Human Cytomegalovirus Locus Modulates Cell Type-Specific Outcomes of Infection", PLOS Pathogens, 7(12): e1002444 (2011).
Umashankar, et al., "Antagonistic determinants controlling replicative and latent states of human cytomegalovirus infection", Journal of Virology, 88:5987-6002 (2014b).
Umashankar, et al., "Hematopoietic long-term culture (hLTC) for human cytomegalovirus latency and reactivation", Methods Mol Biol, 1119:99-112 (2014a).
Wakeman, et al., "Identification of Alternative Transcripts Encoding the Essential Murine Gammaherpesvirus Lytic Transactivator RTA", J. of Virology, 88(10): 5474-5490 (2014).
Wakeman, et al., "Identification of Novel Kaposi's Sarcoma-Associated Herpesvirus Orf50 Transcripts: Discovery of New RTA Isoforms with Variable Transactivation Potential", J. of Virology, 91(1)::e01434-16, 23 pages (2017).
Wang, et al., "Cytomegalovirus Infection and the Risk of Mortality and Frailty in Older Women: A Prospective Observational Cohort Study", Am. J. of Epidemiology, 171(10): 1144-1152 (2010).
Wang, et al., "The ULb' region of the human cytomegalovirus genome confers an increased requirement for the viral protein kinase UL97", Journal of Virology, 87:6359-6376 (2013).
Weinshenker, et al., "Phorbol ester-induced differentiation permits productive human cytomegalovirus infection in a monocytic cell line", J. Immunol., 140:1625-31 (1988).
Yam, et al., "Design of HIV Vectors for Efficient Gene Delivery into Human Hematopoietic Cells", Mol. Therapy, 5(4): 479-484 (2002).
Zheng, et al., "Reprogramming of histone methylation controls the differentiation of monocytes into macrophages", The FEBS Journal, 284: 1309-1323 (2017).
Zhu, et al., "FoxO4 inhibits atherosclerosis through its function in bone marrow derived cells", Atherosclerosis, 219(2):492-498 (2011).
Ziehr, et al., "Human Cytomegalovirus pTRS1 and pIRS1 Antagonize Protein Kinase R to Facilitate Virus Replication", Journal of Virology, 90:3839-3848 (2016).
Ziehr, et al., "Human cytomegalovirus TRS1 protein associates with the 7-methylguanosine mRNA cap and facilitates translation", Proteomics, 15:1983-1994 (2015).
Choi, et al., "Hybrid HIV/MSCV LTR Enhances Transgene Expression of Lentiviral Vectors in Human CD34+ Hematopoietic Cells", Stem Cells, 19:236-246 (2001).

(56) References Cited

OTHER PUBLICATIONS

Chung, et al., "Analysis of Different Promoter Systems for Efficient Transgene Expression in Mouse Embryonic Stem Cell Lines", Stem Cells, 20(2): 139-145 (2002).
Norrman, et al., "Quantitative Comparison of Constitutive Promoters in Human ES cells", PLoS One, 5(8):e12412, 10 pages (2010).
Sirven, et al., "Enhanced Transgene Expression in Cord Blood CD341-Derived Hematopoietic Cells, Including Developing T Cells and NOD/SCID Mouse Repopulating Cells, Following Transduction with Modified TRIP Lentiviral Vectors", Mol. Ther., 4(3):438-448 (2001).
Tolmachov, et al., "Silencing of Transgene Expression: A Gene Therapy Perspective", Gene Therapy—Tools and Potential Applications, 3:50-68 (2013).
Wang, et al., "Promoter-Dependent Enhanced Green Fluorescent Protein Expression During Embryonic Stem Cell Propagation and Differentiation", Stem Cells and Development, 17:27-289 (2008).

* cited by examiner

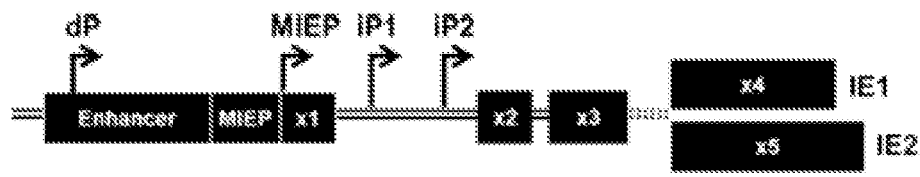
FIG. 3A
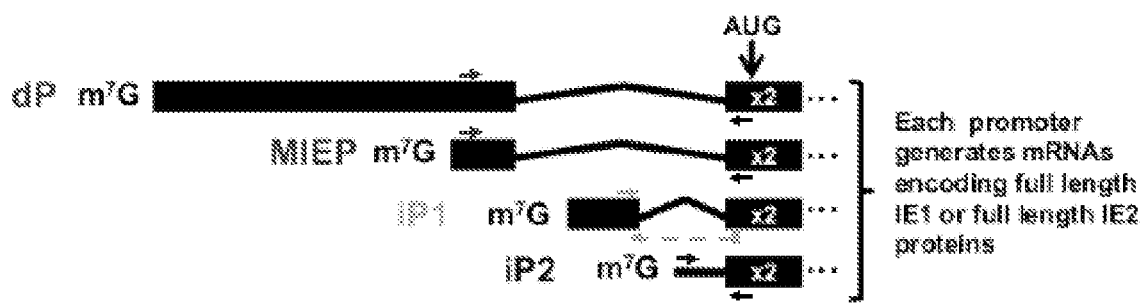
FIG. 3B
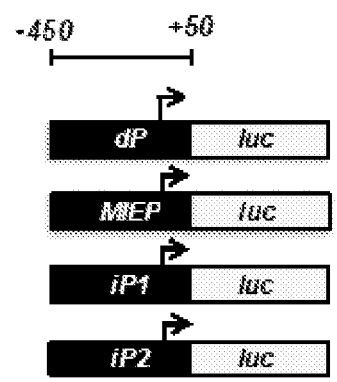 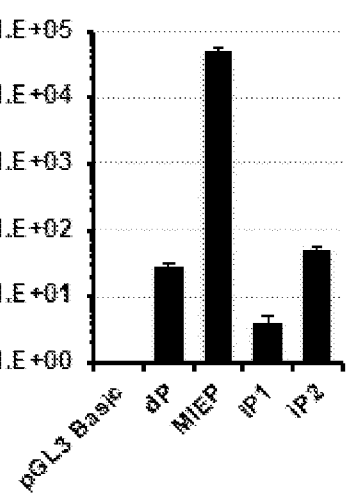
FIG. 4A                FIG. 4B

```
TB40E WT virus   GTAAGTACCGCCTATAGACTCTATAGGCCCACCCCCTTGGCTTCTTATGCATGCTATACTGTTTTTGGCTTGGGGTCTATA
ΔiP1             GTAAGTACCGCCTATAGACTCTATAGGCCCAtaacttcgtatagcatacattata-----------------------------
ΔiP2             GTAAGTACCGCCTATAGACTCTATAGGCCCACCCCCTTGGCTTCTTATGCATGCTATACTGTTTTTGGCTTGGGGTCTATA
ΔiP(1+2)         GTAAGTACCGCCTATAGACTCTATAGGCCCAtaacttcgtatagcatacattatacgaagttat--------------------

CACCCCCGCTTCCTTATGCTATAGGTGATGGTATAGCTTAGCCTATAGGTGTGGGTTATTGACCATTATTGACCACTCCCTATTGGTGACGATACTT
-----------------------------------------------------------------------------------------------
CACCCCCGCTTCCTTATGCTATAGGTGATGGTATAGCTTAGCCTATAGGTGTGGGTTATTGACCATTATTGACCACTCCCTATTGGTGACGATACTT
-----------------------------------------------------------------------------------------------

TCCATTACTAATCCATAACATGGCTCTTTGCCACAACTCTCTTTATTGGCTATATGCCAATACTCTGTCCTTCAGAGACTGACACGGACTCTGTATTTT
-----------------------------------------------------------------------------------------------
TCCATTACTAATCCATAACATGGCTCTTTGCCACAACTCTCTTTATTGGCTATATGCCAATACTCTGTCCTTCAGAGACTGACACGGACTCTGTATTTT
-----------------------------------------------------------------------------------------------

TACAGGATGGGGTCCCATTTATTATTTACAAATTCACATATACAACAACACCGTCCCCAGTACCCGCAGTTTTTATTAAACATAGCGTGGGATCTCCA
-------------------------------------------------------------------CGaAG- TTaT- TTAAACATAGCGTGGGATCTCCA
TACAGGATGGGGTCCCATTTATTATTTACAAATTCACATATACAACAACACCGTCCCCAGTACCCGataacttcgtatagcatacattatacgaagttat---------

CGCGAATCTCGGGTACGTGTTCCGGACATGGGCTCTTCTCCGGTAGCGGCGGAGCTTCTACATCCGAGCCCTGCTCCCATGCCTCCAGCGGCTCAT
CGCGAATCTCGGGTACGTGTTCCGGACATGGGCTCTTCTCCGGTAGCGGCGGAGCTTCTACATCCGAGCCCTGCTCCCATGCCTCCAGCGGCTCAT
-----------------------------------------------------------------------------------------------
-----------------------------------------------------------------------------------------------

GGTCGCTTGGCAGCTCCTTGCTCCTAACAGTGGAGGCCAGACTTAGGCACAGCACGATGCCCACCACCACCAGTGTGCCGCACAAGGCCGTGGCG
GGTCGCTTGGCAGCTCCTTGCTCCTAACAGTGGAGGCCAGACTTAGGCACAGCACGATGCCCACCACCACCAGTGTGCCGCACAAGGCCGTGGCG
-----------------------------------------------------------------------------------------------
-----------------------------------------------------------------------------------------------

GTAGGGTATGTGTCTGAAAATGAGCTCGGGGAGCGGGCTTGCACCGCTGACGCATTTGGAAGACTTAAGGCAGCGGCAGAAGAAGATGCAGGCA
GTAGGGTATGTGTCTGAAAATGAGCTCGGGGAGCGGGCTTGCACCGCTGACGCATTTGGAAGACTTAAGGCAGCGGCAGAAGAAGATGCAGGCA
-----------------------------------------------------------------------------------------------
-----------------------------------------------------------------------------------------------

GCTGAGTTGTTGTGTTCTGATAAGAGTCAGAGGTAACTCCCGTTGCGGTGCTGTTAACGGTGGAGGGCAGTGTAGTCTGAGCAGTACTCGTTGCTG
GCTGAGTTGTTGTGTTCTGATAAGAGTCAGAGGTAACTCCCGTTGCGGTGCTGTTAACGGTGGAGGGCAGTGTAGTCTGAGCAGTACTCGTTGCTG
---------------------------------------------------------------------------------------------CTG
---------------------------------------------------------------------------------------------CTG

CCGCGCGCGCCACCAGACATAATAGCTGACAGACTAACAGACTGTTCCTTTCCATGGGTCTTTTCTGCAG (SEQ ID NO:1)
CCGCGCGCGCCACCAGACATAATAGCTGACAGACTAACAGACTGTTCCTTTCCATGGGTCTTTTCTGCAG (SEQ ID NO:7)
CCGCGCGCGCCACCAGACATAATAGCTGACAGACTAACAGACTGTTCCTTTCCATGGGTCTTTTCTGCAG (SEQ ID NO:8)
CCGCGCGCGCCACCAGACATAATAGCTGACAGACTAACAGACTGTTCCTTTCCATGGGTCTTTTCTGCAG (SEQ ID NO:9)
```

FIG. 11A

```
TB40E WT virus      GTAAGTACCGCCTATAGACTCTATAGGCCCACCCCCTTGGCTTCTTATGCATGCTATACTGTTTTTGGCTTGGGGTCTATA
ΔiP1 (w/o LoxP)     GTAAGTACCGCCTATAGACTCTATAGGCCCA-------------------------------------------------
ΔiP2 (w/o LoxP)     GTAAGTACCGCCTATAGACTCTATAGGCCCACCCCCTTGGCTTCTTATGCATGCTATACTGTTTTTGGCTTGGGGTCTATA
ΔiP(1+2) (w/o LoxP) GTAAGTACCGCCTATAGACTCTATAGGCCCA-------------------------------------------------

CACCCCCGCTTCCTTATGCTATAGGTGATGGTATAGCTTAGCCTATAGGTGTGGGTTATTGACCATTATTGACCACTCCCCTATTGGTGACGATACTT
--------------------------------------------------------------------------------------------------
CACCCCCGCTTCCTTATGCTATAGGTGATGGTATAGCTTAGCCTATAGGTGTGGGTTATTGACCATTATTGACCACTCCCCTATTGGTGACGATACTT
--------------------------------------------------------------------------------------------------

TCCATTACTAATCCATAACATGGCTCTTTGCCACAACTCTCTTTATTGGCTATATGCCAATACTCTGTCCTTCAGAGACTGACACGGACTCTGTATTTT
--------------------------------------------------------------------------------------------------
TCCATTACTAATCCATAACATGGCTCTTTGCCACAACTCTCTTTATTGGCTATATGCCAATACTCTGTCCTTCAGAGACTGACACGGACTCTGTATTTT
--------------------------------------------------------------------------------------------------

TACAGGATGGGGTCCCATTTATTATTTACAAATTCACATATACAACAACACCGTCCCCAGTACCCGCAGTTTTTATTAAACATAGCGTGGGATCTCCA
-------------------------------------------------------------------------TTAAACATAGCGTGGGATCTCCA
TACAGGATGGGGTCCCATTTATTATTTACAAATTCACATATACAACAACACCGTCCCCAGTACCCG--------------------------------
--------------------------------------------------------------------------------------------------

CGCGAATCTCGGGTACGTGTTCCGGACATGGGCTCTTCTCCGGTAGCGGCGGAGCTTCTACATCCGAGCCCTGCTCCCATGCCTCCAGCGGCTCAT
CGCGAATCTCGGGTACGTGTTCCGGACATGGGCTCTTCTCCGGTAGCGGCGGAGCTTCTACATCCGAGCCCTGCTCCCATGCCTCCAGCGGCTCAT
--------------------------------------------------------------------------------------------------
--------------------------------------------------------------------------------------------------

GGTCGCTTGGCAGCTCCTTGCTCCTAACAGTGGAGGCCAGACTTAGGCACAGCACGATGCCCACCACCACCAGTGTGCCGCACAAGGCCGTGGCG
GGTCGCTTGGCAGCTCCTTGCTCCTAACAGTGGAGGCCAGACTTAGGCACAGCACGATGCCCACCACCACCAGTGTGCCGCACAAGGCCGTGGCG
--------------------------------------------------------------------------------------------------
--------------------------------------------------------------------------------------------------

GTAGGGTATGTGTCTGAAAATGAGCTCGGGGAGCGGGCTTGCACCGCTGACGCATTTGGAAGACTTAAGGCAGCGGCAGAAGAAGATGCAGGCA
GTAGGGTATGTGTCTGAAAATGAGCTCGGGGAGCGGGCTTGCACCGCTGACGCATTTGGAAGACTTAAGGCAGCGGCAGAAGAAGATGCAGGCA
--------------------------------------------------------------------------------------------------
--------------------------------------------------------------------------------------------------

GCTGAGTTGTTGTGTTCTGATAAGAGTCAGAGGTAACTCCCGTTGCGGTGCTGTTAACGGTGGAGGGCAGTGTAGTCTGAGCAGTACTCGTTGCTG
GCTGAGTTGTTGTGTTCTGATAAGAGTCAGAGGTAACTCCCGTTGCGGTGCTGTTAACGGTGGAGGGCAGTGTAGTCTGAGCAGTACTCGTTGCTG
---------------------------------------------------------------------------------------------CTG
---------------------------------------------------------------------------------------------CTG

CCGCGCGCGCCACCAGACATAATAGCTGACAGACTAACAGACTGTTCCTTTCCATGGGTCTTTTCTGCAG (SEQ ID NO:1)
CCGCGCGCGCCACCAGACATAATAGCTGACAGACTAACAGACTGTTCCTTTCCATGGGTCTTTTCTGCAG (SEQ ID NO:10)
CCGCGCGCGCCACCAGACATAATAGCTGACAGACTAACAGACTGTTCCTTTCCATGGGTCTTTTCTGCAG (SEQ ID NO:11)
CCGCGCGCGCCACCAGACATAATAGCTGACAGACTAACAGACTGTTCCTTTCCATGGGTCTTTTCTGCAG (SEQ ID NO:12)
```

FIG. 11B

```
                 900       910       920       930       940
IE_map_in_TB40ATTCCCCGTGCCAAGAGTGAC GTAAGTACCGCCTATAGACTC
              ~~~~~~~~~~~~~~~~~~~~~~~~~~~~~~~~~~~~~~~~~~~
Consensus:    .............................................
              ~~~~~~~~~~~~~~~~~~~~~~~~~~~~~~~~~~~~~~~~~~~
AD169 Bradley ........................................G..
Merlyn Dolan  .............................................
Towne Bradley .............................................

1000      1010      1020      1030      1040
IE_map_in_TB40 TACACCCCCGCTTCCTTATGCTATAGGTGATGGTATAGCTTA
               ~~~~~~~~~~~~~~~~~~~~~~~~~~~~~~~~~~~~~~~~~~
Consensus:     ..........................................
               ~~~~~~~~~~~~~~~~~~~~~~~~~~~~~~~~~~~~~~~~~~
AD169 Bradley  ................C...T.....................
Merlyn Dolan   ..........................................
Towne Bradley  ..........................................

1100      1110      1120      1130      1140
IE_map_in_TB40 TCCATTACTAATCCATAACATGGCTCTTTGCCACAACTCTCT
               ~~~~~~~~~~~~~~~~~~~~~~~~~~~~~~~~~~~~~~~~~~
Consensus:     ..........................................
               ~~~~~~~~~~~~~~~~~~~~~~~~~~~~~~~~~~~~~~~~~~
AD169 Bradley  ..........................................
Merlyn Dolan   ..........................................
Towne Bradley  ....................................A...
```

| FIG. 12 | FIG. 12 (CONT.) |
| --- | --- |
| FIG. 12 (CONT. 2) | FIG. 12 (CONT. 3) |
| FIG. 12 (CONT. 4) | FIG. 12 (CONT. 5) |

```
                                950       960       970       980       990
                         TATAGGCCCACCCCCTTGGCTTCTTATGCATGCTATACTGTTTTTGGCTTGGGGTCTA
                         ~~~~~~~~~~~~~~~~~~~~~~~~~~~~~~~~~~~~~~~~~~~~~~~~~~~~~~~~~~
                         ..........................................................
                         ~~~~~~~~~~~~~~~~~~~~~~~~~~~~~~~~~~~~~~~~~~~~~~~~~~~~~~~~~~
                         ..........................................................
                         ..........................................................
                         .......A......T.....-....................................C...

1050      1060      1070      1080      1090
FROM FIG. 12             GCCTATAGGTGTGGGTTATTGACCATTATTGACCACTCCCCTATTGGTGACGATACTT
                         ~~~~~~~~~~~~~~~~~~~~~~~~~~~~~~~~~~~~~~~~~~~~~~~~~~~~~~~~~~
                         ..........................................................
                         ~~~~~~~~~~~~~~~~~~~~~~~~~~~~~~~~~~~~~~~~~~~~~~~~~~~~~~~~~~
                         ..........................................................
                         .........................................T.........G........
                         ..........................................................

1150      1160      1170      1180      1190
                         TTATTGGCTATATGCCAATACTCTGTCCTTCAGAGACTGACACGGACTCTGTATTTTT
                         ~~~~~~~~~~~~~~~~~~~~~~~~~~~~~~~~~~~~~~~~~~~~~~~~~~~~~~~~~~
                         ..........................................................
                         ~~~~~~~~~~~~~~~~~~~~~~~~~~~~~~~~~~~~~~~~~~~~~~~~~~~~~~~~~~
                         ...................A......................................
                         ..........................................................
                         C.........................................................
                                                            ↓ TO FIG. 12 (CONT. 3)
```

| FIG. 12 | FIG. 12 (CONT.) |
|---|---|
| FIG. 12 (CONT. 2) | FIG. 12 (CONT. 3) |
| FIG. 12 (CONT. 4) | FIG. 12 (CONT. 5) |

FIG. 12 (CONT.)

↓FROM FIG. 12

```
              1200       1210       1220       1230       1240
IE_map_in_TB40 ACAGGATGGGGTCCCATTTATTATTTACAAATTCACATATAC Consensus:     ..........................................

AD169 Bradley  ..............T...........................
Merlyn Dolan   ..........................................
Towne Bradley  ..........................................

1300       1310       1320       1330       1340
IE_map_in_TB40 GAATCTCGGGTACGTGTTCCGGACATGGGCTCTTCTCCGGTA      TO FIG. 12 (CONT. 3) →

Consensus:     ..........................................

AD169 Bradley  ..........................................
Merlyn Dolan   ..........................................
Towne Bradley  ..........................................

1400       1410       1420       1430       1440
IE_map_in_TB40 TGGCAGCTCCTTGCTCCTAACAGTGGAGGCCAGACTTAGGCA Consensus:     C.........................................

AD169 Bradley  C.........................................
Merlyn Dolan   C.........................................
Towne Bradley  C.........................................
                                              ↓TO FIG. 12 (CONT. 5)
```

| FIG. 12 | FIG. 12 (CONT.) |
| FIG. 12 (CONT. 2) | FIG. 12 (CONT. 3) |
| FIG. 12 (CONT. 4) | FIG. 12 (CONT. 5) |

*FIG. 12*
*(CONT. 2)*

```
                              ↓ FROM FIG. 12 (CONT.)
      1250      1260      1270      1280      1290
    ┌────────────────────────────────────────────────────┐
    │AACAACACCGTCCCCAGTACCCGCAGTTTTTATTAAACATAGCGTGGGATCTCCACGC│
    └────────────────────────────────────────────────────┘
    ~~~~~~~~~~~~~~~~~~~~~~~~~~~~~~~~~~~~~~~~~~~~~~~~~~~~~~~~
    .................G........................................
    ~~~~~~~~~~~~~~~~~~~~~~~~~~~~~~~~~~~~~~~~~~~~~~~~~~~~~~~~
    ....C............G.......................A...............
    ..........................................................
    ......G........C..G.......................................

1350      1360      1370      1380      1390
    ┌────────────────────────────────────────────────────┐
    │GCGGCGGAGCTTCTACATCCGAGCCCTGCTCCCATGCCTCCAGCGGCTCATGGTCGCT│
    └────────────────────────────────────────────────────┘
    ~~~~~~~~~~~~~~~~~~~~~~~~~~~~~~~~~~~~~~~~~~~~~~~~~~~~~~~~
    ..............C...........................................
    ~~~~~~~~~~~~~~~~~~~~~~~~~~~~~~~~~~~~~~~~~~~~~~~~~~~~~~~~
    ...........................................A.............
    ..............C...........................................
    ..............C..............G............................

1450      1460      1470      1480      1490
    ┌────────────────────────────────────────────────────┐
    │CAGCACGATGCCCACCACCACCAGTGTGCCGCACAAGGCCGTGGCGGTAGGGTATGTG│
    └────────────────────────────────────────────────────┘
    ~~~~~~~~~~~~~~~~~~~~~~~~~~~~~~~~~~~~~~~~~~~~~~~~~~~~~~~~
    ..........................................................
    ~~~~~~~~~~~~~~~~~~~~~~~~~~~~~~~~~~~~~~~~~~~~~~~~~~~~~~~~
    ..........................................................
    ..........................................................
    ......A...................................................
                              ↓ TO FIG. 12 (CONT. 5)
```

| FIG. 12 | FIG. 12 (CONT.) |
|---|---|
| FIG. 12 (CONT. 2) | FIG. 12 (CONT. 3) |
| FIG. 12 (CONT. 4) | FIG. 12 (CONT. 5) |

FROM FIG. 12 (CONT. 2) →

FIG. 12 (CONT. 3)

↓ FROM FIG. 12 (CONT. 2)

```
              1500      1510      1520      1530      1540
IE_map_in_TB40 TCTGAAAATGAGCTCGGGGAGCGGGCTTGCACCGCTGACGCA Consensus:     .....................NT..................

AD169 Bradley  ..........................................
Merlyn Dolan   .....................AT..................
Towne Bradley  .................A..TT.....C.............

1600      1610      1620      1630      1640
IE_map_in_TB40 GATAAGAGTCAGAGGTAACTCCCGTTGCGGTGCTGTTAACGG Consensus:     ..........................................

AD169 Bradley  ..........................................
Merlyn Dolan   .T.G...................T..................
Towne Bradley  ..........................................

1700      1710      1720      1730      1740
IE_map_in_TB40 TAGCTGACAGACTAACAGACTGTTCCTTTCCATGGGTCTTTT Consensus:     ..........................................

AD169 Bradley  ..........................................
Merlyn Dolan   ................................A..C.....
Towne Bradley  ..........................................
```

TO FIG. 12 (CONT. 5) →

| FIG. 12 | FIG. 12 (CONT.) |
| FIG. 12 (CONT. 2) | FIG. 12 (CONT. 3) |
| FIG. 12 (CONT. 4) | FIG. 12 (CONT. 5) |

*FIG. 12*
*(CONT. 4)*

| FROM FIG. 12 (CONT. 3)

```
            1550      1560      1570      1580      1590
    TTTGGAAGACTTAAGGCAGCGGCAGAAGAAGATGCAGGCAGCTGAGTTGTTGTGTTCT
    ~~~~~~~~~~~~~~~~~~~~~~~~~~~~~~~~~~~~~~~~~~~~~~~~~~~~~~~~~~
    GA........................................................
    ~~~~~~~~~~~~~~~~~~~~~~~~~~~~~~~~~~~~~~~~~~~~~~~~~~~~~~~~~~
    ..........................................................
    GA..................A.......-.-.-................---........
    GA.....................................................A....
```

FROM FIG. 12 (CONT. 4) →

```
            1650      1660      1670      1680      1690
    TGGAGGGCAGTGTAGTCTGAGCAGTACTCGTTGCTGCCGCGCGCGCCACCAGACATAA
    ~~~~~~~~~~~~~~~~~~~~~~~~~~~~~~~~~~~~~~~~~~~~~~~~~~~~~~~~~
    .........................................................
    ~~~~~~~~~~~~~~~~~~~~~~~~~~~~~~~~~~~~~~~~~~~~~~~~~~~~~~~~~
    .........................................................
    .........................................................
    .........................................................
```

| FIG. 12 | FIG. 12 (CONT.) |
|---|---|
| FIG. 12 (CONT. 2) | FIG. 12 (CONT. 3) |
| FIG. 12 (CONT. 4) | FIG. 12 (CONT. 5) |

```
            1750      1760      1770      1780      1790
    CTGCAGTCACCGTCCTTGACACGATGGAGTCCTCTGCCAAGAGAAAGATGGACCCTGA
    ~~~~~~~~~~~~~~~~~~~~~~~~~~~~~~~~~~~~~~~~~~~~~~~~~~~~~~~~~
    .........................................................
    ~~~~~~~~~~~~~~~~~~~~~~~~~~~~~~~~~~~~~~~~~~~~~~~~~~~~~~~~~
    .........................................................
    .........................................................
    .........................................................
```

FIG. 12
(CONT. 5)

```
                                        910       920       930
IE_map_in_TB40E                   TCCCCGTGCCAAGAGTGAC|GTAAGTACCGCCTA|
                                  ~~~~~~~~~~~~~~~~~~~~~~~~~~~~~~~~~~

Consensus:                        ..................................
                                  ~~~~~~~~~~~~~~~~~~~~~~~~~~~~~~~~~~

BAC 120 TB40E5 IE intron A deleted  ....................
BAC 85 TB40E-5 dIP1 floxed BAC      ....................
BAC 86 TB40E5 dIP2 final            ....................
BAC 87 TB40E5 dIP1+2 final          ....................

1010      1020      1030
IE_map_in_TB40E                   |CACCCCGCTTCCTTATGCTATAGGTGATGGTA|     TO FIG. 12 (CONT. 7)
                                  ~~~~~~~~~~~~~~~~~~~~~~~~~~~~~~~~~    ───────────▶

Consensus:                        ..................................
                                  ~~~~~~~~~~~~~~~~~~~~~~~~~~~~~~~~~~

BAC 120 TB40E5 IE intron A deleted
BAC 85 TB40E-5 dIP1 floxed BAC
BAC 86 TB40E5 dIP2 final
BAC 87 TB40E5 dIP1+2 final          ..............................

1110      1120      1130
IE_map_in_TB40E                   |CATTACTAATCCATAACATGGCTCTTTGCCACA|
                                  ~~~~~~~~~~~~~~~~~~~~~~~~~~~~~~~~~~

Consensus:                        ..................................
                                  ~~~~~~~~~~~~~~~~~~~~~~~~~~~~~~~~~~

BAC 120 TB40E5 IE intron A deleted
BAC 85 TB40E-5 dIP1 floxed BAC
BAC 86 TB40E5 dIP2 final
BAC 87 TB40E5 dIP1+2 final          ..............................

TO FIG. 12 (CONT. 8)
                                  ▼
```

| FIG. 12 (CONT. 6) | FIG. 12 (CONT. 7) |
| --- | --- |
| FIG. 12 (CONT. 8) | FIG. 12 (CONT. 9) |
| FIG. 12 (CONT. 10) | FIG. 12 (CONT. 11) |

FIG. 12 (CONT. 6)

```
         940       950       960       970       980       990      1000
.TAGACTCTATAGGCCCACCCCCTTGGCTTCTTATGCATGCTATACTGTTTTTGGCTTGGGGTCTATA
~~~~~~~~~~~~~~~~~~~~~~~~~~~~~~~~~~~~~~~~~~~~~~~~~~~~~~~~~~~~~~~~~~
..................................................................
~~~~~~~~~~~~~~~~~~~~~~~~~~~~~~~~~~~~~~~~~~~~~~~~~~~~~~~~~~~~~~~~~~

................taacttcgtatagcatacattata
..................................................................
................taacttcgtatagcatacattatacgaagttat
```

FROM FIG. 12 (CONT. 6) →

```
        1040      1050      1360      1070      1080      1090      1100
TAGCTTAGCCTATAGGTGTGGGTTATTGACCATTATTGACCACTCCCCTATTGGTGACGATACTTTC
~~~~~~~~~~~~~~~~~~~~~~~~~~~~~~~~~~~~~~~~~~~~~~~~~~~~~~~~~~~~~~~~~~
..................................................................
~~~~~~~~~~~~~~~~~~~~~~~~~~~~~~~~~~~~~~~~~~~~~~~~~~~~~~~~~~~~~~~~~~
```

| FIG. 12 (CONT. 6) | FIG. 12 (CONT. 7) |
|---|---|
| FIG. 12 (CONT. 8) | FIG. 12 (CONT. 9) |
| FIG. 12 (CONT. 10) | FIG. 12 (CONT. 11) |

```
..................................................................

1140      1150      1160      1170      1180      1190      1200
ACTCTCTTTATTGGCTATATGCCAATACTCTGTCCTTCAGAGACTGACACGGACTCTGTATTTTTAC
~~~~~~~~~~~~~~~~~~~~~~~~~~~~~~~~~~~~~~~~~~~~~~~~~~~~~~~~~~~~~~~~~~
..................................................................
~~~~~~~~~~~~~~~~~~~~~~~~~~~~~~~~~~~~~~~~~~~~~~~~~~~~~~~~~~~~~~~~~~
```

FROM FIG. 12 (CONT. 6)

```
                      1210      1220      1230
IE_map_in_TB40E    AGGATGGGGTCCCATTTATTATTTACAAATTCA
```

Consensus:

BAC 120 TB40E5 IE intron A deleted
BAC 85 TB40E-5 dIP1 floxed BAC
BAC 86 TB40E5 dIP2 final
BAC 87 TB40E5 dIP1+2 final

```
                      1310      1320      1330
IE_map_in_TB40E    ATCTCGGGTACGTGTTCCGGACATGGGCTCTTC
```

TO FIG. 12 (CONT. 9)

Consensus:

BAC 120 TB40E5 IE intron A deleted
BAC 85 TB40E-5 dIP1 floxed BAC
BAC 86 TB40E5 dIP2 final
BAC 87 TB40E5 dIP1+2 final

```
                      1410      1420      1430
IE_map_in_TB40E    GCAGCTCCTTGCTCCTAACAGTGGAGGCCAGAC
```

Consensus:

BAC 120 TB40E5 IE intron A deleted
BAC 85 TB40E-5 dIP1 floxed BAC
BAC 86 TB40E5 dIP2 final
BAC 87 TB40E5 dIP1+2 final

TO FIG. 12 (CONT. 10)

| FIG. 12 (CONT. 6) | FIG. 12 (CONT. 7) |
| --- | --- |
| FIG. 12 (CONT. 8) | FIG. 12 (CONT. 9) |
| FIG. 12 (CONT. 10) | FIG. 12 (CONT. 11) |

*FIG. 12 (CONT. 8)*

```
                              ↓ FROM FIG. 12 (CONT. 7)
          1240      1250      1260      1270      1280      1290      1300
      CATATACAACAACACCGTCCCCAGTACCCGCAGTTTTTATTAAACATAGCGTGGGATCTCCACGCGA
      ~~~~~~~~~~~~~~~~~~~~~~~~~~~~~~~~~~~~~~~~~~~~~~~~~~~~~~~~~~~~~~~~~~
      ............................A..-..A.-............................
      ~~~~~~~~~~~~~~~~~~~~~~~~~~~~~~~~~~~~~~~~~~~~~~~~~~~~~~~~~~~~~~~~~~

..A..-..A.-............................
                         ............ataacttcgtatagcatacattatacgaagttat FROM FIG. 12 (CONT. 8)   1340      1350      1360      1370      1380      1390      1400
    ──────────►       TCCGGTAGCGGCGGAGCTTCTACATCCGAGCCCTGCTCCCATGCCTCCAGCGGCTCATGGTCGCTTG
                      ~~~~~~~~~~~~~~~~~~~~~~~~~~~~~~~~~~~~~~~~~~~~~~~~~~~~~~~~~~~~~~~~~~~
                      ...................................................................
                      ~~~~~~~~~~~~~~~~~~~~~~~~~~~~~~~~~~~~~~~~~~~~~~~~~~~~~~~~~~~~~~~~~~~
```

| FIG. 12 (CONT. 6) | FIG. 12 (CONT. 7) |
|---|---|
| FIG. 12 (CONT. 8) | FIG. 12 (CONT. 9) |
| FIG. 12 (CONT. 10) | FIG. 12 (CONT. 11) |

```
                           ...................................................................

1440      1450      1460      1470      1480      1490      1500
                        TTAGGCACAGCACGATGCCCACCACCACCAGTGTGCCGCACAAGGCCGTGGCGGTAGGGTATGTGTC
                        ~~~~~~~~~~~~~~~~~~~~~~~~~~~~~~~~~~~~~~~~~~~~~~~~~~~~~~~~~~~~~~~~~~~
                        ...................................................................
                        ~~~~~~~~~~~~~~~~~~~~~~~~~~~~~~~~~~~~~~~~~~~~~~~~~~~~~~~~~~~~~~~~~~~
```

FROM FIG. 12 (CONT. 8)

```
                                1510       1520       1530
IE_map_in_TB40E                 TGAAAATGAGCTCGGGGAGCGGGCTTGCACCGC
```

Consensus:       ................................

BAC 120 TB40E5 IE intron A deleted
BAC 85 TB40E-5 dIP1 floxed BAC       ................................
BAC 86 TB40E5 dIP2 final
BAC 87 TB40E5 dIP1+2 final

TO FIG. 12 (CONT. 11) →

```
                                1610       1620       1630
IE_map_in_TB40E                 TAAGAGTCAGAGGTAACTCCCGTTGCGGTGCTG
```

Consensus:       ................................

BAC 120 TB40E5 IE intron A deleted
BAC 85 TB40E-5 dIP1 floxed BAC       ................................
BAC 86 TB40E5 dIP2 final
BAC 87 TB40E5 dIP1+2 final

```
                                1710       1720       1730
IE_map_in_TB40E                 GCTGACAGACTAACAGACTGTTCCTTTCCATGG
```

Consensus:       ................................

BAC 120 TB40E5 IE intron A deleted
BAC 85 TB40E-5 dIP1 floxed BAC       ................................
BAC 86 TB40E5 dIP2 final              ................................
BAC 87 TB40E5 dIP1+2 final            ................................

| FIG. 12 (CONT. 6) | FIG. 12 (CONT. 7) |
|---|---|
| FIG. 12 (CONT. 8) | FIG. 12 (CONT. 9) |
| FIG. 12 (CONT. 10) | FIG. 12 (CONT. 11) |

FIG. 12 (CONT. 10)

```
                                    | FROM FIG. 12 (CONT. 9)
                                    ↓
           1540      1550      1560      1570      1580      1590      1600
           TGACGCATTTGGAAGACTTAAGGCAGCGGCAGAAGAAGATGCAGGCAGCTGAGTTGTTGTGTTCTGA
           ~~~~~~~~~~~~~~~~~~~~~~~~~~~~~~~~~~~~~~~~~~~~~~~~~~~~~~~~~~~~~~~~~~
           ..................................................................
           ~~~~~~~~~~~~~~~~~~~~~~~~~~~~~~~~~~~~~~~~~~~~~~~~~~~~~~~~~~~~~~~~

..............................................................

FROM FIG. 12 (CONT. 10)
──────────────▶    1640      1650      1660      1670      1680      1690      1700
           TTAACGGTGGAGGGCAGTGTAGTCTGAGCAGTACTCGTTGCTGCCGCGCGCGCCACCAGACATAATA
           ~~~~~~~~~~~~~~~~~~~~~~~~~~~~~~~~~~~~~~~~~~~~~~~~~~~~~~~~~~~~~~~~~~
           ..................................................................
           ~~~~~~~~~~~~~~~~~~~~~~~~~~~~~~~~~~~~~~~~~~~~~~~~~~~~~~~~~~~~~~~~~~
```

| FIG. 12 (CONT. 6) | FIG. 12 (CONT. 7) |
|---|---|
| FIG. 12 (CONT. 8) | FIG. 12 (CONT. 9) |
| FIG. 12 (CONT. 10) | FIG. 12 (CONT. 11) |

*FIG. 12*
*(CONT. 11)*

```
                                  ..............................................
                                             ..................................
                                                ...............................
           1740      1750      1760      1770      1780      1790      1800
           GTCTTTTCTGCAGTCACCGTCCTTGACACGATGGAGTCCTCTGCCAAGAGAAAGATGGACCCTGACA
           ~~~~~~~~~~~~~~~~~~~~~~~~~~~~~~~~~~~~~~~~~~~~~~~~~~~~~~~~~~~~~~~~~~
           ..................................................................
           ~~~~~~~~~~~~~~~~~~~~~~~~~~~~~~~~~~~~~~~~~~~~~~~~~~~~~~~~~~~~~~~~~~
           ..................................................................
           ..................................................................
           ..................................................................
           ..................................................................
```

VIRAL PROMOTERS AND COMPOSITIONS AND METHODS OF USE THEREOF

CROSS-REFERENCE TO RELATED APPLICATIONS

This application is a National Phase application under 35 U.S.C. § 371 of International Application No. PCT/US2019/041000, filed on Jul. 9, 2019, which claims the benefit of and priority to U.S. Ser. No. 62/695,664, filed Jul. 9, 2018, each of which are specifically incorporated by reference herein in their entirety.

STATEMENT REGARDING FEDERALLY SPONSORED RESEARCH

This invention was made with government support under Grant Nos. AI079059, AI103311 and AI143191 awarded by National Institutes of Health. The government has certain rights in the invention.

REFERENCE TO SEQUENCE LISTING

The Sequence Listing submitted as a text file named "UA18_194_PCT_ST25.txt," created on Jul. 3, 2019, and having a size of 14,624 bytes is hereby incorporated by reference pursuant to 37 C.F.R § 1.52(e)(5).

FIELD OF THE INVENTION

This invention generally relates to viruses and promoters thereof, and compositions and methods of use thereof including for inducing an immune response to antigen(s) encoded by the viral genome.

BACKGROUND OF THE INVENTION

HCMV is a complex DNA virus and a member of the beta herpesvirus family that infects a majority of the world's population. While the infection is typically asymptomatic, HCMV poses a life-threatening disease risk in individuals with inadequate T cell immunity, as is the case in stem cell or solid organ transplantation, AIDS, and cancer patients undergoing intensive chemotherapy regimens (Boeckh, et al., *The Journal of clinical investigation*, 121, 1673-1680 (2011), Boeckh, M. et al., *Biol Blood Marrow Transplant*, 9, 543-558 (2003), Ariza-Heredia, et al., *Cancer Lett*, 342, 1-8 (2014), Razonable, et al., *American journal of transplantation: official journal of the American Society of Transplantation and the American Society of Transplant Surgeons*, 13 Suppl 4, 93-106 (2013)). Further, in the immune-naïve fetus, HCMV is the leading cause of birth defects resulting in mild to severe hearing loss and cognitive impairment (Cannon, et al., *Journal of clinical virology: the official publication of the Pan American Society for Clinical Virology*, 46 Suppl 4, S6-10 (2009)). The cost of asymptomatic persistence of the latent virus is poorly understood, but is emerging as a risk factor for age-related pathologies including vascular disease (Melnick, et al., *Archivum immunologiae et therapias experimentalis*, 44, 297-302 (1996), Koskinen, et al., *The Journal of heart and lung transplantation: the official publication of the International Society for Heart Transplantation*, 12, 724-729 (1993), Streblow, et al., *Current topics in microbiology and immunology*, 325, 397-415 (2008)), immune dysfunction (Sylwester, et al., *The Journal of experimental medicine*, 202, 673-685 (2005), Cicin-Sain, et al., *PLoS pathogens*, 8, e1002849 (2012)), and frailty (Schmaltz, et al., *Journal of the American Geriatrics Society*, 53, 747-754 (2005), Wang, et al., *Am J Epidemiol*, 171, 1144-1152 (2010), High, et al., *Journal of the American Geriatrics Society*, 53, 906-908 (2005)). The virus has been assigned the highest priority for vaccine development by the National Vaccine Advisory Committee (Arvin, et al., *Clin Infect Dis*, 39, 233-239 (2004)). Currently, there is no vaccine, and current antivirals have significant toxicity and fail to target latent infection.

Thus, it is object of the invention to provide safer viruses, and composition and methods of use thereof.

It is another object of the invention to provide compositions and methods of gene therapy, particularly in hematopoietic cells.

SUMMARY OF THE INVENTION

Viruses with impaired ability to reactivate from latency, and pharmaceutical compositions and method of use thereof are provided. The genomes of the viruses include one or more mutations that reduce expression from one or more promoters that regulate expression of viral genes during reactivation from latency. The mutation(s) are typically in a region of the viral genome that includes (i) promoter elements of the iP1 promoter of human cytomegalovirus (HCMV), or the sequence of another virus corresponding thereto (e.g., an iP1 promoter homolog); (ii) promoter elements of the iP2 promoter of human cytomegalovirus (HCMV), or sequence of another virus corresponding thereto (e.g., an iP2 promoter homolog); or (iii) a combination thereof. The homolog can be an orthologue or a paralogue. For example, in some embodiments, the virus is another herpesvirus such as herpes simplex virus 1, herpes simplex virus 2, varicella-zoster virus, Epstein-Barr virus, human herpesvirus 6A, human herpesvirus 6B, human herpesvirus 7, and Kaposi's sarcoma-associated herpesvirus. In other embodiments, the virus is another CMV, such as murine or rhesus CMV.

The mutation(s) can be substitution, deletion, insertion, or a combination thereof, of one or more nucleotides. The mutation(s) can reduce the ability of one or more transcription factors to bind to or otherwise activate expression from the promoter. In some embodiments, the transcription factor is a FOXO transcription factor. In some embodiments, the mutation(s) is in a region of the viral genome including the sequence of any one of SEQ ID NO:1-6 or a fragment thereof, or a sequence with at least 60, 70, 80, 85, 90, 95, 96, 97, 98, or 99% sequence identity to any one of SEQ ID NO:1-6, or a reverse complement of any of the foregoing. In particular embodiments, the mutation is deletion of all or a functional fragment of any one of SEQ ID NO:1-6, or a sequence homologous thereto, or a reverse complement of any of the foregoing.

In some embodiments, the virus further includes one or more mutations in one or more genes important for viral tropism, one or more genes important for infection, one or more genes important for replication, one or more additional genes important for reactivation, one or more genes important for encoding an immunomodulatory protein, or a combination thereof.

In some embodiments, the viral genome further includes an expression control sequence operably linked to a sequence encoding a heterologous antigen. The virus can encode two, three, four, or more such heterologous antigens. The heterologous antigens can be derived from, for example, a bacteria, virus, parasite, or cancer.

Pharmaceutical compositions are also provided. The pharmaceutical compositions typically include an effective amount of a virus to induce an immune response in subject in need thereof when administered to the subject. The pharmaceutical compositions can include additional agents, for example adjuvants to enhance the immune response. In some embodiments, the virus does not encode a heterologous antigen, and the immune response is limited to the virus itself (e.g., autologous antigen(s)). In some embodiments, wherein the virus encodes one or more heterologous antigens, the immune response can be against the heterologous antigen(s) in addition or alternative to autologous antigen(s).

Methods of treating a subject in need thereof by administering the pharmaceutical composition to the subject are also provided. The methods can be vaccine protocols. Thus, in some embodiments, the subject is administered the composition to provide prophylactic or therapeutic protection against the virus itself (e.g., autologous antigen(s)) alone or in combination with protection against an infection from another virus, bacteria, parasite, or cancer (e.g., heterologous antigen(s)). In some embodiments, the subject is administered two or more different viruses to induce protection against a myriad of different antigens. The two or more viruses can be in the same or different pharmaceutical compositions and can be administered at the same or different times.

Viral promoters, compositions, and methods of use thereof are also provided. For example, nucleic acids including the promoter elements of the iP1 promoter or a homolog thereof, the iP2 promoter or a homolog thereof, or a combination thereof operably linked to a heterologous transgene are provided. Typically the transgene is heterologous to the promoter sequence. Nucleic acids including the sequence of any one of SEQ ID NO:1-6 or a functional fragment thereof or a variant thereof comprising at least 80% sequence identity to SEQ ID NOS:1-6 operably linked to a heterologous transgene are also provided.

The nucleic acids further include one or more additional expression control sequences. The nucleic acid is incorporated into the genome of the cell and/or an extrachromosomal vector such as a plasmid or viral vector. The transgene can encode, for example, a therapeutic protein, a functional nucleic acid, or a gene editing molecule.

The nucleic acids can be transformed or transfected or otherwise introduced into cells. Thus, cells transformed, transfected, or engineered with the disclosed nucleic acids are provided. In some embodiments, the promoter is incorporated into a genome or a extrachromosomal vector and expresses a transgene introduced into the cells with the promoter. In some embodiments, the promoter alone is incorporated into a cell's genome to drive expression of an endogenous gene.

In the most preferred embodiments, the cells are hematopoietic cells, for example, hematopoietic stem cells or progenitor cells. Compositions including a plurality of cells, e.g., hematopoietic cells, expressing a gene under the control of the disclosed promoters are also provided.

Methods of treating a subject in need thereof by administering the nucleic acid, or cells harboring the nucleic acids are also provided. In an exemplary embodiments, the subject has a genetic disease or disorder and the cells are administered in an effective amount to treat the disease or disorder.

BRIEF DESCRIPTION OF THE DRAWINGS

FIGS. 3A and 3B are schematics of MIE locus promoters (3A) and the 5' ends up to and including exon 2 of IE-encoding transcripts derived from the MIE promoters (3B). Expression from the MIE locus is controlled by the distal promoter (dP), the major immediate early promoter (MIEP), and two intronic MIE promoters (iP1 and iP2). The dP, the major immediate early promoter (MIEP), intronic promoter 1 (iP1), and intronic promoter 2 (iP2) give rise to transcripts encoding full length IE1 and IE2. Transcription start sites for each promoter are depicted with raised arrows (3A). The translation start site (AUG) is marked in exon 2 (3B). Mature mRNAs encoding IE1 and IE2 will also include exons 3 and 4 or 3 and 5, respectively. Primer pairs designed to detect discreet transcripts by RT-qPCR (dP/MIEP=orange, iP1=blue; iP2=teal) are shown. A common reverse primer (black arrow) was used to amplify dP/MIEP- and iP2-derived transcripts. Transcripts from the four promoters differ in their 5' ends. Primer positions used to distinguish transcripts derived from dP or MIEP, iP1, or iP2 are shown.

FIG. 4A is a schematic of luciferase reporter constructs. FIG. 4B is a bar graph showing the activity of each reporter when measured in transfected HeLa cells.

FIGS. 11A and 11B are alignments of HCMV MIE Intron A, strain TB40 (i.e., wildtype) (SEQ ID NO:1) compared to three deletion mutants: ΔiP1 (SEQ ID NO:7), ΔiP2 (SEQ ID NO:8), and ΔiP(1+2) (SEQ ID NO:9). Intron A is the sequence positioned between exon 1 and exon 2 of the classical MIEP-derived transcript described by Stinski and colleagues (Stenberg et. al., *Journal of Virology*, 49: 190-199 (1984)). In strain TB40, Intron A is 827 residues in length and is found between coordinates 206496 and 207322 of the NCBI Genbank file with the accession #EF999921 (note that the intron A sequence is on the complementary or "minus" strand in this Genbank file). In FIG. 11A the highlighted, lowercase sequence corresponds to LoxP sequence introduced during construction of the viruses. FIG. 11B parallels FIG. 11A, but wherein the LoxP sequence is removed.

FIG. 12 an alignment of HCMV MIE "Intron A" from HCMV strain TB40 (SEQ ID NO:15) compared to strains AD169, Merlin (Dolan et al., *J. Gen. Virol* 85, 1301-1312 (2004)), and Towne (Bradley et al., *J. Gen. Virol*, 90, 2375-2380 (2009)), and provides a consensus sequence thereof. "Intron A" is comprised of an 821 base pairs intron DNA sequence located between exons 1 and 2 of the classical MIEP-derived transcript described by Stinski and colleagues (Stenberg et. al., *Journal of Virology*, 49: 190-199 (1984)). In strain Merlin, Accession #NC_006273, which is the NCBI reference sequence for HCMV, Intron A is 821 base pairs in length and is the sequence from positions 174108 to 174928 of the Genbank file. Stretches of non-consensus sequence of more than 10 nucleotides include SEQ ID NOS:16, 17, and 18.

DETAILED DESCRIPTION OF THE INVENTION

I. Definitions

Figure 1A:
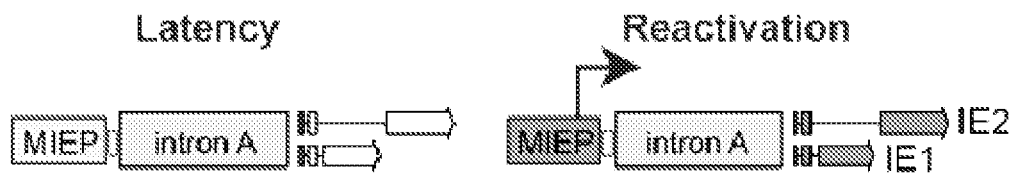
FIG. 1A is an existing model of latency and reactivation that presumes that the MIEP, silenced during latency, is stimulated during reactivation for the re-expression of IE1 and IE2.

As used herein, the term "isolated" describes a compound of interest (e.g., either a polynucleotide or a polypeptide) that is in an environment different from that in which the compound naturally occurs e.g. separated from its natural milieu such as by concentrating a peptide to a concentration at which it is not found in nature. "Isolated" includes compounds that are within samples that are substantially enriched for the compound of interest and/or in which the compound of interest is partially or substantially purified. With respect to nucleic acids, the term "isolated" includes any non-naturally-occurring nucleic acid sequence, since such non-naturally-occurring sequences are not found in nature and do not have immediately contiguous sequences in a naturally-occurring genome.

As used herein, the term "nucleic acid(s)" refers to any nucleic acid containing molecule, including, but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. In accordance with standard nomenclature, nucleic acid sequences are denominated by either a three letter, or single letter code as indicated as follows: adenine (Ade, A), thymine (Thy, T), guanine (Gua, G) cytosine (Cyt, C), uracil (Ura, U).

As used herein, the term "polynucleotide" refers to a chain of nucleotides of any length, regardless of modification (e.g., methylation).

As used herein, the term "gene" refers to a nucleic acid (e.g., DNA or RNA) sequence that including coding sequences necessary for the production of a polypeptide, RNA (e.g., including but not limited to, mRNA, tRNA and rRNA) or precursor. The polypeptide, RNA, or precursor can be encoded by a full length coding sequence or by any portion thereof. The term also encompasses the coding region of a structural gene and the sequences located adjacent to the coding region on both the 5' and 3' ends for a distance of about 1 kb on either end such that the gene corresponds to the length of the full-length mRNA. The term "gene" encompasses both cDNA and genomic forms of a gene, which may be made of DNA, or RNA. A genomic form or clone of a gene may contain the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "nucleic acid molecule encoding," refers to the order or sequence of nucleotides along a strand of nucleotides. The order of these nucleotides determines the order of amino acids along the polypeptide (protein) chain.

As used herein, "heterologous" means derived from a different species.

As used herein, "homologous" means derived from the same species. For example, a homologous trait is any characteristic of organisms that is derived from a common ancestor. Homologous sequences can be orthologous or paralogous. Homologous sequences are orthologous if they were separated by a speciation event: when a species diverges into two separate species, the divergent copies of a single gene in the resulting species are said to be orthologous. Orthologs, or orthologous genes, are genes in different species that are similar to each other because they originated from a common ancestor. Homologous sequences are paralogous if they were separated by a gene duplication event: if a gene in an organism is duplicated to occupy two different positions in the same genome, then the two copies are paralogous.

As used herein, "autologous" means derived from self.

As used herein, "endogenous" means a substance that originates from within an organism, tissue, or cell.

As used herein, "exogenous" means a substances that originates from outside an organism, tissue, or cell.

As used herein a "recombinant protein" is a protein derived from recombinant DNA.

As used herein "recombinant DNA" a refers to DNA molecules that is extracted from different sources and chemically joined together; for example DNA including a gene from one source may be recombined with DNA from another source. Recombinant DNA can be all heterologous DNA or a combination of homologous and heterologous DNA. The recombinant DNA can be integrated into and expressed from a cell's chromosome, or can be expressed for an extra-chromosomal array such as a plasmid.

As used herein, the term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, a "variant," "mutant," or "mutated" polynucleotide or polypeptide contains at least one polynucleotide or polypeptide sequence alteration as compared to the polynucleotide or polypeptide sequence of the corresponding wild-type or parent polynucleotide or polypeptide. Mutations may be natural, deliberate, or accidental. Mutations include substitutions, deletions, and insertions.

As used herein, a "nucleic acid sequence alteration" can be, for example, a substitution, a deletion, or an insertion of one or more nucleotides. An "amino acid sequence alteration" can be, for example, a substitution, a deletion, or an insertion of one or more amino acids.

As used herein, "identity," as known in the art, is a relationship between two or more polynucleotide or polypeptide sequences, as determined by comparing the sequences. In the art, "identity" also means the degree of sequence relatedness between the polynucleotide or polypeptide as determined by the match between strings of such sequences. "Identity" can also mean the degree of sequence relatedness of a polynucleotide or polypeptide compared to the full-length of a reference polynucleotide or polypeptide. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polynucleotides or polypeptides of the present disclosure.

By way of example, a polynucleotide or polypeptide sequence may be identical to the reference sequence, that is be 100% identical, or it may include up to a certain integer number of nucleotides or amino acid alterations as compared to the reference sequence such that the % identity is less than 100%. Such alterations are selected from: at least one deletion, substitution, including conservative and non-conservative substitution, or insertion, and wherein said alterations may occur at the 5' or 3' end of the polynucleotide, or amino- or carboxy-terminal positions of the reference polypeptide sequence or anywhere between those terminal positions, interspersed either individually among the nucleic acids or amino acids in the reference sequence or in one or more contiguous groups within the reference sequence. The number of nucleotide or amino acid alterations for a given % identity is determined by multiplying the total number of nucleic acids or amino acids in the reference polynucleotide or polypeptide by the numerical percent of the respective percent identity (divided by 100) and then subtracting that product from said total number of nucleic acids or amino acids in the reference polynucleotide or polypeptide.

As used herein, "operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will assist the linked protein to be localized at the specific organelle.

As used herein, "tropism" refers to the propensity of a molecule to be attracted to a specific cell, cell type or cell state. In the art, tropism can refer to the way in which different viruses and pathogens have evolved to preferentially target to specific host species, or specific cell types within those species. The propensity for a molecule to be attracted to a specific cell, cell type or cell state can be accomplished by means of a targeting signal.

As used herein, the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease, and the treatment being effected.

As used herein, the terms "neoplastic cells," "neoplasia," "tumor," "tumor cells," "cancer" and "cancer cells," (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign.

As used herein, an "immunogen" or "immunogenic amount" refers to the ability of a substance (antigen) to induce an immune response. An immune response is an alteration in the reactivity of an organism's immune system in response to an antigen, in vertebrates, this may involve antibody production, induction of cell-mediated immunity, complement activation or development of immunological tolerance.

As used herein, an "adjuvant" is a substance that increases the ability of an antigen to stimulate the immune system.

As used herein, "attenuated" refers to refers to procedures that weaken an agent of disease (a pathogen). An attenuated virus is a weakened, less vigorous virus. A vaccine against a viral disease can be made from an attenuated, less virulent strain of the virus, a virus capable of stimulating an immune response and creating immunity but not causing illness or less severe illness. Attenuation can be achieved by chemical treatment of the pathogen, through radiation, or by genetic modification, using methods known to those skilled in the art. Attenuation may result in decreased proliferation, attachment to host cells, or decreased production or strength of toxins.

As used herein, the terms "subject," "individual," and "patient" refer to any individual who is the target of treatment using the disclosed compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

As used herein, "treat" means to prevent, reduce, decrease, or ameliorate one or more symptoms, characteristics or comorbidities of an age-related disease, disorder or condition; to reverse the progression of one or more symptoms, characteristics or comorbidities of an age related disorder; to halt the progression of one or more symptoms, characteristics or comorbidities of an age-related disorder; to prevent the occurrence of one or more symptoms, characteristics or comorbidities of an age-related disorder; to inhibit the rate of development of one or more symptoms, characteristics or comorbidities or combinations thereof.

II. Viral Compositions

It has been discovered that the differentiation of latently infected cells induces the expression and activation of host transcription factors, which bind intronic promoters to induce gene expression and herpesvirus reactivation.

The replicative cycle of HCMV is initiated from the major immediate early (MIE) locus, where the major immediate early promoter (MIEP) drives the expression of a number of proteins required to transactivate the viral genome. Of these, the 1E1-72 kDa (IE1) and the 1E2-86 kDa (IE2) proteins are best characterized. Due to their important role in replication, an understanding of how IE1 and IE2 expression is regulated during lytic infection is well developed. However, there was previously only a limited understanding of the mechanisms controlling IE1 and IE2 expression during reactivation from latency.

The MIEP, and consequently IE1 and IE2 expression, is silenced in hematopoietic cells and during the establishment of latency (Murphy, et al., *Proceedings of the National Academy of Sciences of the United States of America*, 105, 5453-5458 (2008), Saffert, et al., *Journal of Virology*, (2007), Reeves, et al., *Virus research*, 157, 134-143 (2011), Sinclair, et al., *Biochimica et biophysica acta*, 1799, 286-295 (2010), Qin, et al., *Journal of Virology*, 87, 9886-9894 (2013)). Thus, historically it was believed that the MIEP must be de-repressed for HCMV to reactivate. Differentiation of latently infected monocytes or progenitor cells triggers re-expression of the IE1 and IE2 proteins, leading to re-entry into the HCMV replicative cycle (FIG. 1A-1B and FIG. 2) (Soderberg-Naucler, et al., *Cell*, 91, 119-26 (1997), Reeves, et al., *Proceedings of the National Academy of Sciences of the United States of America*, 102, 4140-4145 (2005), Taylor-Wiedeman, et al., *Journal of Virology*, 68, 1597-604 (1994)). The historical model of latency and reactivation presumes that the MIEP, silenced during latency, is stimulated during reactivation for the re-expression of IE1 and IE2 (FIG. 1A).

Figure 1B:
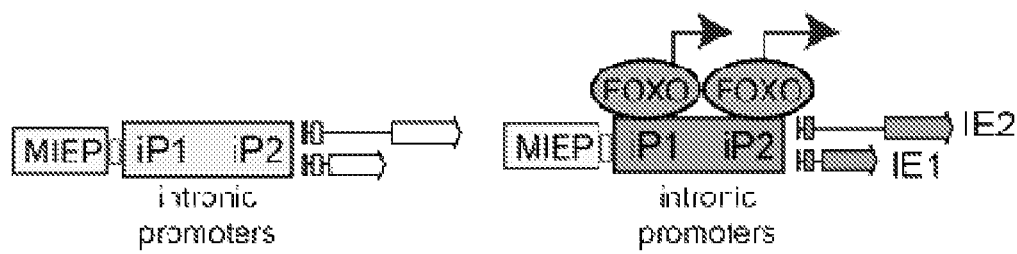
FIG. 1B is a revised model instead features the iP1 and iP2 promoters within the first intron of the MIE locus. The data described herein indicates that intronic promoters (e.g., FIG. 1B), and not the MIEP (e.g., FIG. 1A), account for reactivation from latency, and identify FOXO transcription factors as host factors important for stimulating the activity of the intronic promoters.

However, the examples below identify two promoters within the first intron of the MIE locus, and show that these intronic promoters, and not the MIEP, account for reactivation from latency (FIG. 1B). Further, FOXO transcription factors are identified as host factors important for stimulating the activity of the intronic promoters. Thus, the decision to reactivate is intimately linked to changes in the biology of latently infected cells. The molecular cues that link changes in cell biology and HCMV reactivation were also previously poorly understood. The results indicate that the FOXO family of transcription factors (TFs) are part of this missing link, as they are important mediators of monocyte differentiation, and also regulate the disclosed MIE promoters that are required for HCMV reactivation. Thus, the results presented below establish molecular events driven by changes in cell differentiation that induce the reactivation of latent HCMV genomes.

Thus, a strategy for developing safer viruses is provided. Viruses with reduced, impaired, or unable to reactive from latency, pharmaceutical compositions including the viruses, and method of use thereof are disclosed.

The viruses are particularly useful in vaccine strategies because viral stocks can be easily made and maintained (e.g., without the usual vaccine obstacles to making other attenuated virus such as those with conditionally mutated IE genes) but it cannot reactivate.

A. Structure of the Viruses

Viruses impaired or unable to reactive from latency are provided. Typically, the viral genome of such viruses have one or more mutations in one or more intronic promoters that regulate or drive expression of one or more genes, and the proteins encoded thereby, needed for reactivation. The viruses thus have reduced expression from one or more promoters. The reduced expression can be reduce activation and/or induction of the promoter. The reduced expression can be less frequent activation and/or induction of the promoter, less mRNA transcribed from one or more genes operably linked to the promoter, or a combination thereof.

The mutation(s) can be a substitution, deletion, insertion, or combination thereof, provided that the activity of the one or more targeted promoters is reduced relative to that of a control virus (e.g., a wildtype or other unmutated virus capable of reactivation). In some embodiments the mutation(s) reduce binding of one or more transcription factors, for example, one or more host transcription factors. In particular embodiments the host transcription factor(s) is one or more FOXO transcription factors. The host transcription factor can be one that is expressed during differentiation of the host cell. The host can be a human.

Viral genomes with one or more mutations in one or more intronic promoters that drive expression of one or more proteins needed for reactivation, can include other genomic alterations including, but not limited to, mutations that modulate infection, replication, cellular tropism, immune response in the host, or a combination, and/or insertion of heterologous sequences that can express one or more heterologous proteins (e.g., antigens).

1. Promoter Sequences

Generally, a promoter is a region of DNA that initiates transcription of a particular gene. Promoters are typically located near the transcription start sites of genes, on the same strand and upstream on the DNA (towards the 5' region of the sense strand). Promoters can be about 100-1000 base pairs long.

The experiments presented below illustrate that sequences within the MIE region of HCMV are important for re-expression of IE1 and 1E2 in latently infected cells. Two promoters whose transcriptional start sites (TSS) are nested within Intron A of the major immediate (MIE) locus (intronic promoters) the HCMV genome (also referred to herein as "iP1" and "iP2," respectively) were identified.

An exemplary sequence for HCMV MIE Intron A can be found in GenBank: EF999921.1, VRL 26 Jul. 2016, Human herpesvirus 5 strain TB40/E clone TB40-BAC4, complete sequence, which is specifically incorporated by reference in its entirety.

An exemplary HCMV MIE Intron A sequence is

GTAAGTACCGCCTATAGACTCTATAGGCCCACCCCCTTGGCTTCTTATG

CATGCTATACTGTTTTTGGCTTGGGGTCTATACACCCCCGCTTCCTTAT

GCTATAGGTGATGGTATAGCTTAGCCTATAGGTGTGGGTTATTGACCAT

TATTGACCACTCCCCTATTGGTGACGATACTTTCCATTACTAATCCATA

ACATGGCTCTTTGCCACAACTCTCTTTATTGGCTATATGCCAATACTCT

GTCCTTCAGAGACTGACACGGACTCTGTATTTTTACAGGATGGGGTCCC

ATTTATTATTTACAAATTCACATATACAACAACACCGTCCCCAGTACC

CGCAGTTTTTAT_TAAACATAGCGT_GGGATCTCCACGCGAATCTCGGG

TACGTGTTCCGGACATGGGCTCTTCTCCGGTAGCGGCGGAGCTTCTACAT

CCGAGCCCTGCTCCCATGCCTCCAGCGGCTCATGGTCGCTTGGCAGCTCC

TTGCTCCTAACAGTGGAGGCCAGACTTAGGCACAGCACGATGCCCACCAC

CACCAGTGTGCCGCACAAGGCCGTGGCGGTAGGGTATGTGTCT

_GAAAATGAGCT_CGGGGAGCGGGCTTGCACCGCTGACGCATTTGGAAGA

CTTAAGGCAGCGG_CAGAAGAA_GATGCAGGCAGCTGAGTTGTTGTGTTC

TGATAAGAGTCAGAGGTAACTCCCGTTGCGGTGCTGTTAACGGTGGAGG

GCAGTGTAGTCTGAGCAGTACTCGTTGCTGCCGCGCGCGCCACCAGAC

ATAATAGCTGACAGACTAACAGACTGTTCCTTTCCATGGGTCTTTTCTG

CAG (SEQ ID NO:1,

Intron A (TB40)). The transcriptional start sites (TSS) of iP1 and iP2 are identified with bold and underlining Exemplary FOXO binding sites are identified with dashed underlining and italics.

Another exemplary sequence for HCMV MIE Intron A can be found in GenBank: FJ527563.1, Human herpesvirus 5 strain AD169, complete genome, which is specifically incorporated by reference in its entirety.

Another exemplary HCMV MIE Intron A sequence is

GTAAGTACCGCCTATAGAGTCTATAGGCCCACCCCCTTGGCTTCTTATG

CATGCTATACTGTTTTTGGCTTGGGGTCTATACACCCCCGCTTCCTCAT

GTTATAGGTGATGGTATAGCTTAGCCTATAGGTGTGGGTTATTGACCAT

TATTGACCACTCCCCTATTGGTGACGATACTTTCCATTACTAATCCATA

ACATGGCTCTTTGCCACAACTCTCTTTATTGGCTATATGCCAATACACT

GTCCTTCAGAGACTGACACGGACTCTGTATTTTTACAGGATGGGGTCTC

ATTTATTATTTACAAATTCACATATACAACACCACCGTCCCCAGTGC

CCGCAGTTTTTAT_TAAACATAACGT_GGGATCTCCACGCGAATCTCG

GGTACGTGTTCCGGACATGGGCTCTTCTCCGGTAGCGGCGGAGCTTCTA

CATCCGAGCCCTGCTCCCATGCCTCCAGCGACTCATGGTCGCTCGGCAG

CTCCTTGCTCCTAACAGTGGAGGCCAGACTTAGGCACAGCACGATGCCC

ACCACCACCAGTGTGCCGCACAAGGCCGTGGCGGTAGGGTATGTGTCT

_GAAAATGAGCT_CGGGGAGCGGGCTTGCACCGCTGACGCATTTGGAAGA

CTTAAGGCAGCGG_CAGAAGAA_GATGCAGGCAGCTGAGTTGTTGTGTTC

TGATAAGAGTCAGAGGTAACTCCCGTTGCGGTGCTGTTAACGGTGGAGG

GCAGTGTAGTCTGAGCAGTACTCGTTGCTGCCGCGCGCGCCACCAG

CATAATAGCTGACAGACTAACAGACTGTTCCTTTCCATGGGTCTTTTCT

GCAG (SEQ ID NO:2.

Intron A (AD169)). The transcriptional start sites (TSS) of iP1 and iP2 are identified with bold and underlining Exemplary FOXO binding sites are identified with dashed underlining and italics.

Thus, a region of an HCMV genome that includes promoter elements of the iP1 and/or iP2 promoters can be SEQ ID NO:1 or 2, or a functional fragment thereof, or a sequence with at least 60, 70, 80, 85, 90, 95, 96, 97, 98, or 99% sequence identity to SEQ ID NO:1 or 2, or a reverse complement of any of the foregoing.

An exemplary region of an HCMV genome that includes promoter elements of the iP1 promoter is

```
ATCGCCTGGAGACGCCATCCACGCTGTTTTGACCTCCATAGAAGACACC

GGGACCGATCCAGCCTCCGCGGCCGGGAACGGTGCATTGGAACGCGGAT

TCCCCGTGCCAAGAGTGACGTAAGTACCGCCTATAGACTCTATAGGCCC

ACCCCCTTGGCTTCTTATGCATGCTATACTGTTTTTGGCTTGGGGTCTA

TACACCCCCGCTTCCTCATGCTATAGGTGATGGTATAGCTTAGCCTATA

GGTGTGGGTTATTGACCATTATTGACCACTCCCCTATTGGTGACGATAC

TTTCCATTACTAATCCATAACATGGCTCTTTGCCACAACTCTCTTTATT

GGCTATATGCCAATACTCTGTCCTTCAGAGACTGACACGGACTCTGTAT

TTTTACAGGATGGGGTCCCATTTATTATTTACAAATTCACATATACAAC

AACACCGTCCCCAGTACCCGCAGTTTTTATTAAACATAGCGTGGGA

TCTCCACGCGAAT (SEQ ID NO:3,
```

–450 to +50 relative to the TSS, (TB40)), or a functional fragment thereof, or a sequence with at least 60, 70, 80, 85, 90, 95, 96, 97, 98, or 99% sequence identity to SEQ ID NO:3, or a reverse complement of any of the foregoing. The transcriptional start sites (TSS) of iP1 is identified with bold and underlining. Exemplary FOXO binding sites are identified with dashed underlining and italics.

An exemplary region of an HCMV genome that includes promoter elements of the iP2 promoter is

```
AACACCGTCCCCAGTACCCGCAGTTTTTATTAAACATAGCGTGGGAT

CTCCACGCGAATCTCGGGTACGTGTTCCGGACATGGGCTCTTCTCCGGT

AGCGGCGGAGCTTCTACATCCGAGCCCTGCTCCCATGCCTCCAGCGGCT

CATGGTCGCTTGGCAGCTCCTTGCTCCTAACAGTGGAGGCCAGACTTAG

GCACAGCACGATGCCCACCACCACCAGTGTGCCGCACAAGGCCGTGGCG

GTAGGGTATGTGTCTGAAAATGAGCTCGGGGAGCGGGCTTGCACCGC

TGACGCATTTGGAAGACTTAAGGCAGCGGCAGAAGAAGATGCAGGCA

GCTGAGTTGTTGTGTTCTGATAAGAGTCAGAGGTAACTCCCGTTGCGGT

GCTGTTAACGGTGGAGGGCAGTGTAGTCTGAGCAGTACTCGTTGCTGCC

GCGCGCGCCACCAGACATAATAGCTGACAGACTAACAGACTGTTCCT

TTCCATGGGTCTTTTCTG (SEQ ID NO:5,
```

–450 to +50 relative to the TSS, (TB40)), or a functional fragment thereof, or a sequence with at least 60, 70, 80, 85, 90, 95, 96, 97, 98, or 99% sequence identity to SEQ ID NO:5, or a reverse complement of any of the foregoing. The transcriptional start sites (TSS) of iP2 is identified with bold and underlining. Exemplary FOXO binding sites are identified with dashed underlining and italics.

Another exemplary region of an HCMV genome that includes promoter elements of the iP1 promoter is

```
ATCGCCTGGAGACGCCATCCACGCTGTTTTGACCTCCATAGAAGACACC

GGGACCGATCCAGCCTCCGCGGCCGGGAACGGTGCATTGGAACGCGGAT

TCCCCGTGCCAAGAGTGACGTAAGTACCGCCTATAGAGTCTATAGGCCC

ACCCCCTTGGCTTCTTATGCATGCTATACTGTTTTTGGCTTGGGGTCTA

TACACCCCCGCTTCCTCATGTTATAGGTGATGGTATAGCTTAGCCTATA

GGTGTGGGTTATTGACCATTATTGACCACTCCCCTATTGGTGACGATAC

TTTCCATTACTAATCCATAACATGGCTCTTTGCCACAACTCTCTTTATT

GGCTATATGCCAATACACTGTCCTTCAGAGACTGACACGGACTCTGTAT

TTTTACAGGATGGGGTCTCATTTATTATTTACAAATTCACATATACAAC

ACCACCGTCCCCAGTGCCCGCAGTTTTTATTAAACATAACGTGGG

ATCTCCACGCGAAT (SEQ ID NO:4,
```

–450 to +50 relative to the TSS, (AD169)), or a functional fragment thereof, or a sequence with at least 60, 70, 80, 85, 90, 95, 96, 97, 98, or 99% sequence identity to SEQ ID NO:4, or a reverse complement of any of the foregoing. The transcriptional start sites (TSS) of iP1 is identified with bold and underlining. Exemplary FOXO binding sites are identified with dashed underlining and italics.

Another exemplary region of an HCMV genome that includes promoter elements of the iP2 promoter is

```
ACCACCGTCCCCAGTGCCCGCAGTTTTTAT TAAACATAACGTGGG

ATCTCCACGCGAATCTCGGGTACGTGTTCCGGACATGGGCTCTTCTAG

CGGCGGAGCTTCTACATCCGAGCCCTGCTCCCATGCCTCCAGCGACTC

CGGTCATGGTCGCTCGGCAGCTCCTTGCTCCTAACAGTGGAGGCCAGA

CTTAGGCACAGCACGATGCCCACCACCACCAGTGTGCCGCACAAGGCC

GTGGCGGTAGGGTATGTGTCTGAAAATGAGCTCGGGGAGCGGGCTTG

CACCGCTGACGCATTTGGAAGACTTAAGGCAGCGGCAGAAGAAGAT

GCAGGCAGCTGAGTTGTTGTGTTCTGATAAGAGTCAGAGGTAACTCCC

GTTGCGGTGCTGTTAACGGTGGAGGGCAGTGTAGTCTGAGCAGTACTC

GTTGCTGCCGCGCGCGCCACCAGACATAATAGCTGACAGACTAACA

GACTGTTCCTTTCCATGGGTCTTTTCTG (SEQ ID NO:6,
```

–450 to +50 relative to the TSS, AD169)), or a functional fragment thereof, or a sequence with at least 60, 70, 80, 85, 90, 95, 96, 97, 98, or 99% sequence identity to SEQ ID NO:6, or a reverse complement of any of the foregoing. The transcriptional start sites (TSS) of iP2 is identified with bold and underlining. Exemplary FOXO binding sites are identified with dashed underlining and italics.

In some embodiments, the mutation or mutations include or consist of one or more substitutions, insertion, or deletions that reduce or prevent binding of a transcription factor to one or more of the promoters. An exemplary transcription factor is a FOXO transcription factor such as FOXO3a. An exemplary FOXO binding motif is (RAAATAA). Exemplary putative FOXO binding motifs are also identified above in SEQ ID NOS:1-6. An exemplary mutation(s) that reduces FOXO binding to a promoter is changing two adenines in one or more FOXO-binding motifs to cytosines (RACCTAA). Mutant viruses wherein one or more of the FOXO binding motifs are substituted with RACCTAA, or another function-reducing mutation are expressly disclosed. Thus, in specific examples, one or more transcription factor binding sites identified the sequences provided herein, or the homologous sequence thereto in another virus, are mutated to reduce function, by for example, substituting the sequence RACCTAA or analogous mutation.

Herpesviruses including HCMV are double stranded DNA (dsDNA) viruses. The promoters disclosed herein can be identified by reference or recitation of either of the two strands of DNA. Thus, in addition to the sequences provided herein, in each case, the reverse complement for each sequence, including putative FOXO binding sites, TSS, etc., is also expressly disclosed.

2. Exemplary Viral Backbones

The disclosed viruses can be naturally occurring or recombinant viruses. The disclosed viruses are typically those that include an iP1 promoter and/or an iP2 promoter, or a homologous sequence thereto. The homolog can be a paralogue or an orthologue. Typically, the virus includes one or more mutations in the iP1 promoter and/or an iP2 promoter, or the homologous sequence thereto that reduces activity of one or more of the promoters, reduces reactivation of the virus from latency, or preferably a combination thereof. Thus, a naturally occurring virus can be one that already has one or more mutations in the iP1 promoter and/or an iP2 promoter, or the homologous sequence thereto relative to a wildtype virus with a fully functional iP1 promoter and/or an iP2 promoter.

More typically, the virus is a recombinant virus, wherein one or more mutations has been introduced into the iP1 promoter and/or an iP2 promoter, or the homologous sequence thereto that reduces, impairs, or completely abolishes it's activity.

In some embodiments, the mutation(s) reduces expression of one of more transcripts that are induced or increased by one or more promoters in genomic region of the virus corresponding with any one of SEQ ID NOS:1-6, or a combination thereof. The mutation or mutations can be a substitution, insertion, deletion, or combination thereof.

The virus into which the one or more mutations into the iP1 promoter and/or an iP2 promoter, or the homologous sequence thereto is introduced can be referred to as a parent or parental virus, or virus or viral backbone.

One of skill in the art can identify the region corresponding to the region in which the iP1 and/or an iP2 promoters reside, and the subsequences thereof that define the promoters in viruses, using, for example, any one of SEQ ID NOS:1-6 as BLASTN queries and/or sequence alignment techniques for global comparison to another virus's genomic sequences. Non-limiting examples of such techniques are discussed in the examples below. Results from an exemplary BLASTN search provided. The top 100 hits having at least 99% sequence identity corresponding to at least 498 bases of a query of 500 bases of the TB40-450 to +50 region relative to the iP1 and iP2 transcription start sites are provided below in Tables 1 and 2, respectively. An exemplary sequence alignment of TB40 with the corresponding sequences in several other exemplary strains of HCMV including AD169 Bradley, Merlin, and Towne, and a consensus sequence derived therefrom is illustrated in FIG. 12.

The viruses exemplified in the experiments below are cytomegaloviruses. Thus, in some embodiments, the virus is a cytomegalovirus (CMV). CMVs are members of the beta subclass of the family of herpesviruses. CMVs are double-stranded DNA viruses with a large (~230 kB) genome. There are a range of host-range specific variants such as MCMV (murine CMV), RhCMV 45 (rhesus CMV) and HCMV (human CMV). The disclosed viruses can be, for example, any strain, isolate or variant of a rhesus CMV, mouse CMV, or human CMV. Thus, genomic sequences of a rhesus CMV, mouse CMV, and human CMV can serves as a viral backbone for further engineering to include one or more mutations in the iP1 promoter, iP2 promoter, or a combination thereof, alone or combination with one or more additional modifications such as those discussed in more detail below.

In some embodiments, the background virus is TB40 or another known HCMV, for example, one of the HCMVs listed by Genbank accession number in Table 1 or Table 2, each of which is incorporated by reference herein in its entirety.

Additionally, exemplary viruses that can serve as a viral backbone are discussed in, for example, U.S. Pat. Nos. 9,546,355 and 9,249,427, Wang et al., *Sci. Transl. Med.*, 8, 362ra145 (2016), and Hansen, et al., *Nature Medicine*, 15(3):293-299 (2011) (and supplemental information, addendum and correction associated therewith), each of which is specifically incorporated by reference herein in its entirety. For example, U.S. Pat. No. 9,249,427 provides the full nucleotide sequences of RhCMV (Cercopithecine herpesvirus 8), HCMV (AD169 lab strain), HCMV (wild type strain Merlin), Towne BAC HCMV isolate, PH-BAC HCMV isolate, Toledo-BAC HCMV isolate, TR-BAC HCMV isolate, FIX-BAC HCMV isolate, and AD 169-BAC HCMV isolate, any of which can serve as a parent virus to the iP1 and/or iP2 mutant viruses disclosed herein.

Although most typically discussed herein with respect to CMVs such as HCMV, the virus can also be another herpesvirus. There are more than 130 herpesviruses, some of them from mammals, birds, fish, reptiles, amphibians, and mollusks. There are 9 herpesvirus types known to infect humans: herpes simplex viruses 1 and 2, HSV-1 and HSV-2, (also known as HHV1 and HHV2), varicella-zoster virus (VZV, which may also be called by its ICTV name, HHV-3), Epstein-Barr virus (EBV or HHV-4), human cytomegalovirus (HCMV or HHV-5), human herpesvirus 6A and 6B (HHV-6A and HHV-6B), human herpesvirus 7 (HHV-7), and Kaposi's sarcoma-associated herpesvirus (KSHV, also known as HHV-8). Like HCMV, disrupting PI3K/Akt signaling reactivates latent HSV-1 in neuronal cultures (Camarena, et al., *Cell host & microbe*, 8, 320-330 (2010)). Similarly, the gammaherpesviruses KSHV and EBV activate PI3K/Akt signaling to maintain latency, and suppress FOXO transcription factors in latently infected cells (Bhatt, et al., *Front Immunol*, 3, 401 (2012)). Like IE1 and IE2, the KSHV Rta gene, a functional homolog of HCMV IE2, is regulated by multiple promoters that are differentially active in different cell types (Wakeman, et al., *Journal of Virology*, (2014). doi:10.1128/JVI.03110-13, Wakeman, et al., *Journal of Virology*, 91, e01434-16 (2017)). The techniques described herein and otherwise known in the (e.g., sequence searching and alignment), and be used to identify and mutate the sequence in other herpesviruses corresponding to iP1 and iP2 of HCMV.

Exemplary viruses were also made and tested in the working examples below. Thus, in some embodiments, the viruses have the following sequences relative to SEQ ID NO:1 (see also FIG. 11A).

ΔiP1

(SEQ ID NO: 7)
GTAAGTACCGCCTATAGACTCTATAGGCCCAtaacttcgtatagcatac attataCGaAGTTaTTTAAACATAGCGTGGGATCTCCACGCGAATCTCG

GGTACGTGTTCCGGACATGGGCTCTTCTCCGGTAGCGGCGGAGCTTCTA

CATCCGAGCCCTGCTCCCATGCCTCCAGCGGCTCATGGTCGCTTGGCAG

CTCCTTGCTCCTAACAGTGGAGGCCAGACTTAGGCACAGCACGATGCCC

ACCACCACCAGTGTGCCGCACAAGGCCGTGGCGGTAGGGTATGTGTCTG

AAAATGAGCTCGGGGAGCGGGCTTGCACCGCTGACGCATTTGGAAGACT

TAAGGCAGCGGCAGAAGAAGATGCAGGCAGCTGAGTTGTTGTGTTCTGA

TAAGAGTCAGAGGTAACTCCCGTTGCGGTGCTGTTAACGGTGGAGGGCA

GTGTAGTCTGAGCAGTACTCGTTGCTGCCGCGCGCGCCACCAGACATAA

TAGCTGACAGACTAACAGACTGTTCCTTTCCATGGGTCTTTTCTGCAG

ΔiP2

(SEQ ID NO: 8)
GTAAGTACCGCCTATAGACTCTATAGGCCCACCCCCTTGGCTTCTTATG

CATGCTATACTGTTTTTGGCTTGGGGTCTATACACCCCCGCTTCCTTAT

GCTATAGGTGATGGTATAGCTTAGCCTATAGGTGTGGGTTATTGACCAT

TATTGACCACTCCCCTATTGGTGACGATACTTTCCATTACTAATCCATA

ACATGGCTCTTTGCCACAACTCTCTTTATTGGCTATATGCCAATACTCT

GTCCTTCAGAGACTGACACGGACTCTGTATTTTTACAGGATGGGGTCCC

ATTTATTATTTACAAATTCACATATACAACAACACCGTCCCCAGTACCC

GataacttcgtatagcatacattatacgaagttatCTGCCGCGCGCGCC

ACCAGACATAATAGCTGACAGACTAACAGACTGTTCCTTTCCATGGGTC

TTTTCTGCAG

ΔiP(1 + 2)

(SEQ ID NO: 9)
GTAAGTACCGCCTATAGACTCTATAGGCCCAtaacttcgtatagcatac attatacgaagttatCTGCCGCGCGCGCCACCAGACATAATAGCTGACA

GACTAACAGACTGTTCCTTTCCATGGGTCTTTTCTGCAG

The lower case bases in SEQ ID NOS:7, 8, and 9 (and the highlighted sequences in FIG. 11A) correspond with residual LoxP from the recombination strategy.

The corresponding regions with the LoxP sequences are also provided:

ΔiP1 (without LoxP sequence)

(SEQ ID NO: 10)
GTAAGTACCGCCTATAGACTCTATAGGCCCATTAAACATAGCGTGGGATC

TCCACGCGAATCTCGGGTACGTGTTCCGGACATGGGCTCTTCTCCGGTAG

CGGCGGAGCTTCTACATCCGAGCCCTGCTCCCATGCCTCCAGCGGCTCAT

GGTCGCTTGGCAGCTCCTTGCTCCTAACAGTGGAGGCCAGACTTAGGCAC

AGCACGATGCCCACCACCACCAGTGTGCCGCACAAGGCCGTGGCGGTAGG

GTATGTGTCTGAAAATGAGCTCGGGGAGCGGGCTTGCACCGCTGACGCAT

TTGGAAGACTTAAGGCAGCGGCAGAAGAAGATGCAGGCAGCTGAGTTGTT

GTGTTCTGATAAGAGTCAGAGGTAACTCCCGTTGCGGTGCTGTTAACGGT

GGAGGGCAGTGTAGTCTGAGCAGTACTCGTTGCTGCCGCGCGCGCCACCA

GACATAATAGCTGACAGACTAACAGACTGTTCCTTTCCATGGGTCTTTTC

TGCAG

ΔiP2 (without LoxP sequence)

(SEQ ID NO: 11)
GTAAGTACCGCCTATAGACTCTATAGGCCCACCCCCTTGGCTTCTTATGC

ATGCTATACTGTTTTTGGCTTGGGGTCTATACACCCCCGCTTCCTTATGC

TATAGGTGATGGTATAGCTTAGCCTATAGGTGTGGGTTATTGACCATTAT

TGACCACTCCCCTATTGGTGACGATACTTTCCATTACTAATCCATAACAT

GGCTCTTTGCCACAACTCTCTTTATTGGCTATATGCCAATACTCTGTCCT

TCAGAGACTGACACGGACTCTGTATTTTTACAGGATGGGGTCCCATTTAT

TATTTACAAATTCACATATACAACAACACCGTCCCCAGTACCCGCTGCCG

CGCGCGCCACCAGACATAATAGCTGACAGACTAACAGACTGTTCCTTTCC

ATGGGTCTTTTCTGCAG

ΔiP(1 + 2) (without LoxP sequence)

(SEQ ID NO: 12)
GTAAGTACCGCCTATAGACTCTATAGGCCCACTGCCGCGCGCGCCACCAG

ACATAATAGCTGACAGACTAACAGACTGTTCCTTTCCATGGGTCTTTTCT

GCAG

See also FIG. 11B.

3. Additional Modifications of the Viral Backbone

In some embodiments, the background virus is a recombinant or otherwise engineered virus such as an attenuated virus that has one or more mutations that alter some aspect of the virus relative to a corresponding naturally occurring or wildtype virus.

For example, in some embodiments, the virus includes a mutation in one or more genes important for viral tropism, one or more genes important for infection, one or more genes important for replication, one or more additional genes important for reactivation, one or more genes important for encoding an immunomodulatory protein, or a combination thereof. In some embodiments, the virus is a CMV, and the gene or genes important for replication is selected from UL82, UL94, UL32, UL99, UL115, UL44, or a homolog thereof alone or in any combination.

In some embodiments, the viruses include one or more additional modifications that improve their safety profile. For example, in some embodiments the vectors are either completely or conditionally spread defective or severely restricted in their replication, or a combination thereof. Preferably, these viruses nonetheless remain capable of inducing a protective immune response against one or more autologous, homologous, and/or heterologous antigens.

In some embodiments, the virus is unable to replicate in cells and tissues associated with viral transmission and/or disease. For example, in some embodiments the virus includes an alteration of the cell-tropism of the virus so as to reduce or prevent infection of specific cell types involved in potential tissue damage and/or shedding into urine or secretions. CMV is capable of infecting a wide variety of cells in the host, including: epithelial cells in gut, kidney, lung and retina, neuronal cells in the CNS, hepatocytes, as well as endothelial cells and myeloid lineage cells that are considered persistent sites of the virus. Reducing infection of one or more of these cell types can enhance the safety profile of the virus. Thus, in some embodiments, the virus is a replication competent virus that is unable to infect epithelial cells—a cell type that can be important for virus shedding, particularly for CMVs, as well as a major cell type in the lung associated with CMV pneumonia. Additional or alternative embodiments provide additional safety features into these viruses, including a block in replication in neural and myeloid cells. Preferred viruses will be unable to shed from vaccinated individuals, cause disease in fetuses or immunocompromised adult, or a combination thereof while still able to induce a protective immune response against infectious diseases or tumors.

HCMV encodes >200 genes and several of the genes that are dispensable for basic virus replication have been identified as tropism determinants that enable the virus to enter and replicate in macrophages, endothelial cells, and epithelial cells. One locus of HCMV genes, UL128-131A, has been shown to be important for entry into endothelial and epithelial cells. The UL133/8 locus of HCMV is also important for replication in endothelial cells (ECs). The UL133/8 locus harbors four genes: UL133, UL135, UL136, and UL138. While UL133 and UL138 are dispensable for replication in ECs, both UL135 and UL136 are important (Bughio, et al., *Journal of Virology,* 89(13):6536-50 (2015) doi: 10.1128/JVI.00284-15).

The RhCMV homologs for HCMV UL128 and 130 are inactivated in the RhCMV strain 68-1 used as the backbone vector for the RhCMV/SIV studies. Interestingly, RhCMV 68-1 still grows in epithelial and endothelial cells, but does show reduced shedding compared to low passage RhCMV indicating that reducing epithelial/endothelial cell tropism may attenuate the virus. Mutational analysis of RhCMV 68-1 has identified 4 other RhCMV genes [Rh01 (HCMV TLR1), Rh159 (HCMV UL148), Rh160 (UL132) and Rh203 (HCMVUS22)] that are also required for epithelial cell tropism. In some embodiments, the disclosed viruses have one or more mutations in these or other epithelial cell tropism genes to reduce the ability of CMV to infect epithelial cells, thereby preventing its ability to be shed into urine or glandular secretions (i.e., saliva and breast milk), yet likely not compromise the ability of virus to induce a protective immune response.

Moreover, since CMV infection of epithelial cells in the lung and retina results in pneumonia and retinitis, respectively, elimination of all the CMV epithelial cell tropism genes may reduce the resultant virus's pathogenic potential. Such alterations can prevent shedding and the potential spread of the virus into the unvaccinated population.

In some embodiments, the background virus is a conditional replication defective CMV (rdCMV). The rdCMV can have a nucleic acid sequence encoding one or more fusion proteins that includes an essential viral protein fused to a destabilizing protein. In the absence of a stabilizing agent, the fusion protein is degraded. Thus, the rdCMV can be grown in tissue culture under conditions that allow for replication (i.e., in the presence of the stabilizing agent) but replication is reduced, and preferably prevented, when administered to a patient (in the absence of the stabilizing agent). In some embodiments, the nucleic acid encoding the wild type essential protein are no longer present in the rdCMV and thus the fusion protein is required for viral replication. In preferred embodiments, the essential proteins are selected from the group consisting of IE1/2, UL51, UL52, UL79 and UL84 and the destabilizing protein is FKBP or a derivative thereof. In some embodiments, the stabilizing agent is SHIELD-1. Exemplary replication defective CMV described in U.S. Pat. No. 9,546,355 and Wang et al., *Sci. Transl. Med.,* 8, 362ra145 (2016).

Further embodiments relate to exploiting the tissue-specific expression of cellular microRNAs (miRNAs) to attenuate the virus in tissues associated with disease in adult and congenital infection. miRNAs are small noncoding 21-22 bp RNAs that are highly conserved and expressed in all animal cells from *Drosophila* to humans. miRNAs are an ancient system for posttranscriptional regulation that are involved in a wide range of biological processes and regulate gene expression by binding target sequences in the 3' UTR of mRNAs causing either inhibition of translation of destabilization of the mRNA. These RNA species are also encoded in DNA viruses such as CMV.

A superinfection is a second infection superimposed on an earlier one, especially by a different agent of exogenous or endogenous origin. CMV superinfection or reinfection can occur, for example, in a CMV-seropositive host who receives cells and/or an organ from a seropositive donor, with reactivation of latent virus present in the allograft or reinfection by a new strain of CMV. Although uncontrolled superinfection can be problematic, this characteristic of some viruses including CMV make it desirable as an antigen vector, because the same viral backbone can be used repeatedly to induce immune responses against different antigens. Thus, in some embodiments, the virus maintains the ability to reinfect a subject previously infected with a CMV.

Viruses designed to maintain differentiated effector memory T cell (TEM cell) responses at viral entry sites can also improve vaccine efficacy by impairing viral replication at its earliest stage. See, e.g., U.S. Pat. No. 9,546,355 and Hansen, et al., *Nature Medicine,* 15(3):293-299 (2011) (and supplemental information, addendum and correction associated therewith). For example, in some embodiments, the parent virus is a recombinant virus having a nucleic acid sequence encoding a CMV backbone having a deletion in a gene, such as UL82, that eliminates expression of a functional protein, such as pp71 protein; is deficient in host to host spreading; infects a HCMV seropositive host upon administration of the virus; induces and maintains a long-term effector memory T cell response to the at least one autologous, homologous, or heterologous antigen in said seropositive host; or a combination thereof.

Mammalian miRNAs can either be expressed ubiquitously in all tissues of the host, expressed only during certain times during embryogenesis in which these miRNA species play a major role in developmental processes, or can be expressed only in a tissue-specific manner (such as miR-142-3p in myeloid lineage cells, miR-124 in CNS tissue, and miR-122 in liver). Tissue specific expression of miRNAs can be exploited to generate an attenuated virus. For example, polio vaccine is attenuated through the introduction of multiple miRNA target sequences of miR-124 that is specifically expressed in the CNS into the 3'UTR of the poliovirus genome. Addition of the miR-124 target sequences to the poliovirus genome was observed to significantly attenuate virus infection in mice. Similarly, multiple target sequences of miR-93 that is ubiquitously expressed in all mammalian but not avian tissues were added to the nucleoprotein gene of influenza resulting in a species-restricted influenza mutant that was able to grow in chicken eggs but not in mice.

In some embodiments, the background virus includes a similar strategy to modulate an activity of the virus. Unlike the small RNA viruses, CMVs encode over 200 genes of which approximately 50% are important and necessary for replication or encode structural proteins of the virus. One of these MCMV genes is the immediate early (IE) 3 gene (the mouse correlate of 1E2 in HCMV or RhCMV) that encodes a transcriptional regulatory protein necessary for subsequent activation of early and late genes in the virus. Deletion of this gene completely blocks viral replication in cells and mouse tissues. Thus, introduction of target sequences of tissue-specific miRNAs into the 3'UTR of this gene would attenuate viral replication in these cells.

A further embodiment relates to target sequences of miR-142-3p being expressed only in myeloid lineage cells. Myeloid lineage cells have been shown to represent a reservoir of latent virus, and are thought to harbor and disseminate virus throughout the host. Further studies with MCMV indicate that cross-priming is the primary mechanism by which CMV-encoded proteins prime the immune response, and replication in myeloid dendritic cells may have a surprisingly minimal impact on CMV immunogenicity.

4. Heterologous Antigens

The viral genomes can be engineered to incorporated one or more nucleic acid sequences encoding one or more non-native immunogenic antigens. The sequence encoding the heterologous antigen is typically operably linked to an expression control sequence such that the antigen is expressed by the virus or a host cell infected by the virus.

Exemplary, non-limiting examples of expression control sequences include, but are not limited to the SV40 promoter, and the eF-1a promoter.

One or more genes native to the virus may be truncated or deleted to create additional space for the sequence encoding the immunogenic antigen(s). When expressed by the virus administered to a patient in need thereof, the immunogenic antigen produces prophylactic or therapeutic immunity against a diseases or disorder Immunogenic antigens can be expressed as a fusion protein with other polypeptides including, but limited to, native viral polypeptides, or as a non-fusion protein.

By way of non-limiting examples, the antigen can be protein or polypeptide derived from a virus, bacterium, parasite, plant, protozoan, fungus, tissue or transformed cell such as a cancer or leukemic cell. Antigens may be expressed as single antigens or may be provided in combination.

a. Viral Antigens

A viral antigen can be derived from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

b. Bacterial Antigens

Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus* influenza type B (HIB), *Hyphomicrobium, Legionella, Leptspirosis, Listeria*, Meningococcus A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio*, and *Yersinia.* c. Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

d. Cancer Antigens

In some embodiments, the antigen is a cancer antigen. Antigens expressed by the tumor may be specific to the tumor, or may be expressed at a higher level on the tumor cells as compared to non-tumor cells. Antigenic markers such as serologically defined markers known as tumor associated antigens, which are either uniquely expressed by cancer cells or are present at markedly higher levels (e.g., elevated in a statistically significant manner) in subjects having a malignant condition relative to appropriate controls, are known.

Tumor-associated antigens may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melanoma associated antigens, etc.) (see, e.g., U.S. Pat. No. 6,699,475; Jager, et al.,

*Int. J. Cancer,* 106:817-20 (2003); Kennedy, et al., *Int. Rev. Immunol.,* 22:141-72 (2003); Scanlan, et al. *Cancer Immun.,* 4:1 (2004)).

Genes that encode cellular tumor associated antigens include cellular oncogenes and proto-oncogenes that are aberrantly expressed. In general, cellular oncogenes encode products that are directly relevant to the transformation of the cell, so these antigens are particularly preferred targets for oncotherapy and immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.,* 309:883 (1983); Lloyd, et al., *Int. J. Canc.,* 71:842 (1997). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.,* 36:755 (1997); Sarandakou, et al., *Eur. J. Gynaecol. Oncol.,* 19:73 (1998); Meier, et al., *Anticancer Res.,* 17(4B):2945 (1997); Kudoh, et al., *Gynecol. Obstet. Invest.,* 47:52 (1999)). Elevated serum CA125 may also accompany neuroblastoma (e.g., Hirokawa, et al., *Surg. Today,* 28:349 (1998), while elevated CEA and SCC, among others, may accompany colorectal cancer (Gebauer, et al., *Anticancer Res.,* 17(4B):2939 (1997)).

The tumor associated antigen mesothelin, defined by reactivity with monoclonal antibody K-1, is present on a majority of squamous cell carcinomas including epithelial ovarian, cervical, and esophageal tumors, and on mesotheliomas (Chang, et al., *Cancer Res.,* 52:181 (1992); Chang, et al., *Int. J. Cancer,* 50:373 (1992); Chang, et al., *Int. J. Cancer,* 51:548 (1992); Chang, et al., *Proc. Natl. Acad. Sci. USA,* 93:136 (1996); Chowdhury, et al., *Proc. Natl. Acad. Sci. USA,* 95:669 (1998)). Using MAb K-1, mesothelin is detectable only as a cell-associated tumor marker and has not been found in soluble form in serum from ovarian cancer patients, or in medium conditioned by OVCAR-3 cells (Chang, et al., *Int. J. Cancer,* 50:373 (1992)). Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies (see WO 00/50900).

A tumor antigen may include a cell surface molecule. Tumor antigens of known structure and having a known or described function, include the following cell surface receptors: HER1 (GenBank Accession NO: U48722), HER2 (Yoshino, et al., *J. Immunol.,* 152:2393 (1994); Disis, et al., *Canc. Res.,* 54:16 (1994); GenBank Acc. Nos. X03363 and M17730), HER3 (GenBank Acc. Nos. U29339 and M34309), HER4 (Plowman, et al., *Nature,* 366:473 (1993); GenBank Acc. Nos. L07868 and T64105), epidermal growth factor receptor (EGFR) (GenBank Acc. Nos. U48722, and KO3193), vascular endothelial cell growth factor (GenBank Acc. No. M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043, European Patent No. GB 2241703), insulin-like growth factor-II (GenBank Acc. Nos. X03562, X00910, M17863 and M17862), transferrin receptor (Trowbridge and Omary, *Proc. Nat. Acad. USA,* 78:3039 (1981); GenBank Acc. Nos. X01060 and M11507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., *Proc. Nat. Acad. Sci. USA,* 86:7159 (1989); GenBank Acc. Nos. M65132 and M64928) NY-ESO-1 (GenBank Acc. Nos. AJ003149 and U87459), NA 17-A (PCT Publication NO: WO 96/40039), Melan-A/MART-1 (Kawakami, et al., *Proc. Nat. Acad. Sci. USA,* 91:3515 (1994); GenBank Acc. Nos. U06654 and U06452), tyrosinase (Topalian, et al., *Proc. Nat. Acad. Sci. USA,* 91:9461 (1994); GenBank Acc. NO: M26729; Weber, et al., *J. Clin. Invest,* 102:1258 (1998)), Gp-100 (Kawakami, et al., *Proc. Nat. Acad. Sci. USA,* 91:3515 (1994); GenBank Acc. NO: 573003, Adema, et al., *J. Biol. Chem.,* 269:20126 (1994)), MAGE (van den Bruggen, et al., *Science,* 254:1643 (1991)); GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. NO: U19180; U.S. Pat. Nos. 5,683,886 and 5,571,711), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA, Gold and Freedman, *J. Exp. Med.,* 121:439 (1985); GenBank Acc. Nos. M59710, M59255 and M29540), and PyLT (GenBank Acc. Nos. J02289 and J02038); p97 (melanotransferrin) (Brown, et al., *J. Immunol.,* 127:539-46 (1981); Rose, et al., *Proc. Natl. Acad. Sci. USA,* 83:1261-61 (1986)).

Additional tumor associated antigens include prostate surface antigen (PSA) (U.S. Pat. Nos. 6,677,157; 6,673, 545); β-human chorionic gonadotropin β-HCG) (McManus, et al., *Cancer Res.,* 36:3476-81 (1976); Yoshimura, et al., *Cancer,* 73:2745-52 (1994); Yamaguchi, et al., *Br. J. Cancer,* 60:382-84 (1989): Alfthan, et al., *Cancer Res.,* 52:4628-33 (1992)); glycosyltransferase β-1,4-N-acetylgalactosaminyl-transferases (GalNAc) (Hoon, et al., *Int. J. Cancer,* 43:857-62 (1989); Ando, et al., *Int. J. Cancer,* 40:12-17 (1987); Tsuchida, et al., *J. Natl. Cancer,* 78:45-54 (1987); Tsuchida, et al., *J. Natl. Cancer,* 78:55-60 (1987)); NUC18 (Lehmann, et al., *Proc. Natl. Acad. Sci. USA,* 86:9891-95 (1989); Lehmann, et al., *Cancer Res.,* 47:841-45 (1987)); melanoma antigen gp75 (Vijayasardahi, et al., *J. Exp. Med.*, 171:1375-80 (1990); GenBank Accession NO: X51455); human cytokeratin 8; high molecular weight melanoma antigen (Natali, et al., *Cancer*, 59:55-63 (1987); keratin 19 (Datta, et al., *J. Clin. Oncol.*, 12:475-82 (1994)).

Tumor antigens of interest include antigens regarded in the art as "cancer/testis" (CT) antigens that are immunogenic in subjects having a malignant condition (Scanlan, et al., *Cancer Immun.*, 4:1 (2004)). CT antigens include at least 19 different families of antigens that contain one or more members and that are capable of inducing an immune response, including, but not limited to, MAGEA (CT1); BAGE (CT2); MAGEB (CT3); GAGE (CT4); SSX (CT5); NY-ESO-1 (CT6); MAGEC (CT7); SYCP1 (CT8); SPANXB1 (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens, including a tumor-associated or tumor-specific antigen, include, but are not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomerase, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art.

e. Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.e. grasses of the genera *Lolium, Phleum, Poa, Cynodon, Dactylis, Holcus, Phalaris, Secale*, and *Sorghum*, the orders of Asterales and Urticales including i.a. herbs of the genera *Ambrosia, Artemisia*, and *Parietaria*. Other allergen antigens that may be used include allergens from house dust mites of the genus *Dermatophagoides* and Euroglyphus, storage mite e.g *Lepidoglyphys, Glycyphagus* and *Tyropha-gus*, those from cockroaches, midges and fleas e.g. *Blatella, Periplaneta, Chironomus* and *Ctenocepphalides*, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

B. Methods of Making Viruses

Method of engineering recombinant virus, and mutagenic screens for spontaneous mutations (e.g., by serial passaging or directed evolution) are well known in the art, and can be used to engineer the viruses disclosed herein. For example, many of the references cited herein provided methods for preparing recombinant viruses. In some embodiments, the virus is engineered using a BAC cloning technique. See, e.g., Paredes and Yu, et al., *Current Protocols in Microbiology* 14E.4.1-14E.4.33, February 2012 (DOI: 10.1002/9780471729259.mc14e04s24), which is specifically incorporated by reference in its entirety, and which describes artificial chromosome (BAC) cloning and genetic manipulation of HCMV. The BAC system takes advantage of the single-copy F plasmid of *E. coli* that can stably carry large pieces of foreign DNA. Briefly, a recombinant HCMV carrying a modified F plasmid is first generated in eukaryotic cells. Recombinant viral genomes are then isolated and recovered in *E. coli* as BAC clones. BAC-captured viral genomes can be manipulated using prokaryotic genetics, and recombinant virus can be reconstituted from BAC transfection in eukaryotic cells. This reverse genetic approach provides a reliable and efficient method to introduce genetic alterations into the viral genome in *E. coli* and subsequently analyze their effects on virus biology in eukaryotic cells.

In some embodiments, transgenes such as those encoding heterologous antigens are engineered between US34 and TRS1, for example, as described in Umashankar, et al. *PLoS Pathog* 7(12): e1002444 (2011). Recombinant viruses can be screened by BAC digestion, PCR, and sequencing, and virus stocks were propagated, stored and titered as described in Umashankar, supra, and Petrucelli, *Journal of Virology*, 83: 5615-5629 (2009).

III. Immunogenic Compositions and Methods of Use Thereof

Paradoxically, high levels of CMV-specific immunity are unable to either eradicate the virus from the healthy infected individual, or confer protection of the CMV sero-positive individual against re-infection. This ability of CMV to escape eradication by the immune system, and to re-infect the sero-positive host has long been believed to be linked to the multiple viral immunomodulators encoded by the virus (for review, see (Mocarski, E. S., Jr. 2002. *Trends Microbiol* 10:332-9)).

Since CMVs can establish a life-long infection of the host, the window for realization of any pathogenic potential of a CMV-based vaccine extends from the time of vaccination for the life of the individual. During this window (potentially >80 years) it is expected that some vaccines will encounter periods of immune-suppression, whether this be as a consequence of iatrogenic immune conditioning prior to transplantation, or as a consequence of disease, as with HIV infection or cancer. HCMV is also frequently shed into saliva, urine and breast milk from healthy HCMV-infected individuals for periods of time that range from months to years. This potential of vaccine spread from vaccinated to non-vaccinated individuals is a characteristic of live-attenuated vaccines, such as the oral polio vaccine (OPV).

Thus, the disclosed viruses that are impaired or unable to reactivate from latency provide a substantial improvement over unimpaired viruses in their safety profile. The viruses can be used to raise an immune response against one or more autologous antigens (e.g., against the virus itself), and/or against one or more homologous or heterologous antigens encoded by a recombinant virus (e.g., serving as a vector for the homologous or heterologous antigen). As introduced, above, some CMVs including HCMV are capable of superinfection. Thus, the virus can be used over and over again in the same subject, each time delivering the same or different antigens.

A. Methods of Treatment

Methods of vaccinating or otherwise inducing an immune response against a desired antigen are provided. The methods typically include administering a subject in need thereof an effective amount of a virus impaired or unable reactivate in cells and tissues. Typically the virus has one or more mutations in the iP1 promoter, or its homolog; the iP2 promoter, or its homolog; or a combination thereof that reduces or stops activity of one or both promoters. Because the activity of the these promoters is important for reactivation of latent virus, the virus administered as part of the vaccine will have reduced reactivity compared to a virus in which iP1, iP2, or both are intact or otherwise fully functional.

1. Immunogen a. Vaccines Against the Virus Itself

In some embodiments, the virus does not encode a heterologous antigen. In such embodiments, the virus is typically administered to a subject in need of immunizing against future infection or reactivation of the virus itself (e.g. a autologous). Administration of the virus to a subject in need thereof can elicit and preferably maintain a protective immune response (e.g., high level cellular and/or humoral immune responses) that can treat and/or decrease the likelihood of an infection by the virus or pathology associated with such an infection in a patient.

For example, in some embodiments, the disclosed CMVs are used to immunize a subject in need thereof against CMV. Early live attenuated vaccines to HCMV were generated over 30 years ago through serial passage of virus in tissue culture. Though live attenuated HCMV vaccines are currently entering clinical trials, such vaccines could reactivate and cause disease in immune-compromised adults. Incorporating mutations in the IE promoters could prevent vaccine strains from reactivating, and thus enhance vaccine safety. Such mutations would not limit the ability to cultivate the vaccine strain, or limit antigen presentation following vaccination, since recombinants lacking the IE promoters express the full complement of HCMV proteins and replicate efficiently in fibroblasts (Arend, et al., *Journal of Virology*, 90, 8855-8865 (2016)).

b. Vaccines Against a Heterologous Antigen

In some embodiments, the virus is a recombinant virus that encodes one or more homologous or heterologous antigens, such as a pathogen-specific antigen or a tumor antigen. Typically the genome of the viral vectors includes a nucleic acid sequence encoding the one or more heterologous antigens. Administration of the virus to a subject in need thereof can elicit and preferably maintain a protective immune response (e.g., high-level cellular and/or humoral immune responses) specific for the encoded antigen. In some embodiments, administration of such viruses can result in an immune response against the virus itself (e.g., against autologous antigen(s)) as discussed above, as well as the heterologous antigen.

Such viruses can be referred to as viral vectors or vaccine vectors. Exemplary antigens are discussed above.

CMVs have shown promise as vaccine vectors, particular in view of their ability to superinfect. For example, RhCMV has the ability to re-infect seropositive rhesus monkeys in spite of the presence of a significant anti-RhCMV immune response. In contrast, most current HIV vaccine vectors (i.e., pox and adenovirus-based vectors) are compromised by anti-vector immunity allowing for only a single effective use of these vaccine platforms. This property of CMV vectors can be attributed to the extensive repertoire of immune evasion genes encoded by this virus (Hansen, et al., *Science*, 328:102-106 (2010)). Another further advantage of CMV-based vectors is the potential to insert large cassettes expressing antigens in which theoretically over 50 kb of the viral genome can be replaced with foreign DNA. Together, these characteristics of CMV-based vaccine vectors have enabled development of vaccines that are capable of inducing a robust TEM response to multiple antigens and completely controlling viral replication rhesus monkeys prior to the establishment of progressive, systemic infection. See, e.g., U.S. Pat. No. 9,546,355 and Hansen, et al., *Nature Medicine*, 15(3):293-299 (2011).

Historically a major concern of using a fully replication competent HCMV as a vaccine vector is one of safety. However, the disclosed viruses having reduced or absent ability reactivate from latency can alleviate these concerns.

2. Adjuvant

In some embodiments, the virus is administered to the subject in need thereof in combination with an adjuvant. The adjuvant can be administered as part of the same pharmaceutical composition as the virus, or the virus and adjuvant can be administered separately.

The adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic).

Adjuvants may be TLR ligands. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolin amines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

The adjuvant can also be oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-gamma), macrophage colony stimulating factor, and tumor necrosis factor.

B. Pharmaceutical Compositions

Viruses are typically administered to a patient in need thereof in a pharmaceutical composition. Pharmaceutical compositions containing virus may be for systemic or local administration. Dosage forms for administration by parenteral (intramuscular (IM), intraperitoneal (IP), intravenous (IV) or subcutaneous injection (SC)), or transmucosal (nasal, vaginal, pulmonary, or rectal) routes of administration can be formulated. In the most preferred embodiments, the immunizing virus is delivered peripherally by intranasally or by intramuscular injection, and the therapeutic virus is delivered by local injection.

1. Effective Amounts

As generally used herein, an "effective amount" is that amount which is able to induce a desired result in a treated subject. The desired results will depend on the disease or condition to be treated. The amount can be effective to reduce infection or cancer, ameliorating the symptoms of disease associated with infection or cancer, and/or shortening the length and/or severity of infection or cancer, or to reduce the likelihood of infection or cancer. Typically the composition is administered in an effective amount to induce an immune response against a one or more autologous, homologous, and/or heterologous antigens encoded by the virus. For example, an effective amount of virus generally results in production of antibody and/or activated T cells that kill or limit proliferation of or infection by a virus or other pathogen, or cancer cells.

2. Dosages

The precise dosage will vary according to a variety of factors such as subject-dependent variables (e.g., age, immune system health, etc.), the disease, and the treatment being effected. Appropriate dosages can be determined by a person skilled in the art, considering the therapeutic context, age, and general health of the recipient. The selected dosage depends upon the desired therapeutic effect, on the route of administration, and on the duration of the treatment desired. In determining the effective amount of the virus to be administered for the treatment or prophylaxis, the physician may evaluate circulating plasma levels of virus, progression of disease, and/or the production of existing antibodies against the antigen(s). Active virus can also be measured in terms of plaque-forming units (PFU). A plaque-forming unit can be defined as areas of cell lysis (CPE) in monolayer cell culture, under overlay conditions, initiated by infection with a single virus particle. Generally dosage levels of virus between $10^2$ and $10^{12}$ pfu are administered to humans. In different embodiments, the dosage range is from $10^4$ to $10^{10}$ pfu, $10^5$ to $10^9$ pfu, $10^6$ to $10^8$ pfu, or any dose within these stated ranges. When more than one vaccine is to be administered (i.e., in combination vaccines), the amount of each vaccine agent can be within their described ranges.

Virus is typically administered in a liquid suspension, in a volume ranging between 10 µL and 100 mL depending on the route of administration. Vaccine volumes commonly practiced range from 0.1 mL to 0.5 mL. Generally, dosage and volume will be lower for local injection as compared to systemic administration or infusion.

The vaccine composition can be administered in a single dose or a multi-dose format. Vaccines can be prepared with adjuvant hours or days prior to administrations, subject to identification of stabilizing buffer(s) and suitable adjuvant composition. Typically the dose will be 100 µl administered locally in multiple doses, while systemic or regional administration via subcutaneous, intramuscular, intra-organ, or intravenous administration can be from for example, 10 to 100 mL.

The pharmaceutical composition typically includes a carrier, preferably a pharmaceutically acceptable carrier. The term "carrier" refers to an organic or inorganic ingredient, natural or synthetic, with which the active ingredient is combined to facilitate the application. The term "pharmaceutically acceptable" means a non-toxic material that does not interfere with the effectiveness of the biological activity of the active ingredients. The term "pharmaceutically-acceptable carrier" means one or more compatible solid or liquid fillers, diluents or encapsulating substances which are suitable for administration to a human or other vertebrate animal Pharmaceutical compositions may be formulated in a conventional manner using one or more physiologically acceptable carriers including excipients and auxiliaries which facilitate processing of the active compounds into preparations which can be used pharmaceutically. The compositions may be administered in combination with one or more physiologically or pharmaceutically acceptable carriers, thickening agents, co-solvents, adhesives, antioxidants, buffers, viscosity and absorption enhancing agents and agents capable of adjusting osmolarity of the formulation. Proper formulation is dependent upon the route of administration chosen. If desired, the compositions may also contain minor amount of nontoxic auxiliary substances such as wetting or emulsifying agents, dyes, pH buffering agents, or preservatives. The formulations should not include membrane disrupting agents which could kill or inactivate the virus.

3. Formulations for Local or Parenteral Administration

In some embodiments, compositions including virus disclosed herein, are administered in an aqueous solution, by parenteral injection. Injection includes, but it not limited to, local, intratumoral, intravenous, intraperitoneal, intramuscular, or subcutaneous. The formulation may also be in the form of a suspension or emulsion. In general, pharmaceutical compositions are provided including effective amounts of virus, and optionally include pharmaceutically acceptable diluents, preservatives, solubilizers, emulsifiers, adjuvants and/or carriers. Such compositions include diluents such as sterile water, buffered saline of various buffer content (e.g., Tris-HCl, acetate, phosphate), pH and ionic strength; and optionally, additives such as anti-oxidants (e.g., ascorbic acid, sodium metabisulfite), and preservatives and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. A preferred solution is phosphate buffered saline or sterile saline.

4. Formulations for Mucosal Administration

In some embodiments, the compositions are formulated for mucosal administration, such as through nasal, pulmonary, or buccal delivery.

Mucosal formulations may include one or more agents for enhancing delivery through the nasal mucosa. Agents for enhancing mucosal delivery are known in the art, see, for example, U.S. Patent Application No. 20090252672 to Eddington, and U.S. Patent Application No. 20090047234 to Touitou. Acceptable agents include, but are not limited to, chelators of calcium (EDTA), inhibitors of nasal enzymes (boro-leucin, aprotinin), inhibitors of muco-ciliary clearance (preservatives), solubilizers of nasal membrane (cyclodextrin, fatty acids, surfactants) and formation of micelles (surfactants such as bile acids, Laureth 9 and taurodehydrofusidate (STDHF)). Compositions may include one or more absorption enhancers, including surfactants, fatty acids, and chitosan derivatives, which can enhance delivery by modulation of the tight junctions (TJ) (B. J. Aungst, et al., *J. Pharm. Sci.* 89(4):429-442 (2000)). In general, the optimal absorption enhancer should possess the following qualities: its effect should be reversible, it should provide a rapid permeation enhancing effect on the cellular membrane of the mucosa, and it should be non-cytotoxic at the effective concentration level and without deleterious and/or irreversible effects on the cellular or virus membrane. Intranasal compositions maybe administered using devices known in the art, for example a nebulizer.

C. Methods of Administration and Response Monitoring

The disclosed viruses can be formulated and administered to a patient using the guidance provided herein along with techniques well known in the art. Guidelines for pharmaceutical administration in general are provided in, for example, Vaccines Eds. Plotkin and Orenstein, W.B. Sanders Company, 1999; Remington's Pharmaceutical Sciences 20th Edition, Ed. Gennaro, Mack Publishing, 2000; and Modern Pharmaceutics 2.sup.nd Edition, Eds. Banker and Rhodes, Marcel Dekker, Inc., 1990.

Various factors may be considered when determining the frequency, dosage, duration, and number of administrations of immunizing virus. Vaccines can be administered by different routes such as subcutaneous, intramuscular, intravenous, mucosal, parenteral, transdermal or intradermal. Subcutaneous and intramuscular administration can be performed using, for example, needles or jet-injectors. In an embodiment, the vaccine of the invention is administered intramuscularly. Transdermal or intradermal delivery can be accomplished through intradermal syringe needle injection, or enabling devices such as micron-needles or micron array patches.

The compositions described herein may be administered in a manner compatible with the dosage formulation, and in such amount as is immunogenically-effective to treat and/or reduce the likelihood of infection or cancer. The timing of doses depends upon factors well known in the art. After the initial administration, one or more additional doses may be administered to maintain and/or boost antibody titers and T cell immunity. Additional boosts may be required to sustain the protective levels of immune responses, reflected in antibody titers and T cell immunity such as ELISPOT.

For combination vaccinations, each of the immunogens can be administered together in one composition or separately in different compositions. Two or more viruses each encoding one or more autologous, homologous, and/or heterologous antigens can be administered concurrently with each and/or with other immunogens. The term "concurrently" is not limited to the administration of the therapeutic agents at exactly the same time, but rather it is meant that the viruses described herein alone, together, or further in combination with other immunogens can be administered to a subject in a sequence and within a time interval such that the they can act together to provide an increased benefit than if they were administered otherwise. For example, each therapeutic agent may be administered at the same time or sequentially in any order at different points in time; however, if not administered at the same time, they should be administered sufficiently close in time so as to provide the desired therapeutic effect. Each therapeutic agent can be administered separately, in any appropriate form and by any suitable route.

The subject's adaptive immune response can be monitored to assess the effectiveness of the immunization. Methods of measuring adaptive immune activation are known in the art and include antibody profiling, serum analysis for changes in levels of antibodies, cytokines, chemokines, or other inflammatory molecules, and cell counts and/or cell profiling using extracellular markers to assess the numbers and types of immune cells such as B cells and T cells.

Animal models known in the art can be used to assess the protective effect of administration of the virus. In some embodiments, immune sera from individuals administered the virus can be assayed for neutralizing capacity, including but not limited to, blockage of viral attachment or entry to a host cell. In other embodiments, T cells from individuals administered the virus can be assayed for cytokine producing capacity including, but not limited to, interferon gamma, in the presence of an antigen of interest. Animal challenge models can also be used to determine an immunologically effective amount of immunogen.

Viral neutralization refers to viral specific antibodies capable of interrupting viral entry and/or replication in cultures. A common assay for measuring neutralizing activities is viral plaque reduction assay. For example, neutralization assays can be serum titrations that can block virus entering cells. NT50 titers are defined as reciprocal serum dilutions to block 50% of input virus in viral neutralization assays. NT50 titers are obtained from nonlinear logistic four-parameter curve fitting.

D. Subjects to be Treated

In general, the disclosed methods are for use in vaccination. As described above, virus can express one or more autologous, homologous, or heterologous immunogenic antigens. Expression of these antigens in a patient in need thereof presents the antigen to the immune system and provokes an immune response. Vaccines can be administered prophylactically or therapeutically. Vaccines can also be administered according to a vaccine schedule. A vaccine schedule is a series of vaccinations, including the timing of all doses. Many vaccines require multiple doses for maximum effectiveness, either to produce sufficient initial immune response or to boost response that fades over time. Vaccine schedules are known in the art, and are designed to achieve maximum effectiveness. The adaptive immune response can be monitored using methods known in the art to measure the effectiveness of the vaccination protocol.

In some embodiments, the subject is an animal, preferably a mammal, more preferably a human. In some embodiments, prophylactic treatment provides sufficient protective immunity to reduce the likelihood or severity of one or more of an infection, including primary infections; recurrent infections (i.e., those resulting from reactivation of latent virus); and super-infections (i.e., those resulting from an infection with a different stain of virus than previously experienced by the patient); or the development of cancer. Therapeutic treatment can be performed to reduce the severity of an infection; or decrease the likelihood/severity of a recurrent or super-infection of the virus; or reduce the likelihood of developing a caner.

Treatment can be performed using a pharmaceutical composition including the virus as described herein. Pharmaceutical compositions can be administered to the general population, especially to those persons at an increased risk of infection (either primary, recurrent or super) or cancer or for whom infection or cancer would be particularly problematic (such as immunocompromised individuals, transplant patients or pregnant women). In one embodiment, females of childbearing age, especially early adolescent females, are vaccinated to decrease the likelihood of infection (either primary, recurrent or super) during pregnancy.

Those in need of treatment include those already with an infection or cancer, as well as those prone to have an infection or cancer, or in which a reduction in the likelihood of infection or cancer is desired. Treatment can ameliorate the symptoms of disease associated with infection or cancer and/or shorten the length and/or severity of infection or cancer, including infection due to reactivation of latent virus.

Persons with an increased risk of infection (either primary, recurrent or super) include patients with weakened immunity or patients facing therapy leading to a weakened immunity (e.g., undergoing chemotherapy or radiation therapy for cancer or taking immunosuppressive drugs). As used herein, "weakened immunity" refers to an immune system that is less capable of battling infections because of an immune response that is not properly functioning or is not functioning at the level of a normal healthy adult. Examples of patients with weakened immunity are patients that are infants, young children, elderly, pregnant or a patient with a disease that affects the function of the immune system such as HIV infection or AIDS.

1. Infections

In some embodiments, the virus encodes one or more viral, bacterial, or parasitic antigens such as those discussed above. Viruses encoding a viral, bacterial, or parasitic antigen can be used to protect or treat a subject from a disease or disorder caused by the virus, bacteria, or parasite that expresses the antigen or from which the antigen was derived. Thus, in some embodiments the subject has or may develop an infection.

Representative infections that can be treated, include but are not limited for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) viral infections. Pharmaceutical formulations of PD-1 antagonist compositions can also be administered to treat systemic viral diseases, including, but not limited to, AIDS, influenza, the common cold, or encephalitis.

Representative infections also includes infections cause by microoganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus,* Hemophilus influenza type B (HIB), *Histoplasma, Hyphomicrobium, Legionella, Leishmania, Leptspirosis, Listeria,* Meningococcus A, B and C, *Methanobacterium, Micrococcus, Myobacterium, Mycoplasma, Myxococcus, Neisseria, Nitrobacter,* Oscillatoria, Prochloron, *Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Plasmodium vivax, Trypanosoma brucei, Entamoeba histolytica, Toxoplasma gondii, Trichomonas vaginalis* and *Schistosoma mansoni.*

2. Cancer and Tumor Therapy

Viruses encoding a cancer antigen can be used to protect or treat a subject from a cancer that expresses the antigen or from which the antigen was derived. Thus, in some embodiments the subject has or may develop a cancer.

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth Malignant tumors which may be treated are classified herein according to the embryonic origin of the tissue from which the tumor is derived. Carcinomas are tumors arising from endodermal or ectodermal tissues such as skin or the epithelial lining of internal organs and glands. The disclosed compositions are particularly effective in treating carcinomas. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers such as vascular cancer such as multiple myeloma, adenocarcinomas and sarcomas, of bone, bladder, brain, breast, cervical, colo-rectal, esophageal, kidney, liver, lung, nasopharangeal, pancreatic, prostate, skin, stomach, and uterine. In some embodiments, the disclosed compositions are used to treat multiple cancer types concurrently. The compositions can also be used to treat metastases or tumors at multiple locations.

E. Combination Therapies

In some embodiments, the virus is administered in combination with a conventional therapeutic agent used for treatment of the disease or condition being treated. Conventional therapeutics agents are known in the art and can be determined by one of skill in the art based on the disease or disorder to be treated. For example, if the disease or condition is cancer, the virus can be co-administered with a chemotherapeutic drug; or if the disease or condition is a bacterial infection, the conjugates can be co-administered with an antibiotic.

For example, administration of the disclosed viruses may also be coupled with surgical, radiologic, other therapeutic approaches to treatment of tumors.

1. Surgery

The disclosed compositions and methods can be used as an adjunct to surgery. Surgery is a common treatment for many types of benign and malignant tumors. As it is often not possible to remove all the tumor cells from during surgery, the disclosed compositions containing oncolytic virus are particularly useful subsequent to resection of the primary tumor mass, and would be able to infect and destroy even dispersed tumor cells.

In a preferred embodiment, the disclosed compositions and methods are used as an adjunct or alternative to neurosurgery. The compositions are particularly well suited to treat areas of the brain that is difficult to treat surgically, for instance high grade tumors of the brain stem, motor cortex, basal ganglia, or internal capsule. High grade gliomas in these locations are generally considered inoperable. An additional situation where an oncolytic virus may be helpful is in regions where the tumor is either wrapped around critical vasculature, or in an area that is difficult to treat surgically.

2. Therapeutic Agents

The viral compositions can be administered to a subject in need thereof alone or in combination with one or more additional therapeutic agents selected based on the condition, disorder or disease to be treated. A description of the various classes of suitable pharmacological agents and drugs may be found in Goodman and Gilman, *The Pharmacological Basis of Therapeutics*, (11th Ed., McGraw-Hill Publishing Co.) (2005).

Additional therapeutic agents include conventional cancer therapeutics such as chemotherapeutic agents, cytokines, chemokines, and radiation therapy. The majority of chemotherapeutic drugs can be divided into: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

Preferred chemotherapeutics will affect tumors or cancer cells, without diminishing the activity of the virus. For example, in a preferred embodiment, the additional therapeutic agent inhibits proliferation of cancer cells without affecting targeting, infectivity, or replication of the virus.

IV. Viral Promoter Compositions and Methods of Use Thereof

A. Compositions for Transgene Expression

Nucleic acid compositions including an intronic promoter alone or in combination of additional expression controls sequences operably linked to a transgene are also provided.

1. Expression Control Sequences

The compositions typically include a disclosed intronic promoter alone or in combination with additional expression control sequences.

Intronic promoter sequences are provided above and elsewhere herein and include, but are not limited to, the iP1 promoter, iP2 promoter, promoters homologous thereto, each of SEQ ID NOS:1-6, and functional fragments and variants thereof including, for example, nucleic acids with at least 60, 70, 80, 90, 95, 96, 97, 98, or 99% sequence identity to any one or more of SEQ ID NOS:1-6 that can induce or otherwise initiate expression of a gene.

The compositions can include additional expression control sequences including, but not limited to, enhancers, and transcription terminating regions.

Bring a coding sequence under the control of a promoter typically includes positioning the translation initiation site of the translational reading frame of the polypeptide between one and about fifty nucleotides downstream of the promoter Enhancers provide expression specificity in terms of time, location, and level. Unlike promoters, enhancers can function when located at various distances from the transcription site. An enhancer also can be located downstream from the transcription initiation site.

A coding sequence (e.g., a transgene(s)) is "operably linked" and "under the control" of expression control sequences in a cell when RNA polymerase is able to transcribe the coding sequence into RNA.

In some embodiments, the composition further includes 5' and/or 3' untranslated regions, a polyA tail, or a combination thereof.

2. Transgene

The disclosed compositions typically include one or more transgenes heterologous to the promoter. In some embodiments, the promoter is engineered into to a cell such that it is operably linked to an endogenous cellular gene. In some embodiments, the nucleic acid that is introduced into a cell include both the promoter and the transgene, which can be endogenous or heterologous to the cells. In some embodiments the transgene sequence encodes one or more proteins, functional nucleic acids, gene editing compositions, or a combination thereof. The transgene can be monocistronic or polycistronic. In some embodiments, the transgene is multigenic.

a. Polypeptide of Interest

The transgene(s) can encode one or more polypeptides of interest. The polypeptide can be any polypeptide. For example, the polypeptide of interest encoded by the transgene can be a polypeptide that provides a therapeutic or prophylactic effect to an organism or that can be used to diagnose a disease or disorder in an organism.

The therapeutic protein can, for example, (a) replace a protein that is deficient or abnormal; (b) augment an existing pathway; (c) provide a new function or activity; (d) interfere with a molecule or organism (Dimitrov, et al., *Methods Mol Biol,* 899:1-26 (2012)). Therapeutic proteins can also be grouped based on their molecular types that include antibody-based drugs, Fc fusion proteins, anticoagulants, blood factors, bone morphogenetic proteins, engineered protein scaffolds, enzymes, growth factors, hormones, interferons, interleukins, and thrombolytics. They can also be classified based on their molecular mechanism of activity as (a) binding non-covalently to target, e.g., mAbs; (b) affecting covalent bonds, e.g., enzymes; and (c) exerting activity without specific interactions, e.g., serum albumin.

In some embodiments, the transgene encodes, for example, an antigen, CD4+ T-cell epitope, cytokine, antibody, immunologic danger signaling molecule, enzyme, growth factor, growth inhibitor, hormone, hormone antagonist, or immunomodulator (e.g., ligands that bind to Toll-Like Receptors (including but not limited to CpG oligonucleotides) to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells).

In some embodiments, the transgene encodes an antigen, such one of the antigens discussed above.

Exemplary cytokines include, but are not limited to, granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interferon alpha (IFNα), interferon beta (IFNβ), interferon gamma (IFNγ), and IGIF, and variants and fragments thereof. In the most preferred embodiment, the therapeutic protein is an interferon, such as interferon alpha.

Suitable chemokines include, but are not limited to, an alpha-chemokine or a beta-chemokine, including, but not limited to, a C5a, interleukin-8 (IL-8), monocyte chemotactic protein 1alpha (MIP1α), monocyte chemotactic protein 1 beta (MIP1β), monocyte chemoattractant protein 1 (MCP-1), monocyte chemoattractant protein 3 (MCP-3), platelet activating factor (PAFR), N-formyl-methionyl-leucyl-[$^3$H]phenylalanine (FMLPR), leukotriene B4, gastrin releasing peptide (GRP), RANTES, eotaxin, lymphotactin, IP10, I-309, ENA78, GCP-2, NAP-2 and MGSA/gro, and variants and fragments thereof.

For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism.

In some embodiments, the composition includes a reporter gene. Reporter genes are typically genes that are not present or expressed in the host cell. The reporter gene typically encodes a protein which provides for some phenotypic change or enzymatic property. Examples of such genes are provided in K. Weising et al. *Ann. Rev. Genetics,* 22, 421 (1988). Preferred reporter genes include glucuronidase (GUS) gene and GFP genes.

b. Functional Nucleic Acids

The transgene(s) can encode a functional nucleic acid. Functional nucleic acids typically inhibit the transcription, translation or another function of a target nucleic acid (e.g., gene or RNA).

Functional nucleic acids are nucleic acid molecules that have a specific function, such as binding a target molecule or catalyzing a specific reaction. Functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the target polypeptide itself. Functional nucleic acids are often designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place. Therefore the compositions can include one or more functional nucleic acids designed to reduce expression or function of a target protein.

Methods of making and using vectors for in vivo expression of the described functional nucleic acids such as antisense oligonucleotides, siRNA, shRNA, miRNA, EGSs, ribozymes, and aptamers are known in the art.

c. Gene Editing Molecules

In certain embodiments, the transgene(s) encode one or more gene editing moieties, or components capable of binding to gene editing moieties. Exemplary gene-editing moieties that can be included within or bound to nucleic acid nanoparticles are CRISPR RNAs, for the gene editing through the CRISPR/Cas system.

CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, *Science,* 15:339(6121):819-823 (2013) and Jinek, et al., *Science,* 337(6096):816-21 (2012)). By transfecting a cell with the required elements including a Cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423, which are specifically incorporated by reference herein in their entireties. For example, in some embodiments, the transgene encodes g- or sgRNA, a Cas nuclease, or a combination thereof.

In some embodiments, the transgene encodes a zinc finger nuclease (ZFN). ZFNs are typically fusion proteins that include a DNA-binding domain derived from a zinc-finger protein linked to a cleavage domain. The most common cleavage domain is the Type IIS enzyme FokI. FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA*. 91:883-887 (1994a); Kim et al. *J. Biol. Chem.* 269:31,978-31,982 (1994b). One or more of these enzymes (or enzymatically functional fragments thereof) can be used as a source of cleavage domains.

In some embodiments, the transgene encodes a transcription activator-like effector nuclease (TALEN). TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats. General design principles for TALE binding domains can be found in, for example, WO 2011/072246.

3. Vectors

In some embodiments, the composition is an expression vector including a disclosed promoter alone or in combination with additional expression control sequences. The vector can include a transgene, a cloning site (e.g., a multicloning site) for incorporation of a transgene of interest, or a combination thereof. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc epitope, hemagglutinin epitope, Flag™ epitope tag (Kodak, New Haven, Conn.), maltose E binding protein and protein A.

The composition can include a selectable marker. The selectable marker or markers can be effective in eukaryotic cells, prokaryotic cells, or a combination thereof. In some embodiments, the marker is a drug resistance selection marker. This selectable marker gene can encode a factor necessary for the survival or growth of transformed host cells grown in a selective culture medium. Typical selection genes encode proteins that confer resistance to antibiotics or other toxins, e.g., ampicillin, neomycin, methotrexate, kanamycin, gentamicin, Zeocin, or tetracycline, complement auxotrophic deficiencies, or supply critical nutrients withheld from the media.

B. Methods of Use

The disclosed compositions for gene expression can be used for express the transgene in a cell or cells of interest. Typically, the composition is transform, transfected, or otherwise introduced into a cell in an effective amount to be transcribed, and in the case of proteins, translated to effect a desired result. For example, the compositions can (a) replace a protein that is deficient or abnormal; (b) augment an existing pathway; (c) provide a new function or activity; (d) interfere with a molecule or organism. In some embodiments, the transgene replaces or supplements a mutated gene that causes disease with a healthy copy of the gene; reduces or inactivates expression of a mutated gene that is functioning improperly, or introduces a new gene into the cells.

The compositions can be delivered to cells in vitro, ex vivo, or in vivo. Nucleic acids can be transfected into mammalian cells by techniques including, for example, calcium phosphate co-precipitation, DEAE-dextran-mediated transfection, lipofection, electroporation, or microinjection. Prokaryotic cells can be transformed with nucleic acids by, for example, electroporation or calcium chloride mediated transformation.

Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In some embodiments, expression vectors containing nucleic acids encoding the transgene are transfected into cells that are administered to a subject in need thereof.

One approach includes nucleic acid transfer into primary cells in culture followed by autologous transplantation of the ex vivo transformed cells into the host, either systemically or into a particular organ or tissue.

In vivo nucleic acid therapy can be accomplished by direct transfer of a functionally active DNA into mammalian somatic tissue or organ in vivo.

Nucleic acids may also be administered in vivo by viral means. Nucleic acid molecules encoding polypeptides or fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

In addition to virus- and carrier-mediated gene transfer in vivo, physical means well-known in the art can be used for direct transfer of DNA, including administration of plasmid DNA and particle-bombardment mediated gene transfer.

In some embodiments, the transgene is expressed in an effective amount to reduce one or more symptoms of target diseases or disorder. Diseases and disorders include, but are not limited to, cancers, immune disorders, infections, and genetic diseases and disorders.

Exemplary genetic diseases include cystic fibrosis, alpha- and beta-thalassemias, sickle cell anemia, Marfan syndrome, fragile X syndrome, Huntington's disease, and hemochromatosis, however, list is non-limiting and many other diseases are known in the art.

Target cells include, but are not limited to, hematopoietic stem cells, mesenchymal stem cells, epithelial stem cells, and muscle satellite cells, or differentiated cells of human tissues, including, but not limited to, red blood cells, white blood cells including lymphocytes, platelets, stromal cells, fat cells, bone cells including osteoclasts, epithelial tissue including skin cells, muscle tissue including smooth muscle, skeletal muscle, and cardiac muscle, vascular tissue including endothelial cells, liver tissue including hepatocytes, and nervous tissue including neurons.

In preferred embodiments, the cells are hematopoietic cells. Hematopoietic cells are an attractive target for gene therapy because of the relative ease to which they can be acquired from children and adults, and because of the self-renewing potential of hematopoietic stem cells (HSCs). Transfer of an expression vector into relatively few HSC results in repopulation of most of the hematopoietic compartment and lineages. Promoters that can drive enduring gene expression in a cell-type specific manner are of importance to successful gene expression, however, gene expression from viral promoters is often silenced in HSCs. In contrast, the disclosed intronic promoters are expressed in hematopoietic cells making then an attractive candidate for gene expression in hematopoietic based-therapies.

In some embodiments, the hematopoietic cells such as HSCs or progenitor cells are transformed or transfected in vitro or ex vivo, and then administered in an effective amount to a subject in need thereof.

In some embodiments, the subject receive a hematopoietic cell transplantation (HCT). HCT typically refers to the intravenous infusion of hematopoietic stem and progenitor cells. The methods can establish marrow and immune function in patients with a variety of acquired and inherited malignant and nonmalignant disorders. These include hematologic malignancies (e.g., leukemia, lymphoma, and myeloma), nonmalignant acquired bone marrow disorders (eg, aplastic anemia), and genetic diseases associated with abnormal hematopoiesis and function (e.g., thalassemia, sickle cell anemia, and severe combined immunodeficiency). HCT is also used in the support of patients undergoing high-dose chemotherapy for the treatment of certain solid tumors for whom hematologic toxicity would otherwise limit drug administration (germ cell tumors, soft tissue sarcomas, and neuroblastoma).

V. Kits

Dosage units include virus in a pharmaceutically acceptable carrier for shipping and storage and/or administration. Active virus should be shipped and stored using a method consistent with viability such as in cooler containing dry ice so that cells are maintained below 4° C., and preferably below −20° C. Components of the kit may be packaged individually and can be sterile. In one embodiment, a pharmaceutically acceptable carrier containing an effective amount of virus is shipped and stored in a sterile vial. The sterile vial may contain enough virus for one or more doses. Virus may be shipped and stored in a volume suitable for administration, or may be provided in a concentrated titer that is diluted prior to administration. In another embodiment, a pharmaceutically acceptable carrier containing an effective amount of virus can be shipped and stored in a syringe.

Typical concentrations of viral particles in the sterile saline, phosphate buffered saline or other suitable media for the virus is in the range of $10^8$ to $10^9$ with a maximum of $10^{12}$. Dosage units should not contain membrane disruptive agents nor should the viral solution be frozen and dried (i.e., lyophilized), which could kill the virus.

Kits containing syringes of various capacities or vessels with deformable sides (e.g., plastic vessels or plastic-sided vessels) that can be squeezed to force a liquid composition out of an orifice are provided. The size and design of the syringe will depend on the route of administration. For example, in one embodiment, a syringe for administering virus intratumorally, is capable of accurately delivering a smaller volume (such as 1 to 100 µl). Typically, a larger syringe, pump or catheter will be used to administer virus systemically. Any of the kits can include instructions for use.

EXAMPLES

Example 1: Intronic Promoters are Important for Reactivation of Latent HCMV

Materials and Methods

THP-1 cells were infected in an undifferentiated state. At 5 dpi, cells were treated with phorbol ester (TPA) to induce differentiation/reactivation or DMSO as a vehicle control (latent). The accumulation of MIEP-derived transcripts (amplicon in exon 1) or IE1 and IE2 (amplicons span exons 3/4 and 3/5, respectively) were measured by RT-qPCR relative to the housekeeping gene, H6PD, over the indicated time course. IE1 and IE2 protein accumulation were analyzed by immunoblotting over the time course both prior to and following TPA or DMSO treatment.

Basal activity of iP1 and iP2 was measured using luciferase reporter constructs (FIG. 4A). The activity of each reporter was measured in transfected HeLa cells.

Expression from the MIE locus is controlled by the distal promoter (dP), the major immediate early promoter (MIEP), and two intronic MIE promoters (iP1 and iP2). Transcripts from the four promoters differ in their 5' ends. Primer positions were used to distinguish transcripts derived from dP or MIEP, iP1, or iP2.

To determine the role for iP1 and iP2 in reactivation, recombinant viruses were generated with large deletions of iP1 (ΔiP1) or iP2 (ΔiP2) in the low passage HCMV strain TB40/E bacterial artificial chromosome (BAC). Each deletion is −450 to +50 bp relative to the TSS.

The parent sequence was GenBank: EF999921.1, VRL 26 Jul. 2016, Human herpesvirus 5 strain TB40/E clone TB40-BAC4, complete sequence. Fragments of the viral genome spanning the region corresponding to intron A in the control (TB40EE) and deletion strains are provided as SEQ ID NOS:1 and 7-9 and aligned in FIG. 11.

```
TB40E WT virus
                                           (SEQ ID NO: 1)
GTAAGTACCGCCTATAGACTCTATAGGCCCACCCCCTTGGCTTCTTATG

CATGCTATACTGTTTTGGCTTGGGGTCTATACACCCCCGCTTCCTTAT

GCTATAGGTGATGGTATAGCTTAGCCTATAGGTGTGGGTTATTGACCAT
```

-continued
TATTGACCACTCCCCTATTGGTGACGATACTTTCCATTACTAATCCATA

ACATGGCTCTTTGCCACAACTCTCTTTATTGGCTATATGCCAATACTCT

GTCCTTCAGAGACTGACACGGACTCTGTATTTTTACAGGATGGGGTCCC

ATTTATTATTTACAAATTCACATATACAACAACACCGTCCCCAGTACCC

GCAGTTTTTATTAAACATAGCGTGGGATCTCCACGCGAATCTCGGGTAC

GTGTTCCGGACATGGGCTCTTCTCCGGTAGCGGCGGAGCTTCTACATCC

GAGCCCTGCTCCCATGCCTCCAGCGGCTCATGGTCGCTTGGCAGCTCCT

TGCTCCTAACAGTGGAGGCCAGACTTAGGCACAGCACGATGCCCACCAC

CACCAGTGTGCCGCACAAGGCCGTGGCGGTAGGGTATGTGTCTGAAAAT

GAGCTCGGGGAGCGGGCTTGCACCGCTGACGCATTTGGAAGACTTAAGG

CAGCGGCAGAAGAAGATGCAGGCAGCTGAGTTGTTGTGTTCTGATAAGA

GTCAGAGGTAACTCCCGTTGCGGTGCTGTTAACGGTGGAGGGCAGTGTA

GTCTGAGCAGTACTCGTTGCTGCCGCGCGCGCCACCAGACATAATAGCT

GACAGACTAACAGACTGTTCCTTTCCATGGGTCTTTTCTGCAG

ΔiP1

(SEQ ID NO: 7)
GTAAGTACCGCCTATAGACTCTATAGGCCCAtaacttcgtatagcatac attataCGaAGTTaTTTAAACATAGCGTGGGATCTCCACGCGAATCTCG

GGTACGTGTTCCGGACATGGGCTCTTCTCCGGTAGCGGCGGAGCTTCTA

CATCCGAGCCCTGCTCCCATGCCTCCAGCGGCTCATGGTCGCTTGGCAG

CTCCTTGCTCCTAACAGTGGAGGCCAGACTTAGGCACAGCACGATGCCC

ACCACCACCAGTGTGCCGCACAAGGCCGTGGCGGTAGGGTATGTGTCTG

AAAATGAGCTCGGGGAGCGGGCTTGCACCGCTGACGCATTTGGAAGACT

TAAGGCAGCGGCAGAAGAAGATGCAGGCAGCTGAGTTGTTGTGTTCTGA

TAAGAGTCAGAGGTAACTCCCGTTGCGGTGCTGTTAACGGTGGAGGGCA

GTGTAGTCTGAGCAGTACTCGTTGCTGCCGCGCGCGCCACCAGACATAA

TAGCTGACAGACTAACAGACTGTTCCTTTCCATGGGTCTTTTCTGCAG

ΔiP2

(SEQ ID NO: 8)
GTAAGTACCGCCTATAGACTCTATAGGCCCACCCCCTTGGCTTCTTATG

CATGCTATACTGTTTTTGGCTTGGGGTCTATACACCCCCGCTTCCTTAT

GCTATAGGTGATGGTATAGCTTAGCCTATAGGTGTGGGTTATTGACCAT

TATTGACCACTCCCCTATTGGTGACGATACTTTCCATTACTAATCCATA

ACATGGCTCTTTGCCACAACTCTCTTTATTGGCTATATGCCAATACTCT

GTCCTTCAGAGACTGACACGGACTCTGTATTTTTACAGGATGGGGTCCC

ATTTATTATTTACAAATTCACATATACAACAACACCGTCCCCAGTACCC

GataacttcgtatagcatacattatacgaagttatCTGCCGCGCGCC

ACCAGACATAATAGCTGACAGACTAACAGACTGTTCCTTTCCATGGGTC

TTTTCTGCAG

ΔiP(1 + 2)

(SEQ ID NO: 9)
GTAAGTACCGCCTATAGACTCTATAGGCCCAtaacttcgtatagcatac attatacgaagttatCTGCCGCGCGCCACCAGACATAATAGCTGACA

GACTAACAGACTGTTCCTTTCCATGGGTCTTTTCTGCAG

The lower case bases in SEQ ID NOS:7, 8, and 9 (and the highlighted sequences in FIG. 11A) correspond with residual LoxP from the recombination strategy.

Multi-step growth analysis (MOI of 0.1) of mutant virus replication Virus titers were determined by TCID50.

Undifferentiated THP-1 cells were infected with TB40E WT, ΔiP1 or ΔiP2. At 5 dpi, genome levels were quantitated by PCR (qPCR) using a BAC standard curve. At 5 dpi, THP-1 cells were differentiated with TPA and MIE transcripts originating from the MIEP, iP1, or iP2 were quantified relative to H6PD by RT-qPCR over a time course. Note that the deletion of iP2 removes the primer binding site for detection of iP1. IE1 and IE2 protein levels were analyzed before (latent) and after (reactivation) TPA treatment by immunoblotting. Tubulin was used as a loading control.

Results

Previously, it was believed that reactivation of IE1 and IE2 gene expression during HCMV reactivation required derepression of the MIEP, and that this event is coupled to hematopoietic cell differentiation. Although IE1 and IE2 proteins accumulate during HCMV reactivation, they have not been shown to be derived from transcripts that originate from the MIEP. Therefore experiments were designed to measure the accumulation of MIEP-specific mRNAs, as well as IE1 and IE2 mRNAs during HCMV reactivation in the established THP-1 monocytic cell line model of HCMV latency (Qin, et al., *Journal of Virology*, 87, 9886-9894 (2013), Saffert, et al., *Journal of Virology*, 84, 5594-5604 (2010), O'Connor, et al., *Journal of Virology*, 86, 9854-9865 (2012), Ioudinkova, et al., *Gene*, 384, 120-128 (2006), Albright, et al., *Journal of Virology*, 87, 9802-9812 (2013)). THP-1 cells are an excellent model for HCMV transcriptional silencing and reactivation because they provide a homogeneous population in which reactivation can be synchronized.

Figure 2:
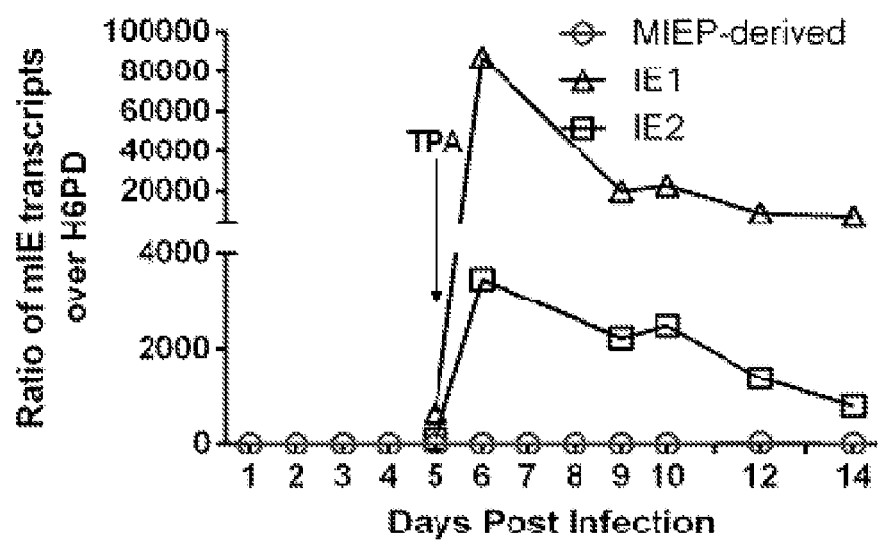
FIG. 2 is a line graph showing MIEP-derived transcripts, IE1, and IE2 expression during reactivation.

Infection of undifferentiated THP-1 cells results in a burst of low level IE1 (72-kDa) and IE2 (86-kDa) protein expression by 1 dpi, followed by a "latency period" during which MIE protein levels become virtually undetectable (FIG. 2). Treating infected THP-1 monocytes with the phorbol ester TPA stimulates cell differentiation and reactivation of quiescent virus, as shown by the robust accumulation of IE1 and IE2 transcripts and proteins. Despite the accumulation of IE1 and IE2 mRNAs (detected using primers spanning exons 3/4 or 3/5, respectively), no transcripts derived from the MIEP (detected using primers binding to sequences near the MIEP transcriptional start site (TSS); see schematic in FIG. 3A).

Next, experiments were design to investigate how does HCMV re-express MIE transcripts during reactivation if the MIEP remains inactive. Previous studies identified two promoters in the MIE transcription unit (FIG. 3A); a distal promoter (dP) active during latency (Kondo, et al., *Proc Natl Acad Sci USA*, 93, 11137-42. (1996)) and the MIEP (Stinski, M. F. & Meier, J. L. in Human Herpesviruses: Biology, Therapy, and Immunoprophylaxis (eds. Arvin, A. et al.) (2007)). Two additional MIE promoters are located within the first intron (intron A) of the classical MIE transcript (Arend, et al., *Journal of Virology*, 90, 8855-8865 (2016)). These promoters are herein referred to as iP1 and iP2, or collectively as "intronic MIE promoters." Transcripts derived from the intronic promoters are capped, and associate with polysomes during the late stage of infection (Arend, et al., *Journal of Virology*, 90, 8855-8865 (2016)). Importantly each of the transcripts encodes full length IE1 (72-kDa) or IE2 (86-kDa) proteins (Arend, et al., *Journal of Virology*, 90, 8855-8865 (2016)). These transcripts differ from MIEP derived transcripts in their 5' untranslated regions due to alternative transcription start site usage (FIG. 3B).

Figure 5:
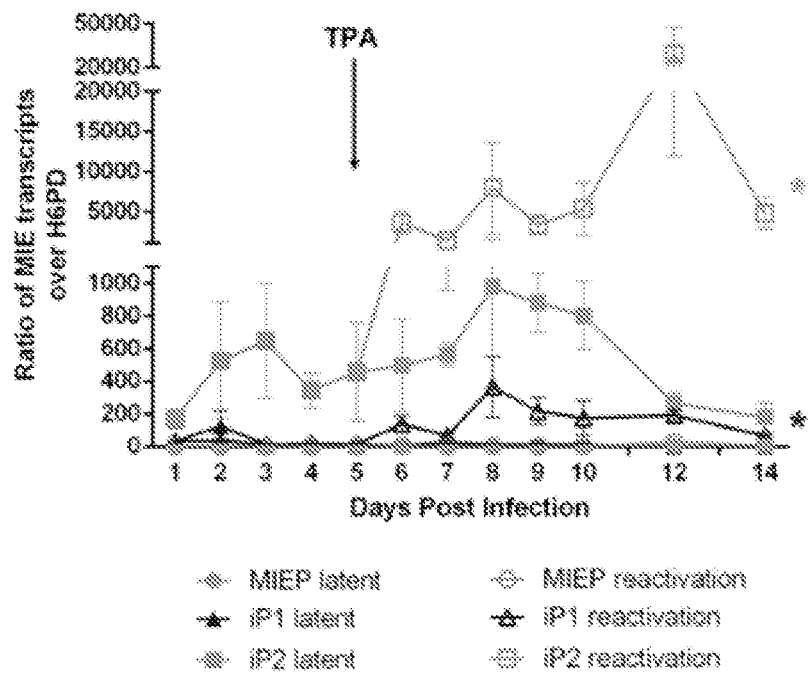
FIG. 5 is a line graph showing the ratio of transcripts originating from iP1, iP2, and MIEP promoters in latency and after reactivation. THP-1 cells were infected with TB40/E WT HCMV (MOI=2) and cultured for 5 days to promote the establishment of latency. At day 5, cells were treated with TPA (to promote macrophage differentiation and viral reactivation) or with a DMSO control. MIEP/dP-, iP1-, and iP2-derived transcript accumulation was quantified relative to the low copy H6PD housekeeping gene by RT-qPCR. Data from three independent biological replicates (each performed in triplicate) is shown; error bars represent standard deviation. Statistical significance was determined by unpaired t test comparing accumulation of each transcript during latency versus reactivation. Welch's correction was used to account for unequal variance (* indicates a p value≤0.05).

A series of reporter constructs containing sequences flanking each intronic transcription start site demonstrate that both iP1 and iP2 sequences have basal promoter activity (FIG. 4B). Using priming sites unique to each transcript (FIG. 3B), reverse transcriptase-quantitative PCR (RT-qPCR) results show that transcripts originating from the iP1 and iP2 promoters increased in abundance following TPA treatment of latently infected THP-1 cells (FIG. 5). In contrast, transcripts originating from either the MIEP or dP were not induced (MIEP primers do not differentiate dP and MIEP-derived transcripts). The increase in iP1 and iP2-derived transcripts correlates with the increase in IE1 and IE2 mRNA levels following reactivation in THP-1 cells. Importantly, RNAseq data from a transcriptome wide study of HCMV latency (Cheng, et al., *Proceedings of the National Academy of Sciences of the United States of America*, 114, E10586-E10595 (2017)) found that the intronic MIE transcripts are expressed in infected CD34+ HPCs. Together, these data strongly indicate the importance of MIE transcripts for HCMV reactivation.

Figure 6A:
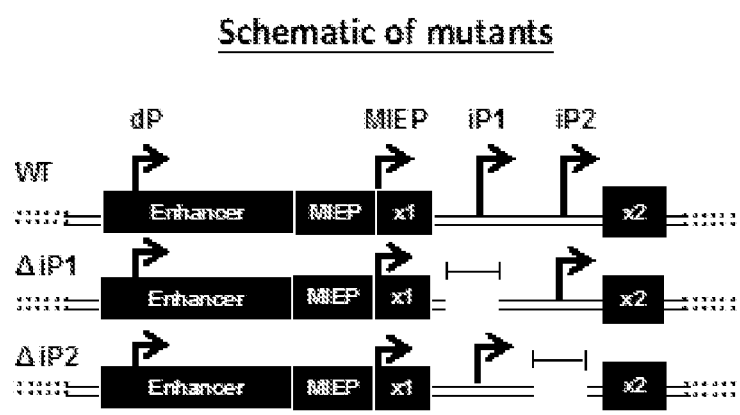
FIG. 6A is a schematic of HCMV mutants illustrating deletions of iP1 or iP2. Each deletion is −450 to +50 bp relative to the TSS.
Figure 6B:
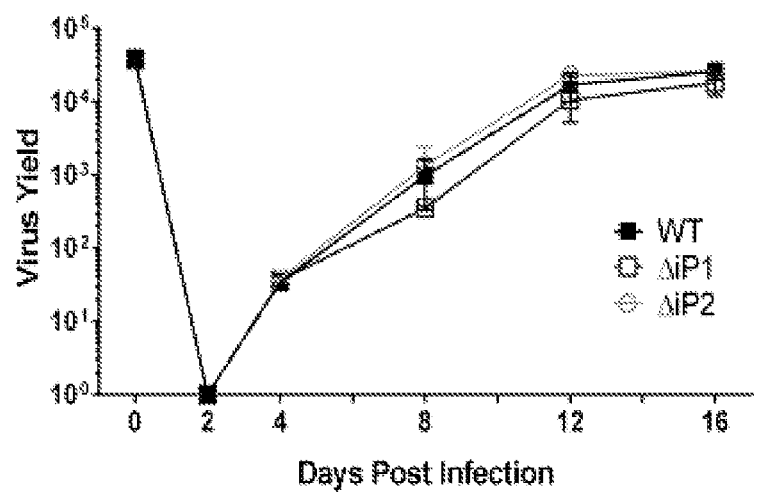
FIG. 6B is a line graph showing multi-step growth analysis (MOI of 0.1) of mutant virus replication. Virus titers were determined by TCID50.
Figure 7A:
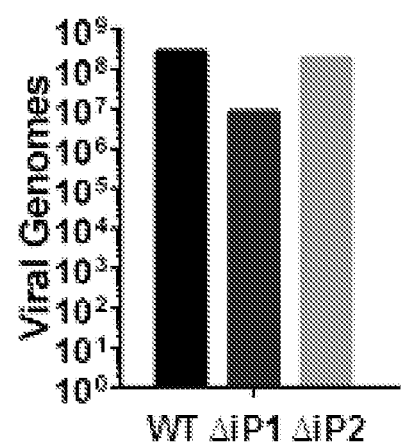
FIG. 7A is a bar graph showing genome levels quantitated by PCR (qPCR) using a BAC standard curve in undifferentiated THP-1 cells were infected with TB40E WT, ΔiP1 or ΔiP2 (at 5 dpi).
Figures 7B, 7C, 7D:
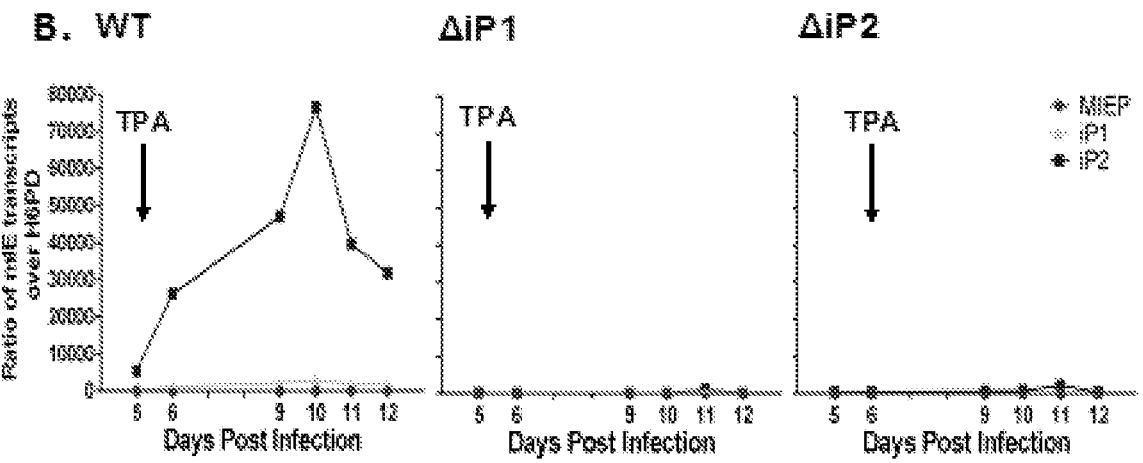
FIGS. 7B-7D are line graphs the ratio of transcripts originating from iP1, iP2, and MIEP promoters in WT (7B), ΔiP1 (7C) or ΔiP2 (7D). At 5 dpi, THP-1 cells were differentiated with TPA and MIE transcripts originating from the MIEP, iP1, and iP2 were quantified relative to H6PD by RT-qPCR over a time course. Note that the deletion of iP2 removes the primer binding site for detection of iP1.

To begin to determine the role for iP1 and iP2 in reactivation, recombinant viruses were generated with large deletions of iP1 (ΔiP1) or iP2 (ΔiP2) in the low passage HCMV strain TB40/E bacterial artificial chromosome (BAC) (FIG. 6A). Both iP1 and iP2 are dispensable for replication in fibroblasts (FIG. 6B) (Arend, et al., *Journal of Virology*, 90, 8855-8865 (2016)). The ability of THP-1 cells infected with each virus to maintain virus genomes during latency and to reinitiate IE1 and IE2 expression after treatment with TPA was measured. Although undifferentiated cells infected with ΔiP1 or ΔiP2 maintained genomes similarly to WT (FIG. 7A), TPA failed to induce IE1 and IE2 expression in ΔiP1 or ΔiP2 infection (FIG. 7B-7D). Thus, iP1 and iP2 are dispensable for the establishment and maintenance of latency (based on genomes maintained with diminished MIE transcription), but important for HCMV reactivation. These results indicate that the iP1 or iP2 promoters are important for MIE gene expression during HCMV reactivation.

Example 2: Host Factors Contribute to Differentiation-Dependent Reactivation of IE1/2 in Latency Materials and Methods FOXO1 and FOXO3 expression was analyzed in mock-infected or TB40/E WT-infected THP-1 cells over a time course prior to and following TPA treatment to induce differentiation and reactivation. cDNA derived from RNA isolated from THP-1 cells at the indicated time points was analyzed by RT-qPCR using primers specific to FOXO1 or FOXO3. THP-1 cells infected and then differentiated with TPA were stained for FOXO3A and the HCMV UL44 protein (marks viral replication compartments in the nucleus) by indirect immunofluorescence.

FOXO3a was expressed in transfected HeLa cells harboring iP2 reporter. The expression of IE1 and IE2 protein levels was measured in the absence of the MIEP (pSVHΔMIEP) in the context of the MIE genomic locus in transfected HeLa cells. IE1 transcript levels, and transcripts derived from the MIEP, iP1, or iP2 were measured (RT-qPCR) when FOXO1 or FOXO3a was expressed in cells transfected with pSVHΔMIEP.

To determine if the putative FOXO sites within iP2 are responsive to FOXO TFs, all three potential FOXO sites were mutated in iP2 in combination by changing two adenines in each FOXO-binding motif (RAAATAA) to cytosines (RACCTAA). iP2 luciferase reporter was used to measure activation by FOXO3a in HeLa cells transfected with the ΔFOXObp sites mutant. IE1 and IE2 proteins were also measured in the absence of the MIEP (ΔMIEPΔFOXObp) in transfected HeLa cells.

Results

HCMV reactivation is linked to host cell differentiation (Taylor-Wiedeman, et al., *Journal of Virology*, 68, 1597-604 (1994), Reeves, et al., *Current topics in microbiology and immunology*, 325, 297-313 (2008), Soderberg-Naucler, et al., *Journal of Virology*, 75, 7543-54. (2001), Smith, et al., *Journal of Virology*, 78, 4444-4453 (2004), Lazzarotto, et al., *Arch. Virol.*, 135, 13-28 (1994)), and viral promoters are often transactivated by host factors (Caposio, et al., *Journal of Virology*, 84, 4481-4493 (2010), Khan, et al., *Journal of Immunology*, 182, 7784-7794 (2009)). Understanding the regulation of iP1 and iP2 by host transcription factors (TFs) is advantageous to understanding how cellular cues trigger HCMV reactivation from latency.

Figure 8A:
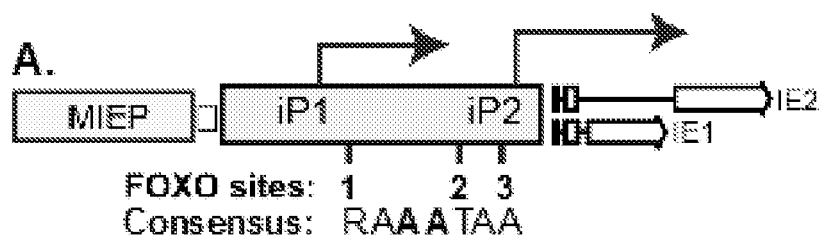
FIG. 8A is a schematic of FOXO binding sites in the intronic MIE promoters.
Figures 8B, 8C:
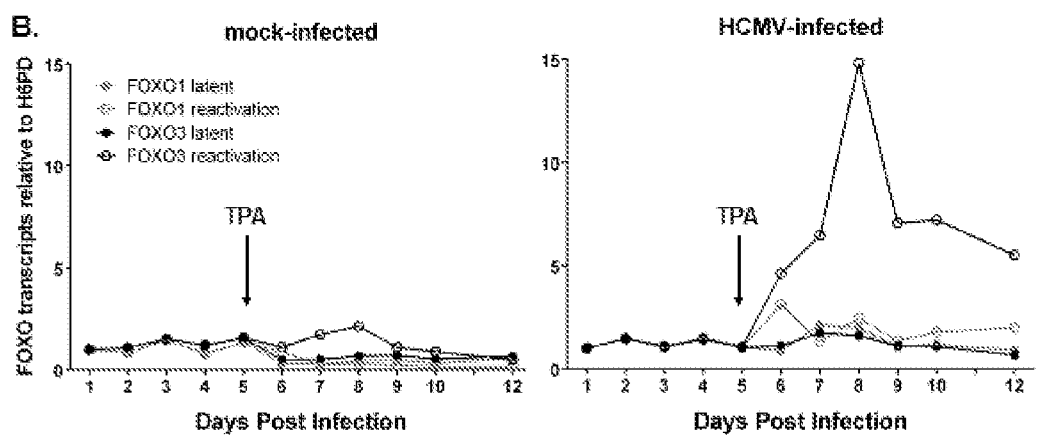
FIGS. 8B and 8C are line graphs showing FOXO1 and FOXO3 expression in mock-infected (8B) or TB40/E WT-infected (8C) THP-1 cells over a time course prior to and following TPA treatment to induce differentiation and reactivation. cDNA derived from RNA isolated from THP-1 cells at the indicated time points was analyzed by RT-qPCR using primers specific to FOXO1 or FOXO3.

To identify factors that might regulate iP1 and iP2, the iP1 and iP2 promoters were searched for host transcription factor binding sites. Three consensus sites for the forkhead family (FOXO) of TFs were identified (FIG. 8A). Intriguingly, FOXO TFs regulate monocyte-to-macrophage differentiation (Chung, et al., *J. Leukoc. Biol.*, 97, 327-339 (2015), Zheng, et al., *The FEBS journal*, 284, 1309-1323 (2017), Zhu, et al., *Atherosclerosis*, 219, 492-498 (2011), Osswald, et al., *Blood*, blood-2017-07-795278 (2018). doi:10.1182/blood-2017-07-795278, Tothova, et al., *Cell Stem Cell*, 1, 140-152 (2007)), which induces HCMV reactivation (Soderberg-Naucler, et al., *Cell*, 91, 119-26 (1997), Ibanez, et al., *Journal of Virology*, 65, 6581-6588 (1991), Weinshenker, et al., *J Immunol*, 140, 1625-31. (1988)). Also, chemical inducers of reactivation, such as phorbol esters (e.g. TPA) and PI3 kinase (PI3K) inhibitors (e.g. LY294002), increase FOXO expression (Zheng, et al., *The FEBS journal*, 284, 1309-1323 (2017)) and the induction of FOXO-responsive genes (Gilley, et al., *The Journal of cell biology*, 162, 613-622 (2003), Kops, et al., *Nature*, 419, 316-321 (2002), Stahl, et al., *J. Immunol.*, 168, 5024-5031 (2002)). In the context of infection, FOXO3a expression and nuclear translocation is strongly induced by differentiation of infected THP-1 cells (FIG. 8B-C). These data indicate that FOXO-dependent activation of iP1 and iP2 links HCMV reactivation to changes in the biology of latently infected cells.

Figure 9A:
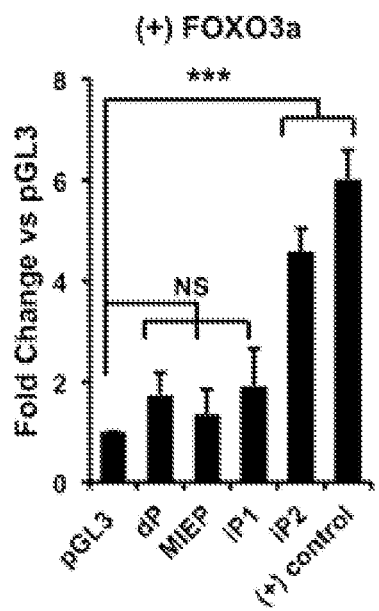
FIG. 9A is a bar graph showing the effect of pGL3, dp, MIEP, iP1, and iP2 promoter reporters in transfected HeLa cells.
Figures 9B, 9C:
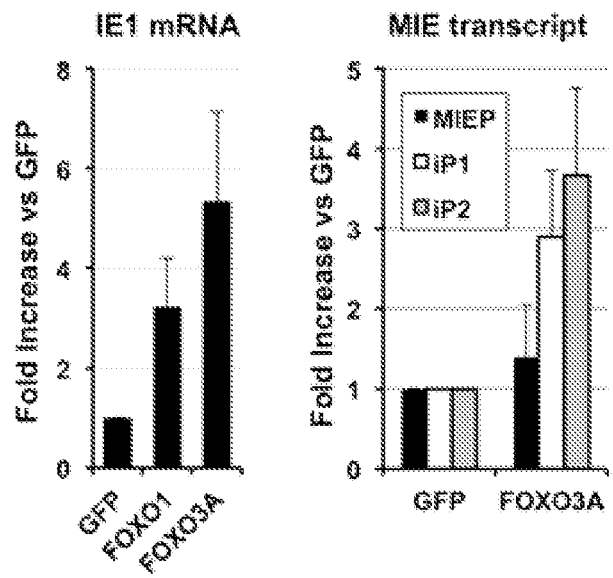
FIG. 9B is a bar graph showing the fold increase in IE1 transcript levels (RT-qPCR) when FOXO1 or FOXO3a is expressed in cells transfected with pSVHΔMIEP.
FIG. 9C is a bar graph showing the fold increase in transcripts derived from the MIEP, iP1, or iP2 when FOXO3a is expressed in cells transfected with pSVHΔMIEP.

To determine if FOXOs transactivate the intronic MIE promoters, the effect of FOXO3a expression on iP1 and iP2 promoter activity was examined in HeLa cells transfected with reporter constructs for the dP, MIEP, iP1, and iP2 promoters (Arend, et al., *Journal of Virology*, 90, 8855-8865 (2016)). Results indicate that FOXO3a expression increased the activity of iP2 but had no significant effect on dP, the MIEP, or iP1 (FIG. 9A). Next, whether FOXO TFs stimulate IE1 and IE2 expression was tested in the context of the MIE genomic locus. The plasmid pSVH contains the entire MIE genomic locus (FIG. 8A), and has been used extensively to study regulatory elements controlling IE1 and IE2 expression (Martinez, et al., *Journal of Virology*, 88, 7389-7401 (2014), Gustems, et al., *Journal of Virology*, 80, 9899-9904 (2006), Stenberg, et al., *Journal of Virology*, 64, 1556-1565 (1990)). Deletion of the core MIEP promoter from pSVH (pSVHΔMIEP) lowered expression of IE1 (Arend, et al., *Journal of Virology*, 90, 8855-8865 (2016)). However, overexpression of FOXO3a significantly induced IE1 mRNA and protein expression from pSVHΔMIEP, with a concomitant increase in iP1 and iP2-specific transcripts (FIG. 9B-9C). Thus, FOXO TFs stimulate the iP1 and iP2 promoters to drive MIE expression in the absence of MIEP activity, as observed in HCMV reactivation.

Figure 10:
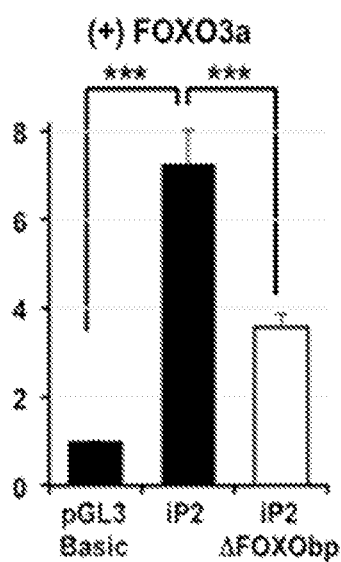
FIG. 10 is a bar graph showing the effect of the combined mutation of three potential FOXO binding (ΔFOXObp) sites in a iP2 luciferase reporter on activation by FOXO3a in transfected HeLa cells.

To determine if the putative FOXO sites within iP2 are responsive to FOXO TFs, all three potential FOXO sites in iP2 were mutated in combination by changing two adenines in each FOXO-binding motif (RAAATAA) to cytosines (RACCTAA) (FIG. 8A). The combined mutagenesis of all three sites significantly reduced activation of the iP2 reporter by FOXO3a (FIG. 10) and eliminated FOXO3a-mediated induction of IE1 and IE2 protein levels in cells transfected with the pSVHΔMIEP genomic clone. These results indicate that the binding of FOXO TFs stimulates iP1 and iP2 activity and rescues MIE gene expression in the absence of the MIEP.

Example 3: The Intronic Promoters are Highly Conversed

Materials and Methods

Source for Blast Search/Alignment for Intronic Promoter #1

The query sequence was 500 base pairs including nucleotides 206940:207439 of Genbank file (Accession #) EF999921.1 Human herpesvirus 5 strain TB40/E clone TB40-BAC4, complete sequence. The 500 base pairs are referred to as −450 to +50 of the transcription start site, as defined in Arend, et al., *Journal of Virology*, 90, 8855-8865 (2016).

The sequence is (SEQ ID NO: 13)
ATTCGCGTGGAGATCCCACGCTATGTTTAATAAAAACTGCGGGTACTGGG

GACGGTGTTGTTGTATATGTGAATTTGTAAATAATAAATGGGACCCCATC

CTGTAAAAATACAGAGTCCGTGTCAGTCTCTGAAGGACAGAGTATTGGCA

TATAGCCAATAAAGAGAGTTGTGGCAAAGAGCCATGTTATGGATTAGTAA

TGGAAAGTATCGTCACCAATAGGGGAGTGGTCAATAATGGTCAATAACCC

ACACCTATAGGCTAAGCTATACCATCACCTATAGCATAAGGAAGCGGGGG

TGTATAGACCCCAAGCCAAAAACAGTATAGCATGCATAAGAAGCCAAGGG

GGTGGGCCTATAGAGTCTATAGGCGGTACTTACGTCACTCTTGGCACGGG

GAATCCGCGTTCCAATGCACCGTTCCCGGCCGCGGAGGCTGGATCGGTCC

CGGTGTCTTCTATGGAGGTCAAAACAGCGTGGATGGCGTCTCCAGGCGAT

The above sequence is the reverse complement of the actual sequence.

The actual query sequence used in the BLAST search is thus:

(SEQ ID NO: 5)
ATCGCCTGGAGACGCCATCCACGCTGTTTTGACCTCCATAGAAGACACCG

GGACCGATCCAGCCTCCGCGGCCGGGAACGGTGCATTGGAACGCGGATTC

CCCGTGCCAAGAGTGACGTAAGTACCGCCTATAGACTCTATAGGCCCACC

CCCTTGGCTTCTTATGCATGCTATACTGTTTTGGCTTGGGGTCTATACA

CCCCCGCTTCCTTATGCTATAGGTGATGGTATAGCTTAGCCTATAGGTGT

GGGTTATTGACCATTATTGACCACTCCCCTATTGGTGACGATACTTTCCA

-continued
TTACTAATCCATAACATGGCTCTTTGCCACAACTCTCTTTATTGGCTATA

TGCCAATACTCTGTCCTTCAGAGACTGACACGGACTCTGTATTTTTACAG

GATGGGGTCCCATTTATTATTTACAAATTCACATATACAACAACACCGTC

CCCAGTACCCGCAGTTTTTATTAAACATAGCGTGGGATCTCCACGCGAAT

BLAST BLASTN 2.8.0+
BLAST Analysis for Sequence: Untitled
Search from 1 to 500 Program: blastn
Expect: 10 Low complexity filter: on Matrix: n/a
Genetic Code: n/a Gapped search: on
Open cost: 5 Extend cost: 2
Database: nr (1,001,480,804 residues in 48,102,473 sequences)
Karlin-Altschul Statistics:
Kappa=0.41, Lambda=0.625, Entropy=0.78

Source for Blast Search/Alignment for Intronic Promoter #2

The query sequence was 500 base pairs having nucleotides 206499:206998 of Genbank file (Accession #) EF999921.1 Human herpesvirus 5 strain TB40/E clone TB40-BAC4, complete sequence. The 500 base pairs are −450 to +50 of the transcription start site, as defined in Arend, et al., *Journal of Virology*, 90, 8855-8865 (2016).

The sequence is (SEQ ID NO: 14)
CAGAAAAGACCCATGGAAAGGAACAGTCTGTTAGTCTGTCAGCTATTATG

TCTGGTGGCGCGCGCGGCAGCAACGAGTACTGCTCAGACTACACTGCCCT

CCACCGTTAACAGCACCGCAACGGGAGTTACCTCTGACTCTTATCAGAAC

ACAACAACTCAGCTGCCTGCATCTTCTTCTGCCGCTGCCTTAAGTCTTCC

AAATGCGTCAGCGGTGCAAGCCCGCTCCCCGAGCTCATTTTCAGACACAT

ACCCTACCGCCACGGCCTTGTGCGGCACACTGGTGGTGGTGGGCATCGTG

CTGTGCCTAAGTCTGGCCTCCACTGTTAGGAGCAAGGAGCTGCCAAGCGA

CCATGAGCCGCTGGAGGCATGGGAGCAGGGCTCGGATGTAGAAGCTCCGC

CGCTACCGGAGAAGAGCCCATGTCCGGAACACGTACCCGAGATTCGCGTG

GAGATCCCACGCTATGTTTAATAAAAACTGCGGGTACTGGGGACGGTGTT

The above sequence is the reverse complement of the actual sequence.

The actual query sequence used in the BLAST search is thus:

(SEQ ID NO: 6)
AACACCGTCCCCAGTACCCGCAGTTTTTATTAAACATAGCGTGGGATCTC

CACGCGAATCTCGGGTACGTGTTCCGGACATGGGCTCTTCTCCGGTAGCG

GCGGAGCTTCTACATCCGAGCCCTGCTCCCATGCCTCCAGCGGCTCATGG

TCGCTTGGCAGCTCCTTGCTCCTAACAGTGGAGGCCAGACTTAGGCACAG

CACGATGCCCACCACCACCAGTGTGCCGCACAAGGCCGTGGCGGTAGGGT

ATGTGTCTGAAAATGAGCTCGGGGAGCGGGCTTGCACCGCTGACGCATTT

GGAAGACTTAAGGCAGCGGCAGAAGAAGATGCAGGCAGCTGAGTTGTTGT

GTTCTGATAAGAGTCAGAGGTAACTCCCGTTGCGGTGCTGTTAACGGTGG

-continued
AGGGCAGTGTAGTCTGAGCAGTACTCGTTGCTGCCGCGCGCGCCACCAGA

CATAATAGCTGACAGACTAACAGACTGTTCCTTTCCATGGGTCTTTTCTG

BLAST BLASTN 2.8.0+
BLAST Analysis for Sequence: Untitled
Search from 1 to 500 Program: blastn
Expect: 10 Low complexity filter: on Matrix: n/a
Genetic Code: n/a Gapped search: on
Open cost: 5 Extend cost: 2

Database: nr (1,001,480,804 residues in 48,102,473 sequences)
Karlin-Altschul Statistics:
Kappa=0.41, Lambda=0.625, Entropy=0.78

Results 500 base pairs (−450 to +50 of the transcription start site of iP1 and iP2) were separately used as queries sequences in BLAST searches. The results show that iP1 and iP2 are highly conserved across HCMV strains. The first 100 "hits" are provided in Table 1 (iP1) and Table 2 (iP2) below.

TABLE 1

BLAST Search Results for iP1

| Sequences producing high-scoring segment pairs: | High Score | E Value N |
|---|---|---|
| 1. >gb\|MF871618.1\| Synthetic human betaherpesvirus 5 clone TB40-BAC- . . . | 1000 | 0.0e+001 |
| 2. >gb\|KT726944.2\| Human betaherpesvirus 5 strain NL/Rot5/Urine/2012 . . . | 1000 | 0.0e+001 |
| 3. >gb\|KX544839.1\| Human herpesvirus 5 isolate TB40-E_UNC, complete . . . | 1000 | 0.0e+001 |
| 4. >gb\|KR534210.1\| Human herpesvirus 5 strain JER5268, complete geno . . . | 1000 | 0.0e+001 |
| 5. >gb\|KJ361963.1\| Human herpesvirus 5 strain PAV7, complete genome | 1000 | 0.0e+001 |
| 6. >gb\|KP745720.1\| Human herpesvirus 5 strain BE/15/2011, complete g . . . | 1000 | 0.0e+001 |
| 7. >gb\|JX512204.1\| Human herpesvirus 5 strain HAN16, complete genome | 1000 | 0.0e+001 |
| 8. >gb\|KF297339.1\| Human herpesvirus 5 strain TB40/E clone Lisa, com . . . | 1000 | 0.0e+001 |
| 9. >gb\|EF999921.1\| Human herpesvirus 5 strain TB40/E clone TB40-BAC4 . . . | 1000 | 0.0e+001 |
| 10. >gb\|AY446866.1\| Human herpesvirus 5 strain TB40/E, partial genome | 1000 | 0.0e+001 |
| 11. >gb\|MF084224.1\| Human betaherpesvirus 5 strain HER1, complete gen . . . | 994 | 0.0e+001 |
| 12. >gb\|KR534206.1\| Human herpesvirus 5 strain JER4041, complete geno . . . | 994 | 0.0e+001 |
| 13. >gb\|KJ361965.1\| Human herpesvirus 5 strain PAV11, complete genome | 994 | 0.0e+001 |
| 14. >gb\|KJ361947.1\| Human herpesvirus 5 strain 2CEN5, complete genome | 994 | 0.0e+001 |
| 15. >gb\|KP745706.1\| Human herpesvirus 5 strain BE/41/2011, complete g . . . | 994 | 0.0e+001 |
| 16. >gb\|KP745681.1\| Human herpesvirus 5 strain BE/43/2011, complete g . . . | 994 | 0.0e+001 |
| 17. >gb\|KP745678.1\| Human herpesvirus 5 strain BE/25/2010, complete g . . . | 994 | 0.0e+001 |
| 18. >gb\|KP745646.1\| Human herpesvirus 5 strain BE/8/2012, complete ge . . . | 994 | 0.0e+001 |
| 19. >gb\|KC519319.1\| Human herpesvirus 5 strain BE/9/2010, complete ge . . . | 994 | 0.0e+001 |
| 20. >gb\|JX512203.1\| Human herpesvirus 5 strain HAN12, complete genome | 994 | 0.0e+001 |
| 21. >gb\|JX512201.1\| Human herpesvirus 5 strain HAN3, complete genome | 994 | 0.0e+001 |
| 22. >gb\|GU179288.1\| Human herpesvirus 5 strain U8, complete genome | 994 | 0.0e+001 |
| 23. >gb\|MF084223.1\| Human betaherpesvirus 5 strain LON1, complete gen . . . | 990 | 0.0e+001 |
| 24. >gb\|MH036940.1\| Synthetic human betaherpesvirus 5 strain Merlin i . . . | 990 | 0.0e+001 |
| 25. >gb\|MH036939.1\| Synthetic human betaherpesvirus 5 strain Merlin i . . . | 990 | 0.0e+001 |
| 26. >gb\|Y490086.1\| Human betaherpesvirus 5 strain HANSCTR11B, comple . . . | 990 | 0.0e+001 |
| 27. >gb\|KY490082.1\| Human betaherpesvirus 5 strain HANSCTR8, complete . . . | 990 | 0.0e+001 |
| 28. >gb\|KY490081.1\| Human betaherpesvirus 5 strain HANSCTR2, complete . . . | 990 | 0.0e+001 |
| 29. >gb\|KY490061.1\| Human betaherpesvirus 5 strain PAV31, complete ge . . . | 990 | 0.0e+001 |
| 30. >gb\|KY123652.1\| Human herpesvirus 5 strain HANRTR5, complete geno . . . | 990 | 0.0e+001 |
| 31. >gb\|KP973642.1\| Human herpesvirus 5 strain Merlin isolate RCMV203 . . . | 990 | 0.0e+001 |
| 32. >gb\|KP973641.1\| Human herpesvirus 5 strain Merlin isolate RCMV185 . . . | 990 | 0.0e+001 |
| 33. >gb\|KP973640.1\| Human herpesvirus 5 strain Merlin isolate RCMV185 . . . | 990 | 0.0e+001 |
| 34. >gb\|KP973639.1\| Human herpesvirus 5 strain Merlin isolate RCMV185 . . . | 990 | 0.0e+001 |
| 35. >gb\|KP973638.1\| Human herpesvirus 5 strain Merlin isolate RCMV185 . . . | 990 | 0.0e+001 |
| 36. >gb\|KP973637.1\| Human herpesvirus 5 strain Merlin isolate RCMV184 . . . | 990 | 0.0e+001 |
| 37. >gb\|KP973636.1\| Human herpesvirus 5 strain Merlin isolate RCMV184 . . . | 990 | 0.0e+001 |
| 38. >gb\|KP973635.1\| Human herpesvirus 5 strain Merlin isolate RCMV184 . . . | 990 | 0.0e+001 |
| 39. >gb\|KP973634.1\| Human herpesvirus 5 strain Merlin isolate RCMV184 . . . | 990 | 0.0e+001 |
| 40. >gb\|KP973633.1\| Human herpesvirus 5 strain Merlin isolate RCMV184 . . . | 990 | 0.0e+001 |
| 41. >gb\|KP973632.1\| Human herpesvirus 5 strain Merlin isolate RCMV183 . . . | 990 | 0.0e+001 |
| 42. >gb\|KP973631.1\| Human herpesvirus 5 strain Merlin isolate RCMV183 . . . | 990 | 0.0e+001 |
| 43. >gb\|KP973630.1\| Human herpesvirus 5 strain Merlin isolate RCMV182 . . . | 990 | 0.0e+001 |
| 44. >gb\|KP973629.1\| Human herpesvirus 5 strain Merlin isolate RCMV182 . . . | 990 | 0.0e+001 |
| 45. >gb\|KP973628.1\| Human herpesvirus 5 strain Merlin isolate RCMV182 . . . | 990 | 0.0e+001 |
| 46. >gb\|KP973627.1\| Human herpesvirus 5 strain Merlin isolate RCMV181 . . . | 990 | 0.0e+001 |
| 47. >gb\|KP973626.1\| Human herpesvirus 5 strain Merlin isolate RCMV181 . . . | 990 | 0.0e+001 |
| 48. >gb\|KP973625.1\| Human herpesvirus 5 strain Merlin isolate RCMV181 . . . | 990 | 0.0e+001 |
| 49. >gb\|KP973624.1\| Human herpesvirus 5 strain Merlin isolate RCMV120 . . . | 990 | 0.0e+001 |
| 50. >gb\|KP973623.1\| Human herpesvirus 5 strain Merlin isolate RCMV120 . . . | 990 | 0.0e+001 |
| 51. >gb\|KR534212.1\| Human herpesvirus 5 strain JER5550, complete geno . . . | 990 | 0.0e+001 |
| 52. >gb\|KR534211.1\| Human herpesvirus 5 strain JER5409, complete geno . . . | 990 | 0.0e+001 |
| 53. >gb\|KR534197.1\| Human herpesvirus 5 strain JER851, complete genome | 990 | 0.0e+001 |
| 54. >gb\|KU221100.1\| Human herpesvirus 5 strain Merlin isolate RCMV187 . . . | 990 | 0.0e+001 |
| 55. >gb\|KU221099.1\| Human herpesvirus 5 strain Merlin isolate RCMV183 . . . | 990 | 0.0e+001 |
| 56. >gb\|KU221098.1\| Human herpesvirus 5 strain Merlin isolate RCMV181 . . . | 990 | 0.0e+001 |
| 57. >gb\|KU221097.1\| Human herpesvirus 5 strain Merlin isolate RCMV181 . . . | 990 | 0.0e+001 |
| 58. >gb\|KU221096.1\| Human herpesvirus 5 strain Merlin isolate RCMV180 . . . | 990 | 0.0e+001 |
| 59. >gb\|KU221095.1\| Human herpesvirus 5 strain Merlin isolate RCMV180 . . . | 990 | 0.0e+001 |
| 60. >gb\|KU221094.1\| Human herpesvirus 5 strain Merlin isolate RCMV180 . . . | 990 | 0.0e+001 |
| 61. >gb\|KU221093.1\| Human herpesvirus 5 strain Merlin isolate RCMV179 . . . | 990 | 0.0e+001 |

TABLE 1-continued

BLAST Search Results for iP1

| Sequences producing high-scoring segment pairs: | High Score | E Value N |
|---|---|---|
| 62. >gb\|KU221092.1\| Human herpesvirus 5 strain Merlin isolate RCMV179 . . . | 990 | 0.0e+001 |
| 63. >gb\|KU221091.1\| Human herpesvirus 5 strain Merlin isolate RCMV165 . . . | 990 | 0.0e+001 |
| 64. >gb\|KU221090.1 \|Human herpesvirus 5 strain Merlin isolate RCMV159 . . . | 990 | 0.0e+001 |
| 65. >gb\|KJ361970.1\| Human herpesvirus 5 strain PAV26, complete genome | 990 | 0.0e+001 |
| 66. >gb\|KJ361958.1\| Human herpesvirus 5 strain HAN40, complete genome | 990 | 0.0e+001 |
| 67. >gb\|KJ361954.1\| Human herpesvirus 5 strain HAN32, complete genome | 990 | 0.0e+001 |
| 68. >gb\|KJ361953.1\| Human herpesvirus 5 strain HAN30, complete genome | 990 | 0.0e+001 |
| 69. >gb\|KJ361951.1\| Human herpesvirus 5 strain HAN21, complete genome | 990 | 0.0e+001 |
| 70. >gb\|KP745708.1\| Human herpesvirus 5 strain BE/8/2010, complete ge . . . | 990 | 0.0e+001 |
| 71. >gb\|KP745704.1\| Human herpesvirus 5 strain BE/32/2011, complete g . . . | 990 | 0.0e+001 |
| 72. >gb\|KP745694.1\| Human herpesvirus 5 strain BE/12/2010, complete g . . . | 990 | 0.0e+001 |
| 73. >gb\|KP745688.1\| Human herpesvirus 5 strain BE/12/2012, complete g . . . | 990 | 0.0e+001 |
| 74. >gb\|KP745686.1\| Human herpesvirus 5 strain BE/39/2011, complete g . . . | 990 | 0.0e+001 |
| 75. >gb\|KP745651.1\| Human herpesvirus 5 strain BE/9/2012, complete ge . . . | 990 | 0.0e+001 |
| 76. >gb\|KP745650.1\| Human herpesvirus 5 strain BE/1/2011, complete ge . . . | 990 | 0.0e+001 |
| 77. >gb\|KP745647.1\| Human herpesvirus 5 strain BE/18/2010, complete g . . . | 990 | 0.0e+001 |
| 78. >gb\|KP745637.1\| Human herpesvirus 5 strain BE/9/2011, complete ge . . . | 990 | 0.0e+001 |
| 79. >gb\|KM192302.1\| Human herpesvirus 5 strain Merlin isolate RCMV167 . . . | 990 | 0.0e+001 |
| 80. >gb\|KM192301.1\| Human herpesvirus 5 strain Merlin isolate RCMV167 . . . | 990 | 0.0e+001 |
| 81. >gb\|KM192300.1\| Human herpesvirus 5 strain Merlin isolate RCMV152 . . . | 990 | 0.0e+001 |
| 82. >gb\|KM192299.1\| Human herpesvirus 5 strain Merlin isolate RCMV114 . . . | 990 | 0.0e+001 |
| 83. >gb\|KM192298.1\| Human herpesvirus 5 strain Merlin isolate RCMV111 . . . | 990 | 0.0e+001 |
| 84. >gb\|KC519323.1\| Human herpesvirus 5 strain BE/27/2010, complete g . . . | 990 | 0.0e+001 |
| 85. >gb\|KC519320.1\| Human herpesvirus 5 strain BE/10/2010, complete g . . . | 990 | 0.0e+001 |
| 86. >gb\|JX512206.1\| Human herpesvirus 5 strain HAN22, complete genome | 990 | 0.0e+001 |
| 87. >gb\|GQ222010.2\| Human herpesvirus 5 strain 66, partial genome | 990 | 0.0e+001 |
| 88. >gb\|GU179290.1\| Human herpesvirus 5 strain U11, complete genome | 990 | 0.0e+001 |
| 89. >gb\|GU179001.1\| Human herpesvirus 5 transgenic strain Merlin, com . . . | 990 | 0.0e+001 |
| 90. >gb\|AY446894.2\| Human herpesvirus 5 strain Merlin, complete genome | 990 | 0.0e+001 |
| 91. >gb\|GQ222018.1\| Human herpesvirus 5 strain VR3216B, partial genome | 988 | 0.0e+001 |
| 92. >gb\|GQ396663.1\| Human herpesvirus 5 strain HAN20, complete genome | 988 | 0.0e+001 |
| 93. >gb\|KY123650.1\| Human herpesvirus 5 strain HANRTR2, complete geno . . . | 984 | 0.0e+001 |
| 94. >gb\|KJ361964.1\| Human herpesvirus 5 strain PAV8, complete genome | 984 | 0.0e+001 |
| 95. >gb\|KP745698.1\| Human herpesvirus 5 strain BE/20/2011, complete g . . . | 984 | 0.0e+001 |
| 96. >gb\|KY490087.1\| Human betaherpesvirus 5 strain HANSCTR12, complet . . . | 980 | 0.0e+001 |
| 97. >gb\|KY490078.1\| Human betaherpesvirus 5 strain HANRTR10, complete . . . | 980 | 0.0e+001 |
| 98. >gb\|KY490077.1\| Human betaherpesvirus 5 strain HANRTR9, complete . . . | 980 | 0.0e+001 |
| 99. >gb\|KY490075.1\| Human betaherpesvirus 5 strain HANRTR6, complete . . . | 980 | 0.0e+001 |
| 100. >gb\|KY490067.1\| Human betaherpesvirus 5 strain PRA5, complete gen . . . | 980 | 0.0e+001 |

The BLAST search showed that over 100 strains of HCMV had a least 99% sequence identity over the iP1 query sequence. The alignment data between the query sequence and "hit" #100, >gb\|KY490067.1\| Human betaherpesvirus 5 strain PRA5, complete genome, Length=234989 was: Score=884.9 bits (980), Expect=0.0e+00 Identities=496/500 (99%), Positives=496/500 (99%), Gaps=0/500 (0%).

TABLE 2

BLAST Search Results for iP2

| Sequences producing high-scoring segment pairs: | High Score | E Value N |
|---|---|---|
| 1. >gb\|MF084224.1\| Human betaherpesvirus 5 strain HER1, complete gen . . . | 1000 | 0.0e+001 |
| 2. >gb\|KY490083.1\| Human betaherpesvirus 5 strain HANSCTR9, complete . . . | 1000 | 0.0e+001 |
| 3. >gb\|KY490080.1\| Human betaherpesvirus 5 strain HANSCFR1B, complet . . . | 1000 | 0.0e+001 |
| 4. >gb\|MF871618.1\| Synthetic human betaherpesvirus 5 clone TB40-BAC- . . . | 1000 | 0.0e+001 |
| 5. >gb\|KY123652.1\| Human betaherpesvirus 5 strain HANRTR5, complete geno . . . | 1000 | 0.0e+001 |
| 6. >gb\|KX544839.1\| Human herpesvirus 5 isolate TB40-E_UNC, complete . . . | 1000 | 0.0e+001 |
| 7. >gb\|KR534211.1\| Human herpesvirus 5 strain JER5409, complete geno . . . | 1000 | 0.0e+001 |
| 8. >gb\|KR534206.1\| Human herpesvirus 5 strain JER4041, complete geno . . . | 1000 | 0.0e+001 |
| 9. >gb\|KR534197.1\| Human herpesvirus 5 strain JER851, complete genome | 1000 | 0.0e+001 |
| 10. >gb\|KJ361965.1\| Human herpesvirus 5 strain PAV11, complete genome | 1000 | 0.0e+001 |
| 11. >gb\|KJ361964.1\| Human herpesvirus 5 strain PAV8, complete genome | 1000 | 0.0e+001 |
| 12. >gb\|KJ361963.1\| Human herpesvirus 5 strain PAV7, complete genome | 1000 | 0.0e+001 |
| 13. >gb\|KJ361957.1\| Human herpesvirus 5 strain HAN39, complete genome | 1000 | 0.0e+001 |
| 14. >gb\|KJ361955.1\| Human herpesvirus 5 strain HAN33, complete genome | 1000 | 0.0e+001 |
| 15. >gb\|KP745720.1\| Human herpesvirus 5 strain BE/15/2011, complete g . . . | 1000 | 0.0e+001 |
| 16. >gb\|KP745699.1\| Human herpesvirus 5 strain BE/1/2012, complete ge . . . | 1000 | 0.0e+001 |

TABLE 2-continued

BLAST Search Results for iP2

| Sequences producing high-scoring segment pairs: | High Score | E Value N |
|---|---|---|
| 17. >gb\|KP745689.1\| Human herpesvirus 5 strain BE/17/2011, complete g . . . | 1000 | 0.0e+001 |
| 18. >gb\|KP745678.1\| Human herpesvirus 5 strain BE/25/2010, complete g . . . | 1000 | 0.0e+001 |
| 19. >gb\|KP745676.1\| Human herpesvirus 5 strain BE/28/2010, complete g . . . | 1000 | 0.0e+001 |
| 20. >gb\|KP745673.1\| Human herpesvirus 5 strain BE/42/2011, complete g . . . | 1000 | 0.0e+001 |
| 21. >gb\|KP745651.1\| Human herpesvirus 5 strain BE/9/2012, complete ge . . . | 1000 | 0.0e+001 |
| 22. >gb\|KP745650.1\| Human herpesvirus 5 strain BE/1/2011, complete ge . . . | 1000 | 0.0e+001 |
| 23. >gb\|KP745646.1\| Human herpesvirus 5 strain BE/8/2012, complete ge . . . | 1000 | 0.0e+001 |
| 24. >gb\|JX512204.1\| Human herpesvirus 5 strain HAN16, complete genome | 1000 | 0.0e+001 |
| 25. >gb\|JX512203.1\| Human herpesvirus 5 strain HAN12, complete genome | 1000 | 0.0e+001 |
| 26. >gb\|KF297339.1\| Human herpesvirus 5 strain TB40/E clone Lisa, com . . . | 1000 | 0.0e+001 |
| 27. >gb\|GQ222018.1\| Human herpesvirus 5 strain VR3216B, partial genome | 1000 | 0.0e+001 |
| 28. >gb\|GQ396663.1\| Human herpesvirus 5 strain HAN20, complete genome | 1000 | 0.0e+001 |
| 29. >gb\|EF999921.1\| Human herpesvirus 5 strain TB40/E clone TB40-BAC4 . . . | 1000 | 0.0e+001 |
| 30. >gb\|AY446866.1\| Human herpesvirus 5 strain TB40/E, partial genome | 1000 | 0.0e+001 |
| 31. >gb\|KY490064.1\| Human betaherpesvirus 5 strain PRA2, complete gen . . . | 994 | 0.0e+001 |
| 32. >gb\|KT726949.2\| Human betaherpesvirus 5 strain UK/Lon6/Urine/2011 . . . | 994 | 0.0e+001 |
| 33. >gb\|KJ361951.1\| Human herpesvirus 5 strain HAN21, complete genome | 994 | 0.0e+001 |
| 34. >gb\|KJ361948.1\| Human herpesvirus 5 strain 2CEN15, complete genome | 994 | 0.0e+001 |
| 35. >gb\|KJ361947.1\| Human herpesvirus 5 strain 2CEN5, complete genome | 994 | 0.0e+001 |
| 36. >gb\|KP745708.1\| Human herpesvirus 5 strain BE/8/2010, complete ge . . . | 994 | 0.0e+001 |
| 37. >gb\|KP745706.1\| Human herpesvirus 5 strain BE/41/2011, complete g . . . | 994 | 0.0e+001 |
| 38. >gb\|KP745688.1\| Human herpesvirus 5 strain BE/12/2012, complete g . . . | 994 | 0.0e+001 |
| 39. >gb\|KP745686.1\| Human herpesvirus 5 strain BE/39/2011, complete g . . . | 994 | 0.0e+001 |
| 40. >gb\|KP745681.1\| Human herpesvirus 5 strain BE/43/2011, complete g . . . | 994 | 0.0e+001 |
| 41. >gb\|KP745635.1\| Human herpesvirus 5 strain BE/5/2012, complete ge . . . | 994 | 0.0e+001 |
| 42. >gb\|KC519320.1\| Human herpesvirus 5 strain BE/10/2010, complete g . . . | 994 | 0.0e+001 |
| 43. >gb\|KC519319.1\| Human herpesvirus 5 strain BE/9/2010, complete ge . . . | 994 | 0.0e+001 |
| 44. >gb\|GU179288.1\| Human herpesvirus 5 strain U8, complete genome | 994 | 0.0e+001 |
| 45. >gb\|KY490070.1\| Human betaherpesvirus 5 strain PRA8, complete gen . . . | 990 | 0.0e+001 |
| 46. >gb\|KY490066.1\| Human betaherpesvirus 5 strain PRA4, complete gen . . . | 990 | 0.0e+001 |
| 47. >gb\|KT726954.2\| Human betaherpesvirus 5 strain UK/Lon4/Bile/2011, . . . | 990 | 0.0e+001 |
| 48. >gb\|KY123653.1\| Human herpesvirus 5 strain HANSCTR4, complete gen . . . | 990 | 0.0e+001 |
| 49. >gb\|KY123650.1\| Human herpesvirus 5 strain HANRTR2, complete geno . . . | 990 | 0.0e+001 |
| 50. >gb\|KR534210.1\| Human herpesvirus 5 strain JER5268, complete geno . . . | 990 | 0.0e+001 |
| 51. >gb\|KU550087.1\| Human herpesvirus 5 strain NAN1LA, complete genome | 990 | 0.0e+001 |
| 52. >gb\|KJ361952.1\| Human herpesvirus 5 strain HAN27, complete genome | 990 | 0.0e+001 |
| 53. >gb\|KJ361949.1\| Human herpesvirus 5 strain 2CEN30, complete genome | 990 | 0.0e+001 |
| 54. >gb\|KT959235.1\| Human herpesvirus 5 strain DB, complete genome | 990 | 0.0e+001 |
| 55. >gb\|KP745698.1\| Human herpesvirus 5 strain BE/20/2011, complete g . . . | 990 | 0.0e+001 |
| 56. >gb\|KP745695.1\| Human herpesvirus 5 strain BE/6/2012, complete ge . . . | 990 | 0.0e+001 |
| 57. >gb\|KP745685.1\| Human herpesvirus 5 strain CZ/3/2012, complete ge . . . | 990 | 0.0e+001 |
| 58. >gb\|KP745655.1\| Human herpesvirus 5 strain BE/3/2010, complete ge . . . | 990 | 0.0e+001 |
| 59. >gb\| KP745653.1\| Human herpesvirus 5 strain BE/22/2011, complete g . . . | 990 | 0.0e+001 |
| 60. >gb\|JX512201.1\| Human herpesvirus 5 strain HAN3, complete genome | 990 | 0.0e+001 |
| 61. >gb\|KJ361969.1\| Human herpesvirus 5 strain PAV25, complete genome | 986 | 0.0e+001 |
| 62. >gb\|KJ361961.1\| Human herpesvirus 5 strain PAV5, complete genome | 986 | 0.0e+001 |
| 63. >gb\|KP745690.1\| Human herpesvirus 5 strain BE/34/2011, complete g . . . | 986 | 0.0e+001 |
| 64. >gb\|KP745663.1\| Human herpesvirus 5 strain BE/5/2010, complete ge . . . | 986 | 0.0e+001 |
| 65. >gb\|KP745640.1\| Human herpesvirus 5 strain BE/22/2010, complete g . . . | 986 | 0.0e+001 |
| 66. >gb\|GQ222011.2\| Human herpesvirus 5 strain 309, partial genome | 986 | 0.0e+001 |
| 67. >gb\|GQ466044.1\| Human herpesvirus 5 strain 3301, complete genome | 986 | 0.0e+001 |
| 68. >gb\|KT726950.2\| Human betaherpesvirus 5 strain UK/Lon7/Urine/2011 . . . | 984 | 0.0e+001 |
| 69. >gb\|KR534213.1\| Human herpesvirus 5 strain JER5695, complete geno . . . | 984 | 0.0e+001 |
| 70. >gb\|KJ361954.1\| Human herpesvirus 5 strain HAN32, complete genome | 984 | 0.0e+001 |
| 71. >gb\|KJ361953.1\| Human herpesvirus 5 strain HAN30, complete genome | 984 | 0.0e+001 |
| 72. >gb\|KP745725.1\| Human herpesvirus 5 strain BE/49/2011, complete g . . . | 984 | 0.0e+001 |
| 73. >gb\|KP745704.1\| Human herpesvirus 5 strain BE/32/2011, complete g . . . | 984 | 0.0e+001 |
| 74. >gb\|KP745694.1\| Human herpesvirus 5 strain BE/12/2010, complete g . . . | 984 | 0.0e+001 |
| 75. >gb\|KP745677.1\| Human herpesvirus 5 strain BE/1/2010, complete ge . . . | 984 | 0.0e+001 |
| 76. >gb\|KP745638.1\| Human herpesvirus 5 strain BE/15/2010, complete g . . . | 984 | 0.0e+001 |
| 77. >gb\|KP745637.1\| Human herpesvirus 5 strain BE/9/2011, complete ge . . . | 984 | 0.0e+001 |
| 78. >gb\|JX512206.1\| Human herpesvirus 5 strain HAN22, complete genome | 984 | 0.0e+001 |
| 79. >gb\|JX512202.1\| Human herpesvirus 5 strain HAN8, complete genome | 984 | 0.0e+001 |
| 80. >gb\|GQ222016.2\| Human herpesvirus 5 strain NT, partial genome | 984 | 0.0e+001 |
| 81. >gb\|KT726948.2\| Human betaherpesvirus 5 strain UK/Lon2/Blood/2013 . . . | 980 | 0.0e+001 |
| 82. >gb\|KT726947.2\| Human betaherpesvirus 5 strain UK/Lon1/Blood/2013 . . . | 980 | 0.0e+001 |
| 83. >gb\|KX544833.1\| Human herpesvirus 5 isolate VR3908, complete geno . . . | 980 | 0.0e+001 |
| 84. >gb\|KR534204.1\| Human herpesvirus 5 strain JER3855, complete geno . . . | 980 | 0.0e+001 |
| 85. >gb\|KJ361959.1\| Human herpesvirus 5 strain PAV1, complete genome | 980 | 0.0e+001 |
| 86. >gb\|KP745724.1\| Human herpesvirus 5 strain BE/4/2012, complete ge . . . | 980 | 0.0e+001 |
| 87. >gb\|KJ872540.1\| Human herpesvirus 5 strain PAV18, complete genome | 980 | 0.0e+001 |
| 88. >gb\|KJ426589.1\| Human herpesvirus 5 isolate HAN, complete genome | 980 | 0.0e+001 |
| 89. >gb\|GQ222010.2\| Human herpesvirus 5 strain 66, partial genome | 980 | 0.0e+001 |
| 90. >gb\|GU179289.1\| Human herpesvirus 5 strain VR1814, complete genome | 980 | 0.0e+001 |
| 91. >gb\|AC146907.1\| Human Herpesvirus 5 FIX-BAC isolate, complete seq . . . | 980 | 0.0e+001 |

TABLE 2-continued

BLAST Search Results for iP2

| Sequences producing high-scoring segment pairs: | High Score | E Value N |
|---|---|---|
| 92. >gb\|KT726944.2\| Human betaherpesvirus 5 strain NL/Rot5/Urine/2012 . . . | 978 | 0.0e+001 |
| 93. >gb\|KY490076.1\| Human betaherpesvirus 5 strain HANRTR8, complete . . . | 976 | 0.0e+001 |
| 94. >gb\|KY490072.1\| Human betaherpesvirus 5 strain HANChild2&3, compl . . . | 976 | 0.0e+001 |
| 95. >gb\|KY978851.1\| Synthetic construct Pfs28-SnoopTag gene, complete . . . | 976 | 0.0e+001 |
| 96. >gb\|KU317610.1\| Synthetic construct Human herpesvirus 5, complete . . . | 976 | 0.0e+001 |
| 97. >gb\|KT726955.2\| Human betaherpesvirus 5 strain UK/Lon5/Blood/2010 . . . | 976 | 0.0e+001 |
| 98. >gb\|KT726953.2\| Human betaherpesvirus 5 strain UK/Lon9/Urine/2012 . . . | 976 | 0.0e+001 |
| 99. >gb\|KR534208.1\| Human herpesvirus 5 strain JER4559, complete geno . . . | 976 | 0.0e+001 |
| 100. >gb\|KU302811.1\| Synthetic construct pENTR4-Pfs25-SpyTag sequence | 976 | 0.0e+001 |

The BLAST search showed that over 100 strains of HCMV had a least 99% sequence identity over the iP2 query sequence. The alignment data between the query sequence and "hit" #100, >gb|KU302811.1| Synthetic construct pENTR4-Pfs25-SpyTag sequence Length=3400 was: Score=881.3 bits (976), Expect=0.0e+00 Identities=494/498 (99%), Positives=494/498 (99%), Gaps=0/498 (0%).

An exemplary sequence alignment of TB40, and several other exemplary strains of HCMV including AD169, Merlin, and Towne is illustrated in FIG. 12.

The properly coordinated expression of viral transactivators is important to viral fitness (Goodrum, et al., *Proceedings of the National Academy of Sciences of the United States of America*, 99, 16255-16260 (2002)). Previous models for the regulation of IE gene expression during HCMV reactivation are incomplete. Because the MIEP is the primary regulator of IE1 and IE2 transcription during lytic replication, it was previously believed that the re-expression of IE1 and IE2 during reactivation required de-repression of the silenced MIEP (FIG. 1A). The data presented herein indicates that this long-held model is incorrect, and instead identifies a new paradigm for transcriptional regulation of IE1 and IE2 expression during HCMV reactivation (FIG. 1B). The results show that the MIEP remains silent when latently infected cells are exposed to reactivation stimuli (FIG. 2). Instead, the alternative MIE promoters the first MIE intron (Arend, et al., *Journal of Virology*, 90, 8855-8865 (2016)) are activated to high levels (FIGS. 2, 3A-3B, 4A-4B, and 5). Further, the data shows that deletion of the MIE promoters prevents IE1 and IE2 re-expression upon reactivation in experimental models of HCMV latency, but not during replication in fibroblasts (FIGS. 6A-6B and 7A-7D). The data also identifies the cellular FOXO TFs as key players in activation of these intronic MIE promoters. More specifically FOXO TFs are (i) sufficient to stimulate the activity of the MIE promoters in transient assays, and (ii) are transcriptionally induced and post-translationally activated by stimuli known to induce HCMV reactivation (FIGS. 8A-8C, 9A-9C, and 10). Taken together, these observations indicate that FOXO TFs compose an important cellular cue that triggers latently infected cells to reactivate the viral lytic replication cycle.

Finding that FOXO TFs regulate MIE expression in experimental models of HCMV latency provides an important missing link between changes in cell differentiation and the decision to reactivate from latency. Together the data support a model for the regulation of IE1 and IE2 expression during reactivation of latent HCMV infections (FIG. 1B). Changes to the extra- or intracellular environment of latently infected cells, such as cell stress or differentiation, lead to activation of FOXO family TFs. Activated FOXO TFs bind specific sites in the intronic MIE promoters to induce transcription of mRNAs encoding the full-length IE1 and IE2 proteins to reinitiate HCMV replication.

Example 4: Intronic Promoters can be Used for Transgene Expression

Materials and Methods

THP-1 Assays

THP-1 cells were infected with TB40/E WT, ΔiP1, ΔiP2 or ΔiP(1+2) HCMV (MOI=2) and cultured for 5 days to promote the establishment of latency. At day 5, cells were treated with TPA to promote monocyte-to-macrophage differentiation and viral reactivation. RNA was isolated, and RT-qPCR was performed to monitor accumulation of iP1-, iP2-, and MIEP/dP-derived transcripts relative to the low copy housekeeping gene H6PD. Data from three independent biological replicates (each performed in triplicate) is shown; standard deviation is depicted by error bars (FIG. 13A-13D).

Figures 13A, 13B, 13C, 13D:
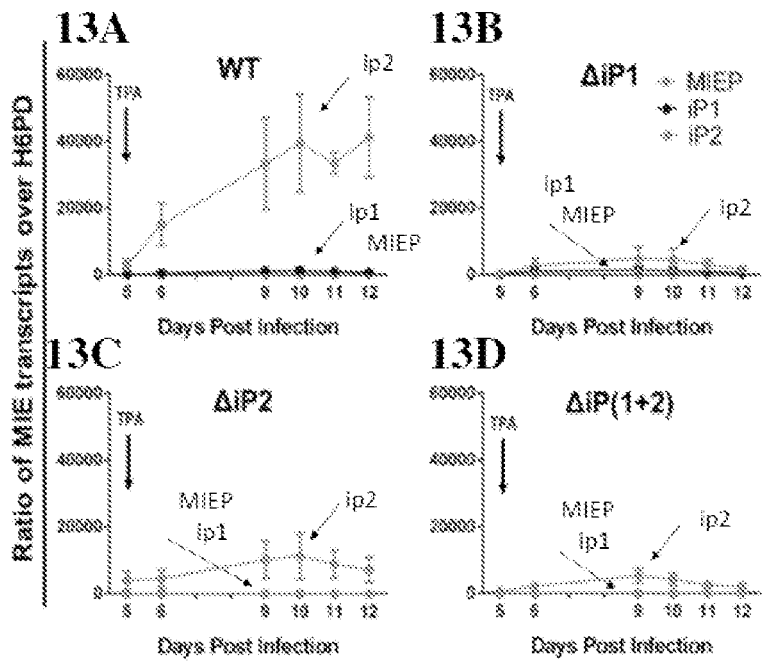
FIGS. 13A-13D are line graphs showing accumulation of iP1-, iP2, and MIEP/dP-derived transcripts (RNA) relative to the low copy housekeeping gene H6PD in TB40/E WT, ΔiP1, ΔiP2 or ΔiP(1+2) HCMV THP-1 cells.
Figure 13E:
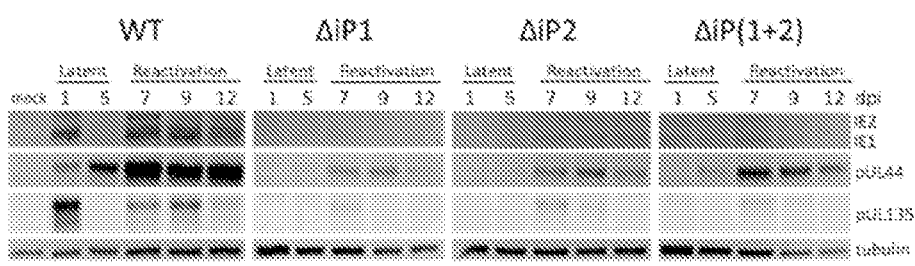
FIG. 13E is a western blot showing accumulation of IE1 and 1E2 proteins and viral early proteins pUL44 and pUL135 during latency and following reactivation stimulus in TB40/E WT, ΔiP1, ΔiP2 or ΔiP(1+2) HCMV THP-1 cells. Tubulin was used as a loading control. A single experiment representative of three is shown.

Accumulation of IE1 and IE2 protein was measured during latency and following reactivation stimulus by immunoblotting using mouse monoclonal antibodies recognizing both IE1 and IE2. Accumulation of viral early proteins pUL44 and pUL135 was also measured. Tubulin was used as a loading control. A single experiment (representative of three independent experiments) is shown (FIG. 13E).

Figure 13F:
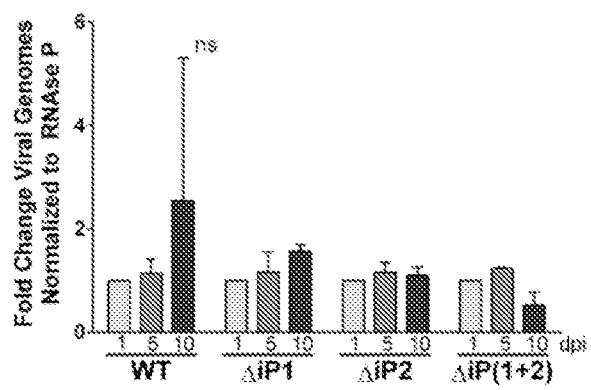
FIG. 13F is a bar graph showing viral genomes (DNA) isolated at days 1 and 5 during the latency periods at day 10 following TPA reactivation stimulus in TB40/E WT, ΔiP1, ΔiP2 or ΔiP(1+2) HCMV THP-1 cells.

Total DNA was isolated at days 1 and 5 during the latency period and at day 10 following TPA reactivation stimulus. Viral genomes were quantified by qPCR using a primer pair specific to the non-coding beta 2.7 region of the HCMV genome relative to BAC standard curve. Viral genome copy number was then normalized to the cellular gene RNAse P. Bars represent fold change over the number of viral genomes present at day 1 for each virus. Data from three independent biological replicates (each performed in duplicate) is shown; standard deviation is depicted by error bars (FIG. 13F). Two way ANOVA revealed that fold change in genome copy number is not statistically significant for any of the infection groups.

CD34+ HPC Assays

CD34+ HPCs were infected with TB40/E WT, ΔiP1, ΔiP2, and ΔiP(1+2) expressing GFP as a marker for infection for 24 hours at an MOI of 2. Pure populations of infected (GFP+) CD34+ cells were isolated by FACS and maintained in long-term bone marrow culture for 10 days.

Figure 14A:
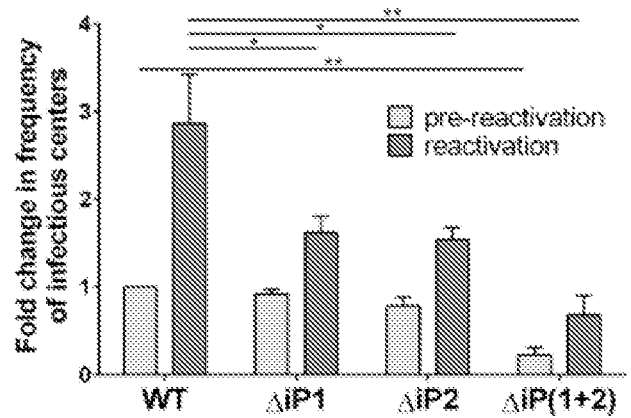
FIG. 14A is a bar graph showing the frequency of infectious centers formed pre- (left bars) and post- (right bars) reactivation in CD34+ HPCs infected with TB40/E WT, ΔiP1, ΔiP2, and ΔiP(1+2) expressing GFP as a marker for infection. Data from three independent biological replicates is shown; standard error is depicted by error bars. Statistical significance was determined by multiple t tests comparing each mutant virus to the wildtype parental virus (* indicates a p value≤0.05; ** indicates a p value≤0.005).

Viable CD34+ HPCs were seeded by limiting dilution onto monolayers of permissive fibroblasts in a cytokine-rich media to promote myeloid differentiation (reactivation, dark gray). An equivalent number of cells was mechanically lysed and seeded in parallel to determine the infectious virus present in the culture prior to reactivation (pre-reactivation, light gray). The frequency of infectious centers formed pre- and post-reactivation was determined 14 days later by extreme limiting dilution analysis from the fraction of GFP+ wells at each dilution. Data is expressed as fold change over the frequency of infectious centers produced by the wildtype virus prior to reactivation. Data from three independent biological replicates is shown; standard error is depicted by error bars (FIG. 14A). Statistical significance was determined by multiple t tests comparing each mutant virus to the wildtype parental virus (* indicates a p value≤0.05; ** indicates a p value≤0.005).

Figure 14B:
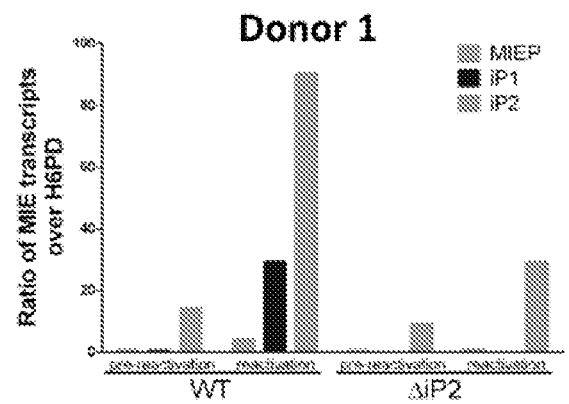
FIGS. 14B and 14C are bar graphs showing iP1- (center bars), iP2- (right bars), and MIEP/dP (left bars)-derived transcripts present in pre-reactivation and reactivation samples. Data from two independent biological replicates (qPCR reaction performed in triplicate) ("Donor 1" (14B), and "Donor 2" (14C)) using cells from multiple donors are shown.
Figure 14C:
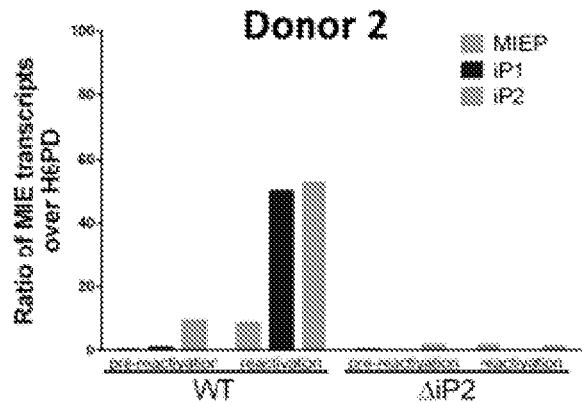

CD34+ HPCs infected with WT or ΔiP2 virus were used in a modified "cell-free" reactivation assay (absent co-culture with permissive fibroblasts) to quantify iP1-, iP2-, and MIEP/dP-derived transcripts present in pre-reactivation and reactivation samples. At day 10, RNA was collected from latently infected cells for the pre-reactivation time point. The remaining cells were plated in reactivation media enriched with 45 ng/mL of IL-6, G-CSF, and GM-CSF for 7 days before RNA was collected from adherent cells. RT-qPCR was performed to quantify discrete MIE transcripts relative to the low copy housekeeping gene H6PD in each sample. Data from two independent biological replicates (qPCR reaction performed in triplicate) using cells from multiple donors are shown (FIG. 14B-14C).

Results

Gene therapy can include the replacement, alteration, or supplementation of a defective or insufficiently expressed gene in order to prevent or ameliorate disease. It is often desirable for gene therapies to be applied in a highly controlled manner, such that genes are introduced into appropriate cell types and expressed at suitable levels. Hematopoietic cells are an attractive target for gene therapy because of the relative ease to which they can be acquired from children and adults, and because of the self-renewing potential of hematopoietic stem cells (HSCs). Transfer of an expression vector into relatively few HSC results in repopulation of most of the hematopoietic compartment and lineages.

Promoters that can drive enduring gene expression in a cell-type specific manner are of importance to successful gene therapy (Yam, *Molecular Therapy: The Journal of the American Society of Gene Therapy* 5, 479-484 (2002), Malik, *Blood,* 86, 2993-3005 (1995)). Viral promoters have been of interest due to their strength and the fact that similar sequences do not exist in human cells. However, gene expression from viral promoters is often silenced in HSCs (Challita, et al., *Proceedings of the National Academy of Sciences of the United States of America* 91, 2567-2571 (1994), Baum, *Journal of Virology* 69, 7541-7547 (1995)). For example, the CMV major immediate early promoter (MIEP; also commonly referred to as the CMV promoter) has high activity in many cell types (e.g. fibroblasts, epithelial cells, endothelial cells), but is diminished in hematopoietic cells (Baum, *Journal of Virology* 69, 7541-7547 (1995), Ramezani, et al., *Molecular Therapy: The Journal of the American Society of Gene Therapy* 2, 458-469 (2000)) as well as in other cell types (Brooks, *J Gene Med* 6, 395-404 (2004), Guo, *Gene Ther.* 3, 802-810 (1996)).

The MIEP, but not the MIE intronic promoters, are silenced in two hematopoietic cell types, the THP-1 monocytic cell line and primary CD34+ hematopoietic cells (FIGS. 3A-3B and 5). The MIE intronic promoters are also required for reactivation or viral gene expression in the THP-1 cell line (FIGS. 13A-13F) and primary CD34+ HPCs (FIGS. 14A-14C).

For example, FIG. 13A-13F illustrate that iP mutant viruses fail to express IE1 and IE2 following reactivation stimulus in THP-1 cells.

FIG. 14A-14C illustrate that the intronic promoters are required for reactivation of HCMV from latency in CD34+ HPCs.

Based on these findings, the MIE intronic promoters are believed to be useful to drive transgene expression in hematopoietic cells, possibly in a differentiation specific manner.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A hematopoietic cell comprising a nucleic acid comprising promoter elements of the iP1 promoter or a homolog thereof, the iP2 promoter or a homolog thereof, or a combination thereof operably linked to a heterologous transgene.

2. The hematopoietic cell of claim 1 comprising the nucleic acid of any one of SEQ ID NO:1-6 or a functional fragment thereof or a variant thereof comprising at least 80% sequence identity to any one of SEQ ID NOS:1-6 operably linked to a heterologous transgene.

3. The hematopoietic cell of claim 1, wherein the transgene encodes a therapeutic protein, a functional nucleic acid, or a gene editing molecule.

4. A composition comprising a plurality of the hematopoietic cells of claim 1.

5. A method of treating a subject in need thereof comprising administering the subject an effective amount of a composition comprising a plurality of the hematopoietic cells of claim 3.

6. A pharmaceutical composition comprising an effective amount of a virus to induce an immune response to an antigen encoded by virus's genome, the virus's genome comprising one or more mutations that reduces expression from one or more promoters that regulate expression of viral genes during reactivation from latency.

7. The pharmaceutical composition of claim 6, wherein the mutation is in a region of a viral genome that includes promoter elements of the iP1 promoter or a homolog thereof, the iP2 promoter or a homolog thereof, or a combination thereof.

8. The pharmaceutical composition of claim 6, wherein the mutation reduces the ability of one or more transcription factors to bind to or otherwise activate expression from the promoter.

9. The pharmaceutical composition of claim 7, wherein the mutation is deletion of a section or all of any one of SEQ ID NO:1-6, or a homologous sequence thereto.

10. The pharmaceutical composition of claim 6, wherein the virus further comprises one or more mutations in one or more genes important for viral tropism, one or more genes important for infection, one or more genes important for replication, one or more additional genes important for reactivation, one or more genes important for encoding an immunomodulatory protein, or a combination thereof.

11. The pharmaceutical composition of claim 6, wherein the virus is a herpesvirus.

12. The pharmaceutical composition of claim 11, wherein the virus is a cytomegalovirus (CMV).

13. The pharmaceutical composition of claim 6, wherein the viral genome further comprises an expression control sequence operably linked to a sequence encoding a heterologous antigen.

14. The pharmaceutical composition of claim 6, further comprising an adjuvant.

15. A method of treating a subject in need thereof comprising administering to the subject the pharmaceutical composition of claim 6.

16. The method of claim 15, wherein in the subject is administered two or more different pharmaceutical compositions of claim 6.

17. A method of vaccinating a subject against CMV comprising administering the subject the CMV of claim 12, wherein the CMV comprises one or more mutations in the iP1 promoter, the iP2 promoter, or combination thereof effective to reduce or eliminate promoter activity during reactivation from latency.

18. A CMV comprising (a) one or more mutations in the iP1 promoter, the iP2 promoter, or combination thereof effective to reduce or eliminate promoter activity during reactivation from latency, and (b) an expression control sequence operably linked to a sequence encoding a heterologous antigen.

19. A method of vaccinating a subject against a heterologous antigen comprising administering the subject the CMV of claim 18.

* * * * *

UNITED STATES PATENT AND TRADEMARK OFFICE
CERTIFICATE OF CORRECTION

PATENT NO. : 11,617,788 B2
APPLICATION NO. : 17/259352
DATED : April 4, 2023
INVENTOR(S) : Felicia Goodrum, Nathaniel Moorman and Jeremy Kamil It is certified that error appears in the above-identified patent and that said Letters Patent is hereby corrected as shown below:

On the Title Page (73), Assignees, replace:
"The Board of Supervisors of Louisiana State University and Agricultura and Mechanical College"
With:
--The Board of Supervisors of Louisiana State University and Agricultural and Mechanical College--

In the Claims

Claim 6, Column 71, Lines 20-25, replace the following text:
"A pharmaceutical composition comprising an effective amount of a virus to induce an immune response to an antigen encoded by virus's genome, the virus's genome comprising one or more mutations that reduces expression from one or more promoters that regulate expression of viral genes during reactivation from latency."
With the following text:
--A pharmaceutical composition comprising an effective amount of a virus to induce an immune response to an antigen encoded by the virus's genome, the virus's genome comprising one or more mutations that reduces expression from one or more promoters that regulate expression of viral genes during reactivation from latency, wherein the mutation is in a region of the viral genome that includes promoter elements of the iP1 promoter or a homolog thereof, the iP2 promoter or a homolog thereof, or a combination thereof.--

Claim 7, Column 71, Lines 26-30, replace the following text:
"The pharmaceutical composition of claim 6, wherein the mutation is in a region of a viral genome that includes promoter elements of the iPl promoter or a homolog thereof, the iP2 promoter or a homolog thereof, or a combination thereof."
With the following text:
--The pharmaceutical composition of claim 6, wherein the mutation is in a region of the viral genome comprising any one of SEQ ID NOS:1-6, or a functional fragment thereof, or a sequence with at least 60, 70, 80, 85, 90, 95, 96, 97, 98, or 99% sequence identity to any one of SEQ ID NOS:1-6.--

Signed and Sealed this
Twenty-fourth Day of September, 2024

Katherine Kelly Vidal
*Director of the United States Patent and Trademark Office*

SEQUENCE LISTING

```
<160> NUMBER OF SEQ ID NOS: 18

<210> SEQ ID NO 1
<211> LENGTH: 827
<212> TYPE: DNA
<213> ORGANISM: Artificial Sequence
<220> FEATURE:
<223> OTHER INFORMATION: synthetic nucleic acid

<400> SEQUENCE: 1
gtaagtaccg cctatagact ctataggccc accccttgg cttcttatgc atgctatact      60
gtttttggct tggggtctat acaccccgc ttccttatgc tataggtgat ggtatagctt     120
agcctatagg tgtgggttat tgaccattat tgaccactcc cctattggtg acgatacttt    180
ccattactaa tccataacat ggctctttgc cacaactctc tttattggct atatgccaat    240
actctgtcct tcagagactg acacggactc tgtatttta caggatgggg tcccatttat    300
tatttacaaa ttcacatata caacaacacc gtccccagta cccgcagttt ttattaaaca    360
```

| | |
|---|---|
| tagcgtggga tctccacgcg aatctcgggt acgtgttccg gacatgggct cttctccggt | 420 |
| agcggcggag cttctacatc cgagccctgc tcccatgcct ccagcggctc atggtcgctt | 480 |
| ggcagctcct tgctcctaac agtggaggcc agacttaggc acagcacgat gcccaccacc | 540 |
| accagtgtgc cgcacaaggc cgtggcgtta gggtatgtgt ctgaaaatga gctcggggag | 600 |
| cgggcttgca ccgctgacgc atttggaaga cttaaggcag cggcagaaga agatgcaggc | 660 |
| agctgagttg ttgtgttctg ataagagtca gaggtaactc ccgttgcggt gctgttaacg | 720 |
| gtggagggca gtgtagtctg agcagtactc gttgctgccg cgcgcgccac cagacataat | 780 |
| agctgacaga ctaacagact gttccttccc atgggtcttt tctgcag | 827 |

```
<210> SEQ ID NO 2
<211> LENGTH: 827
<212> TYPE: DNA
<213> ORGANISM: Artificial Sequence
<220> FEATURE:
<223> OTHER INFORMATION: synthetic polynucleotide

<400> SEQUENCE: 2
```

| | |
|---|---|
| gtaagtaccg cctatagagt ctataggccc accccttgg cttcttatgc atgctatact | 60 |
| gttttttggct tggggtctat acaccccgc ttcctcatgt tataggtgat ggtatagctt | 120 |
| agcctatagg tgtgggttat tgaccattat tgaccactcc cctattggtg acgatacttt | 180 |
| ccattactaa tccataacat ggctctttgc cacaactctc tttattggct atatgccaat | 240 |
| acactgtcct tcagagactg acacggactc tgtattttta caggatgggg tctcatttat | 300 |
| tatttacaaa ttcacatata caacaccacc gtccccagtg cccgcagttt ttattaaaca | 360 |
| taacgtggga tctccacgcg aatctcgggt acgtgttccg gacatgggct cttctccggt | 420 |
| agcggcggag cttctacatc cgagccctgc tcccatgcct ccagcgactc atggtcgctc | 480 |
| ggcagctcct tgctcctaac agtggaggcc agacttaggc acagcacgat gcccaccacc | 540 |
| accagtgtgc cgcacaaggc cgtggcggta gggtatgtgt ctgaaaatga gctcggggag | 600 |
| cgggcttgca ccgctgacgc atttggaaga cttaaggcag cggcagaaga agatgcaggc | 660 |
| agctgagttg ttgtgttctg ataagagtca gaggtaactc ccgttgcggt gctgttaacg | 720 |
| gtggagggca gtgtagtctg agcagtactc gttgctgccg cgcgcgccac cagacataat | 780 |
| agctgacaga ctaacagact gttccttccc atgggtcttt tctgcag | 827 |

```
<210> SEQ ID NO 3
<211> LENGTH: 500
<212> TYPE: DNA
<213> ORGANISM: Artificial Sequence
<220> FEATURE:
<223> OTHER INFORMATION: synthetic polynucleotide

<400> SEQUENCE: 3
```

| | |
|---|---|
| atcgcctgga gacgccatcc acgctgtttt gacctccata gaagacaccg ggaccgatcc | 60 |
| agcctccgcg gccgggaacg gtgcattgga acgcggattc ccgtgccaa gagtgacgta | 120 |
| agtaccgcct atagactcta taggcccacc cccttggctt cttatgcatg ctatactgtt | 180 |
| tttggcttgg ggtctataca ccccgcttc cttatgctat aggtgatggt atagcttagc | 240 |
| ctataggtgt gggttattga ccattattga ccactcccct attggtgacg atactttcca | 300 |
| ttactaatcc ataacatggc tctttgccac aactctcttt attggctata tgccaatact | 360 |
| ctgtccttca gagactgaca cggactctgt attttacag gatggggtcc catttattat | 420 |

```
ttacaaattc acatatacaa caacaccgtc cccagtaccc gcagttttta ttaaacatag    480
cgtgggatct ccacgcgaat                                                500

<210> SEQ ID NO 4
<211> LENGTH: 500
<212> TYPE: DNA
<213> ORGANISM: Artificial Sequence
<220> FEATURE:
<223> OTHER INFORMATION: synthetic polynucleotide

<400> SEQUENCE: 4
atcgcctgga gacgccatcc acgctgtttt gacctccata gaagacaccg ggaccgatcc    60
agcctccgcg gccgggaacg gtgcattgga acgcggattc cccgtgccaa gagtgacgta   120
agtaccgcct atagagtcta taggcccacc cccttggctt cttatgcatg ctatactgtt   180
tttggcttgg ggtctataca cccccgcttc ctcatgttat aggtgatggt atagcttagc   240
ctataggtgt gggttattga ccattattga ccactcccct attggtgacg atactttcca   300
ttactaatcc ataacatggc tctttgccac aactctcttt attggctata tgccaataca   360
ctgtccttca gagactgaca cggactctgt attttttacag gatggggtct catttattat   420
ttacaaattc acatatacaa caccaccgtc cccagtgccc gcagttttta ttaaacataa   480
cgtgggatct ccacgcgaat                                                500

<210> SEQ ID NO 5
<211> LENGTH: 500
<212> TYPE: DNA
<213> ORGANISM: Artificial Sequence
<220> FEATURE:
<223> OTHER INFORMATION: synthetic polynucleotide

<400> SEQUENCE: 5
aacaccgtcc ccagtacccg cagttttat taaacatagc gtgggatctc cacgcgaatc     60
tcgggtacgt gttccggaca tgggctcttc tccggtagcg gcggagcttc tacatccgag   120
ccctgctccc atgcctccag cggctcatgg tcgcttggca gctccttgct cctaacagtg   180
gaggccagac ttaggcacag cacgatgccc accaccacca gtgtgccgca caaggccgtg   240
gcggtagggt atgtgtctga aaatgagctc ggggagcggg cttgcaccgc tgacgcattt   300
ggaagactta aggcagcggc agaagaagat gcaggcagct gagttgttgt gttctgataa   360
gagtcagagg taactcccgt tgcggtgctg ttaacggtgg agggcagtgt agtctgagca   420
gtactcgttg ctgccgcgcg cgccaccaga cataatagct gacagactaa cagactgttc   480
ctttccatgg gtcttttctg                                                500

<210> SEQ ID NO 6
<211> LENGTH: 500
<212> TYPE: DNA
<213> ORGANISM: Artificial Sequence
<220> FEATURE:
<223> OTHER INFORMATION: synthetic polynucleotide

<400> SEQUENCE: 6
accaccgtcc ccagtgcccg cagttttat taaacataac gtgggatctc cacgcgaatc     60
tcgggtacgt gttccggaca tgggctcttc tccggtagcg gcggagcttc tacatccgag   120
ccctgctccc atgcctccag cgactcatgg tcgctcggca gctccttgct cctaacagtg   180
gaggccagac ttaggcacag cacgatgccc accaccacca gtgtgccgca caaggccgtg   240
gcggtagggt atgtgtctga aaatgagctc ggggagcggg cttgcaccgc tgacgcattt   300
```

```
ggaagactta aggcagcggc agaagaagat gcaggcagct gagttgttgt gttctgataa    360
gagtcagagg taactcccgt tgcggtgctg ttaacggtgg agggcagtgt agtctgagca    420
gtactcgttg ctgccgcgcg cgccaccaga cataatagct gacagactaa cagactgttc    480
ctttccatgg gtcttttctg                                                500

<210> SEQ ID NO 7
<211> LENGTH: 538
<212> TYPE: DNA
<213> ORGANISM: Artificial Sequence
<220> FEATURE:
<223> OTHER INFORMATION: synthetic polynucleotide

<400> SEQUENCE: 7
gtaagtaccg cctatagact ctataggccc ataacttcgt atagcataca ttatacgaag     60
ttatttaaac atagcgtggg atctccacgc gaatctcggg tacgtgttcc ggacatgggc    120
tcttctccgg tagcggcgga gcttctacat ccgagccctg ctcccatgcc tccagcggct    180
catggtcgct tggcagctcc ttgctcctaa cagtggaggc cagacttagg cacagcacga    240
tgcccaccac caccagtgtg ccgcacaagg ccgtggcggt agggtatgtg tctgaaaatg    300
agctcgggga gcgggcttgc accgctgacg catttggaag acttaaggca gcggcagaag    360
aagatgcagg cagctgagtt gttgtgttct gataagagtc agaggtaact cccgttgcgg    420
tgctgttaac ggtggagggc agtgtagtct gagcagtact cgttgctgcc gcgcgcgcca    480
ccagacataa tagctgacag actaacagac tgttcctttc catgggtctt ttctgcag     538

<210> SEQ ID NO 8
<211> LENGTH: 451
<212> TYPE: DNA
<213> ORGANISM: Artificial Sequence
<220> FEATURE:
<223> OTHER INFORMATION: synthetic polynucleotide

<400> SEQUENCE: 8
gtaagtaccg cctatagact ctataggccc acccccttgg cttcttatgc atgctatact     60
gtttttggct tggggtctat acaccccgc ttccttatgc tataggtgat ggtatagctt    120
agcctatagg tgtgggttat tgaccattat tgaccactcc cctattggtg acgtactttt    180
ccattactaa tccataacat ggctctttgc cacaactctc tttattggct atatgccaat    240
actctgtcct tcagagactg acacggactc tgtatttta caggatgggg tcccatttat    300
tatttacaaa ttcacatata caacaacacc gtccccagta cccgataact tcgtatagca    360
tacattatac gaagttatct gccgcgcgcg ccaccagaca taatagctga cagactaaca    420
gactgttcct ttccatgggt cttttctgca g                                  451

<210> SEQ ID NO 9
<211> LENGTH: 137
<212> TYPE: DNA
<213> ORGANISM: Artificial Sequence
<220> FEATURE:
<223> OTHER INFORMATION: synthetic polynucleotide

<400> SEQUENCE: 9
gtaagtaccg cctatagact ctataggccc ataacttcgt atagcataca ttatacgaag     60
ttatctgccg cgcgccac cagacataat agctgacaga ctaacagact gttcctttcc    120
atgggtcttt tctgcag                                                  137
```

<210> SEQ ID NO 10
<211> LENGTH: 505
<212> TYPE: DNA
<213> ORGANISM: Artificial Sequence
<220> FEATURE:
<223> OTHER INFORMATION: synthetic polynucleotide

<400> SEQUENCE: 10

| | | | | | |
|---|---|---|---|---|---|
| gtaagtaccg | cctatagact | ctataggccc | attaaacata | gcgtgggatc | tccacgcgaa | 60 |
| tctcgggtac | gtgttccgga | catgggctct | tctccggtag | cggcggagct | tctacatccg | 120 |
| agccctgctc | ccatgcctcc | agcggctcat | ggtcgcttgg | cagctccttg | ctcctaacag | 180 |
| tggaggccag | acttaggcac | agcacgatgc | ccaccaccac | cagtgtgccg | cacaaggccg | 240 |
| tggcggtagg | gtatgtgtct | gaaaatgagc | tcggggagcg | ggcttgcacc | gctgacgcat | 300 |
| ttggaagact | taaggcagcg | gcagaagaag | atgcaggcag | ctgagttgtt | gtgttctgat | 360 |
| aagagtcaga | ggtaactccc | gttgcggtgc | tgttaacggt | ggagggcagt | gtagtctgag | 420 |
| cagtactcgt | tgctgccgcg | cgcgccacca | gacataatag | ctgacagact | aacagactgt | 480 |
| tcctttccat | gggtcttttc | tgcag | | | | 505 |

<210> SEQ ID NO 11
<211> LENGTH: 417
<212> TYPE: DNA
<213> ORGANISM: Artificial Sequence
<220> FEATURE:
<223> OTHER INFORMATION: synthetic polynucleotide

<400> SEQUENCE: 11

| | | | | | |
|---|---|---|---|---|---|
| gtaagtaccg | cctatagact | ctataggccc | accccttgg | cttcttatgc | atgctatact | 60 |
| gtttttggct | tggggtctat | acaccccgc | ttccttatgc | ataggtgat | ggtatagctt | 120 |
| agcctatagg | tgtgggttat | tgaccattat | tgaccactcc | cctattggtg | acgatacttt | 180 |
| ccattactaa | tccataacat | ggctctttgc | cacaactctc | tttattggct | atatgccaat | 240 |
| actctgtcct | tcagagactg | acacggactc | tgtattttta | caggatgggg | tcccatttat | 300 |
| tatttacaaa | ttcacatata | caacaacacc | gtccccagta | cccgctgccg | cgcgcgccac | 360 |
| cagacataat | agctgacaga | ctaacagact | gttccttttcc | atgggtcttt | tctgcag | 417 |

<210> SEQ ID NO 12
<211> LENGTH: 104
<212> TYPE: DNA
<213> ORGANISM: Artificial Sequence
<220> FEATURE:
<223> OTHER INFORMATION: synthetic polynucleotide

<400> SEQUENCE: 12

| | | | | | |
|---|---|---|---|---|---|
| gtaagtaccg | cctatagact | ctataggccc | actgccgcgc | gcgccaccag | acataatagc | 60 |
| tgacagacta | acagactgtt | cctttccatg | ggtcttttct | gcag | | 104 |

<210> SEQ ID NO 13
<211> LENGTH: 500
<212> TYPE: DNA
<213> ORGANISM: Artificial Sequence
<220> FEATURE:
<223> OTHER INFORMATION: synthetic polynucleotide

<400> SEQUENCE: 13

| | | | | | |
|---|---|---|---|---|---|
| attcgcgtgg | agatcccacg | ctatgtttaa | taaaaactgc | gggtactggg | gacggtgttg | 60 |
| ttgtatatgt | gaatttgtaa | ataataaatg | ggaccccatc | ctgtaaaaat | acagagtccg | 120 |

```
tgtcagtctc tgaaggacag agtattggca tatagccaat aaagagagtt gtggcaaaga    180
gccatgttat ggattagtaa tggaaagtat cgtcaccaat aggggagtgg tcaataatgg    240
tcaataaccc acacctatag gctaagctat accatcacct atagcataag gaagcggggg    300
tgtatagacc ccaagccaaa aacagtatag catgcataag aagccaaggg ggtgggccta    360
tagagtctat aggcggtact tacgtcactc ttggcacggg gaatccgcgt tccaatgcac    420
cgttcccggc cgcggaggct ggatcggtcc cggtgtcttc tatggaggtc aaaacagcgt    480
ggatggcgtc tccaggcgat                                                500
```

<210> SEQ ID NO 14
<211> LENGTH: 500
<212> TYPE: DNA
<213> ORGANISM: Artificial Sequence
<220> FEATURE:
<223> OTHER INFORMATION: synthetic polynucleotide

<400> SEQUENCE: 14

```
cagaaaagac ccatggaaag gaacagtctg ttagtctgtc agctattatg tctggtggcg     60
cgcgcggcag caacgagtac tgctcagact cactgccct ccaccgttaa cagcaccgca    120
acgggagtta cctctgactc ttatcagaac acaacaactc agctgcctgc atcttcttct    180
gccgctgcct taagtcttcc aaatgcgtca gcggtgcaag cccgctcccc gagctcattt    240
tcagacacat accctaccgc cacggccttg tgcggcacac tggtggtggt gggcatcgtg    300
ctgtgcctaa gtctggcctc cactgttagg agcaaggagc tgccaagcga ccatgagccg    360
ctggaggcat gggagcaggg ctcggatgta gaagctccgc cgctaccgga aagagcccca    420
tgtccggaac acgtacccga gattcgcgtg gagatcccac gctatgttta ataaaaactg    480
cgggtactgg ggacggtgtt                                                500
```

<210> SEQ ID NO 15
<211> LENGTH: 1800
<212> TYPE: DNA
<213> ORGANISM: Artificial Sequence
<220> FEATURE:
<223> OTHER INFORMATION: synthetic polynucleotide

<400> SEQUENCE: 15

```
attccccgtg ccaagagtga cgtaagtacc gcctatagac tctataggcc cacccccttg     60
gcttcttatg catgctatac tgttttggc ttggggtcta tacaccccg cttccttatg    120 ctataggtga tggtatagct tagcctatgg tgtgggttat tgaccattat tgaccactcc    180
cctattggtg acgatacttt ccattactaa tccataacat ggctctttgc cacaactctc    240
tttattggct atatgccaat actctgtcct tcagagactg acacggactc tgtatttta    300 caggataaaa tcccatttat tatttacaaa ttcacatata caacaacacc gtccccagta    360
cccgcagttt ttattaaaca tagcgtggat ctccacgcga atctcgggta cgtgttccgg    420
acatgggctc ttctccggta gcggcggagc ttctacatcc gagccctgct cccatgcctc    480
cagcggctca tggtcgcttg gcagctcctt gctcctaaca gtggaggcca gacttaggca    540
cagcacgatg cccaccacca ccagtgtgcc gcacaaggcc gtggcggtag ggtatgtgtc    600
tgaaaatgag ctcggggagc gggcttgcac cgctgacgca tttggaagac ttaaggcagc    660
ggcagaagaa gatgcaggca gctgagttgt tgtgttctga taagagtcag aggtaactcc    720
cgttgcggtg ctgttaacgg tggagggcag tgtactctga gcagtactcg ttgctgccgc    780
```

```
gcgcgccacc agacataata gctgacagac taacagactg ttcctttcca tgggtctttt    840
ctgcagtcac cgtccttgac acgatggagt cctctgccaa gagaaagatg gaccctgatc    900
cccgtgccaa gagtgacgta agtaccgcct atagactcta taggcccacc cccttggctt    960
cttatgcatg ctatactgtt tttggcttgg ggtctataca ccccgcttc cttatgctat    1020 aggtgatggt atagcttagc ctataggtgt gggttattga ccattattga ccactcccct    1080
attggtgacg atactttcca ttactaatcc ataacataac atggctcttt gccacaactc    1140
tctttattgg ctatatgcca atactctgcc ttcagagact gacacggact ctgtatttt    1200 acaggatggg gtcccattta ttatttacaa attcacatat acaacaacac cgtccccagt    1260
acccgcagtt tttattaaac atagcgtggg atctccacgc gaatctcggg tacgtgttcc    1320
ggacatgggc tcttctccgg tagcggcgga gcttctacat ccgagccctg ctccatgcct    1380
ccagcggctc atggtcgctt ggcagctcct tgctcctaac agtggaggcc agacttaggc    1440
acagcacgat gcccaccacc accagtgtgc cgcacaaggc cgtggcggta gggtatgtgt    1500
ctgcccctga gctcgggagc gggcttgcac cgctgacgca tttggaagac ttaaggcagc    1560
ggcagaagaa gatgcaggca gctgagttgt tgtgttctga taagagtcag aggtaactcc    1620
cgttgcggtg ctgttaacgg tggagggcag tgtagtctga gcagtactcg ttgctgccgc    1680
gcgcgccacc agacataata gctgacagac taacagactg ttcctttcca tgggtctttt    1740
ctgcagtcac cgtccttgac acgatggagt cctctgccaa gagaaagatg gaccctgaca    1800

<210> SEQ ID NO 16
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 16
taacttcgta tagcatacat tata                                             24

<210> SEQ ID NO 17
<211> LENGTH: 33
<212> TYPE: DNA
<213> ORGANISM: Artificial Sequence
<220> FEATURE:
<223> OTHER INFORMATION: synthetic polynucleotide

<400> SEQUENCE: 17
taacttcgta tagcatacat tatacgaagt tat                                   33

<210> SEQ ID NO 18
<211> LENGTH: 34
<212> TYPE: DNA
<213> ORGANISM: Artificial Sequence
<220> FEATURE:
<223> OTHER INFORMATION: synthetic polynucleotide

<400> SEQUENCE: 18
ataacttcgt atagcataca ttatacgaag ttat                                  34
```